(12) United States Patent
Inoue et al.

(10) Patent No.: US 10,109,806 B2
(45) Date of Patent: Oct. 23, 2018

(54) ORGANOMETALLIC COMPLEX, LIGHT-EMITTING ELEMENT, LIGHT-EMITTING DEVICE, ELECTRONIC APPLIANCE, AND LIGHTING DEVICE

(71) Applicant: SEMICONDUCTOR ENERGY LABORATORY CO., LTD., Kanagawa-ken (JP)

(72) Inventors: Hideko Inoue, Kanagawa (JP); Tomoya Yamaguchi, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 580 days.

(21) Appl. No.: 14/278,775

(22) Filed: May 15, 2014

(65) Prior Publication Data
US 2014/0339526 A1    Nov. 20, 2014

(30) Foreign Application Priority Data

May 20, 2013  (JP) ................................ 2013-106142

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ...... *H01L 51/0085* (2013.01); *C07F 15/0033* (2013.01); *C09K 11/06* (2013.01); *H01L 51/006* (2013.01); *H01L 51/0061* (2013.01); *H01L 51/0072* (2013.01); *C09K 2211/1007* (2013.01); *C09K 2211/1029* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 6,097,147 A | 8/2000 | Baldo et al. | |
| 6,830,828 B2 | 12/2004 | Thompson et al. | |
| 6,902,830 B2 | 6/2005 | Thompson et al. | |
| 7,001,536 B2 | 2/2006 | Thompson et al. | |
| 7,220,495 B2 | 5/2007 | Tsuboyama et al. | |
| 7,291,406 B2 | 11/2007 | Thompson et al. | |
| 7,354,662 B2 | 4/2008 | Tsuboyama et al. | |
| 7,537,844 B2 | 5/2009 | Thompson et al. | |
| 7,883,787 B2 | 2/2011 | Thompson et al. | |
| 9,200,022 B2 | 12/2015 | Inoue et al. | |
| 2005/0221123 A1 | 10/2005 | Inoue et al. | |
| 2007/0128466 A1* | 6/2007 | Nomura et al. | C09K 11/06 428/690 |
| 2007/0129545 A1 | 6/2007 | Inoue et al. | |
| 2007/0244320 A1 | 10/2007 | Inoue et al. | |
| 2009/0015143 A1 | 1/2009 | Inoue et al. | |
| 2009/0039776 A1 | 2/2009 | Yamada et al. | |
| 2010/0105902 A1 | 4/2010 | Inoue et al. | |
| 2011/0082296 A1 | 4/2011 | Inoue et al. | |
| 2011/0112296 A1 | 5/2011 | Thompson et al. | |
| 2012/0061707 A1 | 3/2012 | Seo et al. | |
| 2012/0098417 A1 | 4/2012 | Inoue et al. | |
| 2012/0104373 A1 | 5/2012 | Inoue et al. | |
| 2012/0208999 A1 | 8/2012 | Konno | |
| 2012/0274201 A1 | 11/2012 | Seo et al. | |
| 2013/0048964 A1 | 2/2013 | Takeda et al. | |
| 2013/0088144 A1 | 4/2013 | Inoue et al. | |
| 2013/0165653 A1 | 6/2013 | Inoue et al. | |
| 2013/0281693 A1 | 10/2013 | Inoue et al. | |

FOREIGN PATENT DOCUMENTS

| | | |
|---|---|---|
| JP | 2003-109758 A | 4/2003 |
| JP | 2008-010653 A | 1/2008 |
| JP | 2008-074921 A | 4/2008 |
| JP | 2008-081582 A | 4/2008 |
| JP | 2012-149030 A | 8/2012 |
| JP | 2012-231137 A | 11/2012 |

(Continued)

OTHER PUBLICATIONS

Niu et al., "Highly efficient red electrophosphorescent devices based on an iridium complex with trifluoromethyl-substituted pyrimidine ligand", Appl. Phys. Lett. (Applied Physics Letters), Aug. 30, 2004, vol. 85, No. 9, pp. 1619-1621.

Caygill et al., "Cyclometallated compounds IV. Cyclopalladation of phenylpyrimidines and X-ray structure of a doubly cyclopalladated derivative of 4,6-diphenylpyrimidine", Journal of Organometallic Chemistry, Feb. 13, 1990, vol. 382, No. 3, pp. 455-469.

Kawanishi et al., "Dependence of spectroscopic, electrochemical, and excited-state properties of tris chelate ruthenium(II) complexes on ligand structure", Inorg. Chem. (Inorganic Chemistry), 1989, vol. 28, No. 15, pp. 2968-2975.

Kozhevnikov et al., "Highly Luminescent Mixed-Metal Pt(II)/Ir(III) Complexes: Bis-Cyclometalation of 4,6-Diphenylpyrimidine as a Versatile Route to Rigid Multimetallic Assemblies", Inorg. Chem. (Inorganic Chemistry), 2011, vol. 50, No. 13, pp. 6304-6313.

Bredereck et al., "Formamide Reactions, VIII. A New Pyrimidine-Synthesis", Chem.Ber. (Chemische Berichte), 1957, vol. 90, pp. 942-952.

(Continued)

*Primary Examiner* — Marie R. Yamnitzky
(74) *Attorney, Agent, or Firm* — Husch Blackwell LLP

(57) ABSTRACT

A light-emitting element including a phosphorescent organometallic complex is provided. The organometallic complex emits phosphorescence in the yellow green to orange wavelength range and has high emission efficiency and high reliability. Thus, the organometallic complex that exhibits phosphorescence is provided. The organometallic complex, in which nitrogen at the 3-position of a pyrimidine ring is coordinated to a metal, a carbazole skeleton is bonded to the 4-position of the pyrimidine ring, and the carbazole skeleton is bonded to the metal, is used as an emission center. The metal is preferably a Group 9 element or a Group 10 element, more preferably iridium.

2 Claims, 32 Drawing Sheets

(56) References Cited

FOREIGN PATENT DOCUMENTS

| | | |
|---|---|---|
| JP | 2012-238854 | 12/2012 |
| TW | I231157 | 4/2005 |
| WO | WO-2000/070655 | 11/2000 |
| WO | WO 2008/044723 A1 | 4/2008 |
| WO | WO-2011/024737 | 3/2011 |
| WO | WO-2012/053627 | 4/2012 |
| WO | WO 2012/141185 A1 | 10/2012 |

OTHER PUBLICATIONS

Ge, G. et al., "Highly Efficient Phosphorescent iridium (III) diazine Complexes for OLEDs: Different Photophysical Property Between iridium (III) pyrazine Complex and iridium (III) pyrimidine Complex," Journal of Organometallic Chemistry, Sep. 1, 2009. vol. 694, No. 19, pp. 3050-3057.

* cited by examiner

FIG. 7A1  FIG. 7A2  FIG. 7A3
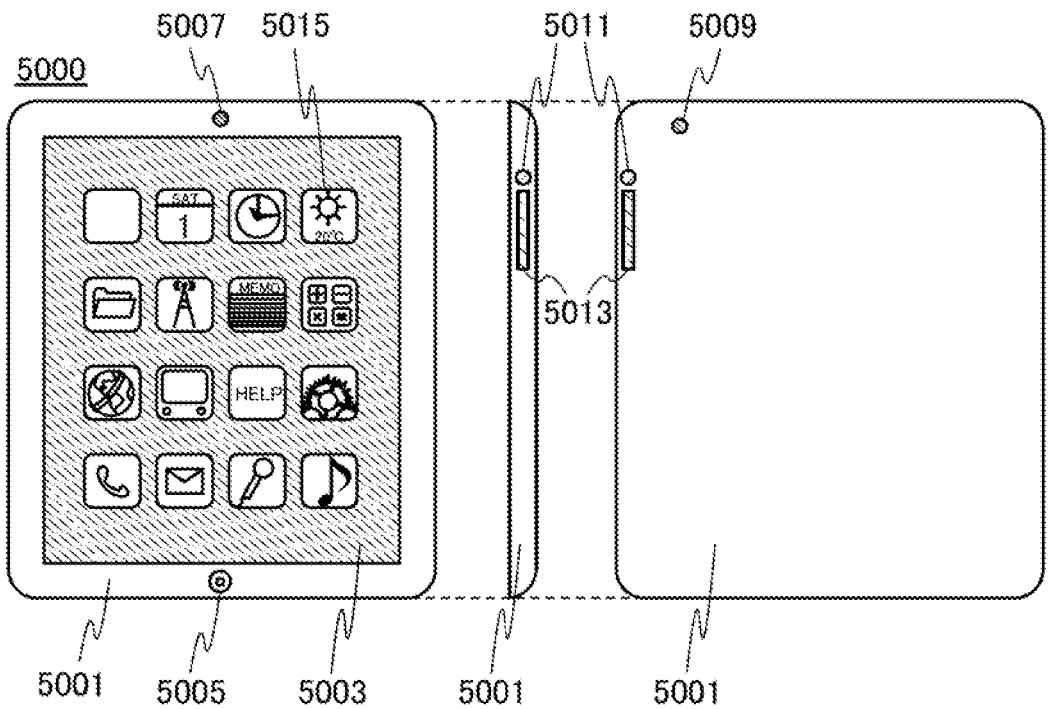
FIG. 7B
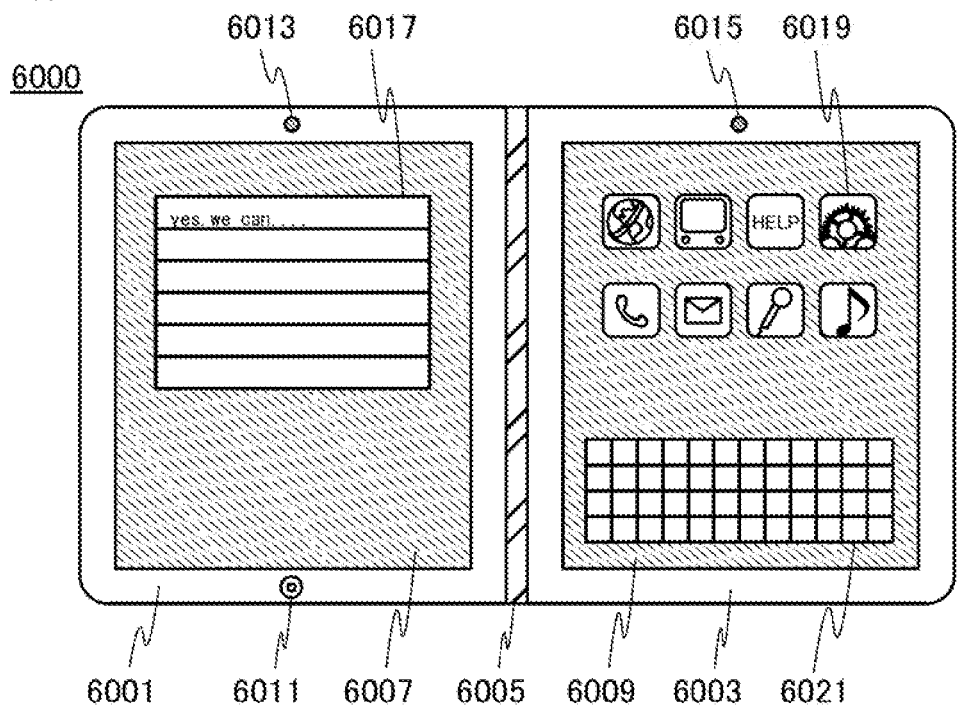

ORGANOMETALLIC COMPLEX, LIGHT-EMITTING ELEMENT, LIGHT-EMITTING DEVICE, ELECTRONIC APPLIANCE, AND LIGHTING DEVICE

BACKGROUND OF THE INVENTION

1. Field of the Invention

The present invention relates to an organometallic complex, a light-emitting element, a light-emitting device, an electronic appliance, and a lighting device.

2. Description of the Related Art

In recent years, research and development have been extensively conducted on light-emitting elements using electroluminescence (EL). In the basic structure of such a light-emitting element, a layer containing a light-emitting substance is interposed between a pair of electrodes. By applying voltage to this element, light emission from the light-emitting substance can be obtained.

The light-emitting element is a self-luminous element and thus has advantages over a liquid crystal display element, such as high visibility of the pixels and no need of backlight, and is considered to be suitable as a flat panel display element. Another major advantage of the light-emitting element is that it can be thin and lightweight. Besides, the EL element has an advantage of quite fast response speed.

Furthermore, since such a light-emitting element can be formed in a film form, the light-emitting element makes it possible to provide planar light emission; thus, a large-area element can be easily formed. Thus, a large-area element can be easily formed. This feature is difficult to obtain with point light sources typified by incandescent lamps and LEDs or linear light sources typified by fluorescent lamps. Thus, the light-emitting element also has great potential as a planar light source applicable to a lighting device and the like.

Such light-emitting elements utilizing electroluminescence can be broadly classified according to whether a light-emitting substance is an organic compound or an inorganic compound. In the case of an organic EL element in which a layer containing an organic compound used as a light-emitting substance is provided between a pair of electrodes, application of voltage to the light-emitting element causes injection of electrons from a cathode and holes from an anode into the layer containing the light-emitting organic compound and thus current flows. The injected electrons and holes then lead the organic compound to its excited state, whereby light emission is obtained from the excited organic compound.

The excited state of an organic compound can be a singlet excited state or a triplet excited state. Light emission from the singlet excited state (S*) is called fluorescence, and light emission from the triplet excited state (T*) is called phosphorescence. The statistical generation ratio of S* to T* in a light-emitting element is thought to be 1:3.

In a compound that converts singlet excitation energy into light emission (hereinafter, referred to as a fluorescent compound), at room temperature, emission from the triplet excited state (phosphorescence) is not observed while only emission from the singlet excited state (fluorescence) is observed. Therefore, in a light-emitting element with the use of a fluorescent compound, the theoretical limit of internal quantum efficiency (the ratio of generated photons to injected carriers) is considered to be 25% based on S*:T*=1:3.

In contrast, in a compound that converts triplet excitation energy into light emission (hereinafter, referred to as a phosphorescent compound), emission from the triplet excited state (phosphorescence) is observed. Since intersystem crossing (i.e., transition from a singlet excited state to a triplet excited state) easily occurs in a phosphorescent compound, the internal quantum efficiency can be theoretically increased to 100%. In other words, higher emission efficiency can be obtained than using a fluorescent compound. From such a reason, in order to achieve a high efficiency light-emitting element, a light-emitting element with the use of a phosphorescent compound has been actively developed recently.

When a light-emitting layer of a light-emitting element is formed using a phosphorescent compound described above, in order to suppress concentration quenching or quenching due to triplet-triplet annihilation in the phosphorescent compound, the light-emitting layer is often formed such that the phosphorescent compound is dispersed in a matrix of another compound. Here, the compound as the matrix is called a host material, and the compound dispersed in the matrix, such as a phosphorescent compound, is called a guest material (dopant).

As the guest material (dopant), an organometallic complex that has iridium (Ir) or the like as a central metal has particularly attracted attention because of its high phosphorescence quantum yield. A light-emitting device that includes, as a phosphorescent organometallic complex having iridium as a central metal, for example, a phosphorescent organometallic iridium complex where nitrogen at the 3-position of pyrimidine having an aryl group at the 4-position is coordinated to a metal, the pyrimidine has an alkyl group or an aryl group at any one of the 2-position, the 5-position, and the 6-position, and the aryl group at the 4-position of the pyrimidine has an ortho-metalated structure in which the ortho position of the aryl group is bonded to the metal is disclosed (e.g., see Patent Document 1).

PATENT DOCUMENT

Patent Document 1: Japanese Published Patent Application No. 2012-238854

SUMMARY OF THE INVENTION

As disclosed in Patent Document 1, a guest material of a phosphorescent compound is actively developed. However, light-emitting elements still need to be improved in terms of emission efficiency, reliability, emission characteristics, synthesis efficiency, and cost, and further development is expected for obtaining more excellent light-emitting elements.

In view of the above, an object of one embodiment of the present invention is to provide a light-emitting element that includes a phosphorescent organometallic complex. The organometallic complex exhibits phosphorescence in the yellow green to orange wavelength range and has high emission efficiency and high reliability. Thus, another object of one embodiment of the present invention is to provide the organometallic complex that exhibits phosphorescence.

Another object of one embodiment of the present invention is to provide a light-emitting device, an electronic appliance, and a lighting device that include the light-emitting element.

One embodiment of the present invention is a light-emitting element that includes, as an emission center, an organometallic complex in which nitrogen at the 3-position of a pyrimidine ring is coordinated to a metal, a carbazole skeleton is bonded to the 4-position of the pyrimidine ring, and the carbazole skeleton is bonded to the metal.

It is preferable that the metal in the above-described structure be a Group 9 element or a Group 10 element. It is preferable that the metal is selected from iridium, platinum, palladium, and rhodium. It is particularly preferable that the metal be iridium.

Another embodiment of the present invention is an organometallic complex that has a structure represented by General Formula (G1-1).

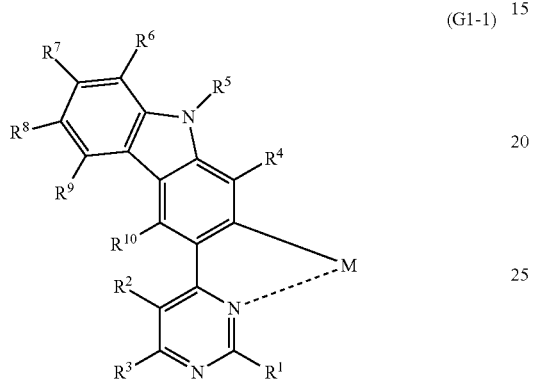

(G1-1)

In General Formula (G1-1), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element.

Another embodiment of the present invention is an organometallic complex that has a structure represented by General Formula (G1-2).

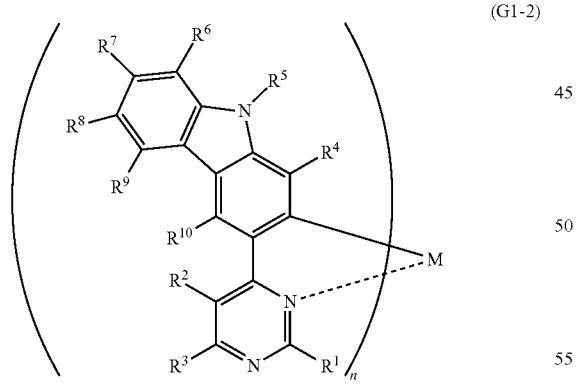

(G1-2)

In General Formula (G1-2), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 3 when M is a Group 9 element, and n is 2 when M is a Group 10 element.

Another embodiment of the present invention is an organometallic complex that has a structure represented by General Formula (G1-3).

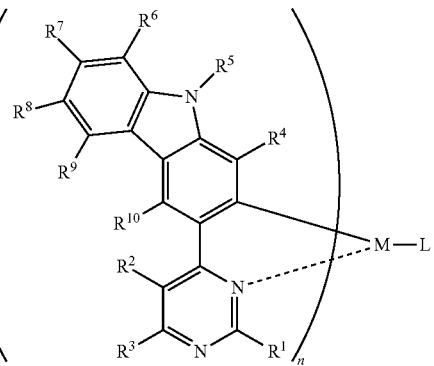

(G1-3)

In General Formula (G1-3), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 2 when M is a Group 9 element, and n is 1 when M is a Group 10 element. In addition, L represents a monoanionic ligand.

In the above-described structure, the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

In addition, in the above-described structure, the monoanionic ligand is preferably a ligand represented by any of General Formulae (L1) to (L7).

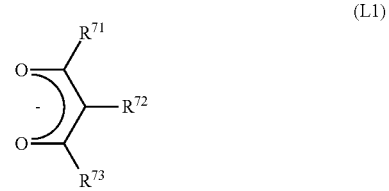

(L1)

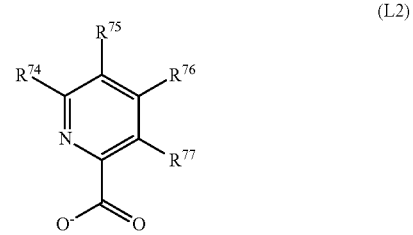

(L2)

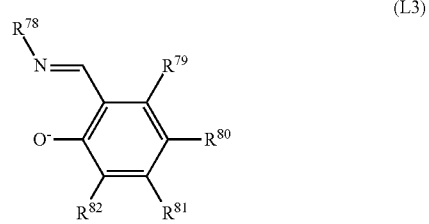

(L3)

-continued

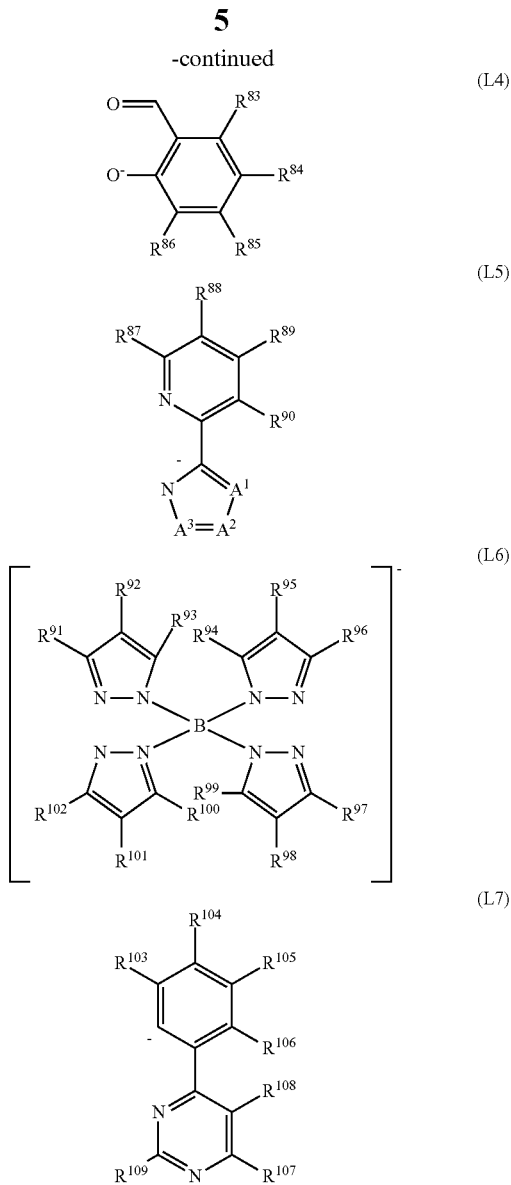

In General Formulae (L1) to (L7), $R^{71}$ to $R^{109}$ separately represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. In addition, $A^1$ to $A^3$ separately represent nitrogen or carbon bonded to hydrogen or a substituent R. The substituent R represents any of an alkyl group having 1 to 6 carbon atoms, a halogen group, a haloalkyl group having 1 to 6 carbon atoms, and a phenyl group.

Note that in each of the organometallic complexes represented by General Formulae (G1-1) to (G1-3), the Group 9 element or the Group 10 element and the ligand have a metal-carbon bond, so that charge is easily transferred to the pyrimidine ring that is the ligand (i.e., metal to ligand charge transfer (MLCT) transition easily occurs). The MLCT transition easily occurs as described above, so that a forbidden transition such as phosphorescence easily occurs, the triplet excitation lifetime is shortened, and the emission efficiency of the organometallic complex can be increased.

A light-emitting device, an electronic appliance, and a lighting device each of which includes the above-described light-emitting element are also included in the scope of the present invention. Note that the light-emitting device in this specification includes, in its category, an image display device and a light source. The light-emitting device includes the following modules in its category: a module in which a connector, such as a flexible printed circuit (FPC), a tape automated bonding (TAB) tape, or a tape carrier package (TCP), is attached to a panel, a module in which a printed wiring board is provided at the end of a TCP, and a module in which an integrated circuit (IC) is directly mounted on a light-emitting element by a chip-on-glass (COG) method.

According to one embodiment of the present invention, a light-emitting element that includes a phosphorescent organometallic complex can be provided. According to one embodiment of the present invention, an organometallic complex that exhibits phosphorescence in the yellow green to orange wavelength range and has high emission efficiency and high reliability can also be provided.

BRIEF DESCRIPTION OF THE DRAWINGS

FIGS. 7A1, 7A2, and 7A3, and FIG. 7B illustrate electronic appliances of one embodiment of the present invention.

DETAILED DESCRIPTION OF THE INVENTION

Hereinafter, embodiments the present invention will be described in detail with reference to the accompanying drawings. Note that the present invention is not limited to the description below, and it is easily understood by those skilled in the art that various changes and modifications can be made without departing from the spirit and scope of the present invention. Therefore, the present invention should not be construed as being limited to the description in the following embodiments.

Embodiment 1

In this embodiment, a light-emitting element that includes, between a pair of electrodes, an EL layer containing an organometallic complex is described with reference to FIG. 1.

Figure 1:
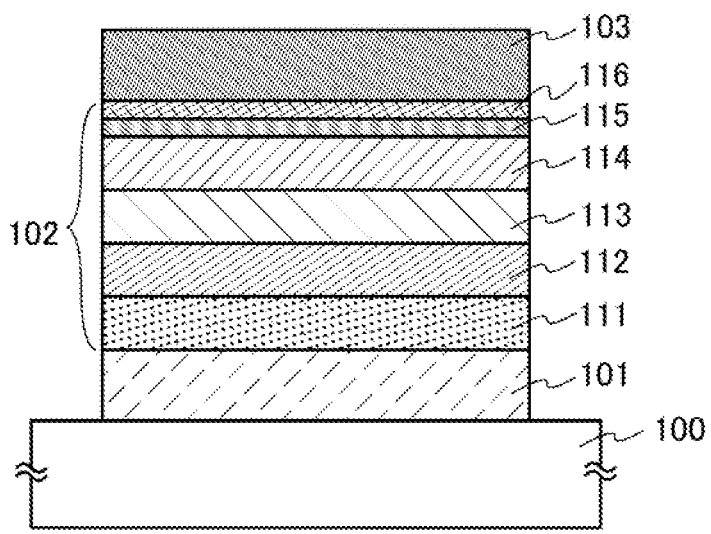
FIG. 1 illustrates a light-emitting element of one embodiment of the present invention.

In a light-emitting element described in this embodiment, as illustrated in FIG. 1, an EL layer 102 including a light-emitting layer 113 is provided between a pair of electrodes (a first electrode 101 and a second electrode 103), and the EL layer 102 includes a hole-injection layer 111, a hole-transport layer 112, an electron-transport layer 114, an electron-injection layer 115, a charge-generation layer 116, and the like in addition to the light-emitting layer 113. Note that in this embodiment, the first electrode 101 is used as an anode and the second electrode 103 is used as a cathode. The first electrode 101 is formed over a substrate 100. The light-emitting layer 113 contains an organometallic complex of one embodiment of the present invention.

By application of voltage to such a light-emitting element, holes injected from the first electrode 101 side and electrons injected from the second electrode 103 side are recombined in the light-emitting layer 113 to raise the organometallic complex contained in the light-emitting layer 113 to an excited state. Then, light is emitted when the organometallic complex in the excited state returns to the ground state. Thus, the organometallic complex of one embodiment of the present invention functions as a light-emitting substance in the light-emitting element.

The hole-injection layer 111 included in the EL layer 102 contains a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge-generation layer 116 is a layer containing a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114. Note that the light-emitting element that includes the charge-generation layer 116 is illustrated in FIG. 1 as an example; however, one embodiment of the present invention is not limited thereto. For example, the light-emitting element does not necessarily include the charge-generation layer 116.

A specific example in which the light-emitting element described in this embodiment is manufactured is described.

The substrate 100 is used as a support of the light-emitting element. For example, glass, quartz, plastic, or the like can be used for the substrate 100. Alternatively, a flexible substrate may be used. A flexible substrate is a substrate that can be bent (is flexible); examples of the flexible substrate include plastic substrates made of a polycarbonate, a polyarylate, and a polyethersulfone. A film (made of polypropylene, a polyester, poly(vinyl fluoride), poly(vinyl chloride), or the like), an inorganic film formed by evaporation, or the like can also be used. Note that another material may be used as long as it can function as a support in a process of manufacturing the light-emitting element.

As the first electrode 101 and the second electrode 103, a metal, an alloy, an electrically conductive compound, a mixture thereof, and the like can be used. Specific examples include indium oxide-tin oxide (ITO: indium tin oxide), indium oxide-tin oxide containing silicon or silicon oxide, indium oxide-zinc oxide, indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti). In addition, any of the following materials can be used: elements that belong to Group 1 or Group 2 of the periodic table, that is, alkali metals such as lithium (Li) and cesium (Cs) or alkaline earth metals such as calcium (Ca) and strontium (Sr), magnesium (Mg), and alloys containing at least one of the metal (e.g., Mg—Ag and Al—Li); rare earth metals such as europium (Eu) and ytterbium (Yb), and alloys containing at least one of the metal; and graphene. The first electrode 101 and the second electrode 103 can be formed by, for example, a sputtering method, an evaporation method (including a vacuum evaporation method), or the like.

As a substance having a high hole-transport property that is used for the hole-injection layer 111, the hole-transport layer 112, and the charge-generation layer 116, for example, a π-electron rich heteroaromatic compound (e.g., a carbazole derivative or an indole derivative) or an aromatic amine compound is preferable. For example, the following substances can be given: compounds having aromatic amine skeletons, such as 4,4'-bis[N-(1-naphthyl)-N-phenylamino] biphenyl (abbreviation: NPB), N,N'-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having thiophene skeletons, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage.

Furthermore, as the substance having a high hole-transport property that is used for the hole-injection layer 111, the hole-transport layer 112, and the charge-generation layer 116, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Furthermore, as the substance that is used for the hole-injection layer 111, the hole-transport layer 112, and the charge-generation layer 116, a layer in which any of the substances having a high hole-transport property given above and a substance having an acceptor property are mixed is preferably used, in which case a favorable carrier-injection property is obtained. Examples of the acceptor substance to be used include oxides of transition metals such as oxides of metals belonging to Groups 4 to 8 of the periodic table. Specifically, molybdenum oxide is particularly preferable.

In the light-emitting layer 113, the organometallic complex of one embodiment of the present invention that serves as a light-emitting substance is contained as a guest material, and a substance having triplet excited energy higher than that of the organometallic complex is used as a host material.

The light-emitting layer 113 may contain an assist material as well as the guest material and the host material. As the guest material, the host material, and the assist material, for example, the organometallic complex of one embodiment of the present invention, an electron-transport material, and a hole-transport material can be used, respectively.

As the electron-transport material that can be used as a host material in the light-emitting layer 113, a π-electron deficient heteroaromatic compound such as a nitrogen-containing heteroaromatic compound is preferable; for example, the following can be given: heterocyclic compounds (e.g., an oxadiazole derivative, an imidazole derivative, and a triazole derivative) having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds (e.g., a pyrazine derivative, a pyrimidine derivative, a pyridazine derivative, a quinoxaline derivative, and a dibenzoquinoxaline derivative) having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds (e.g., a pyridine derivative, a quinoline derivative, and a dibenzoquinoline derivative) having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in drive voltage.

As the hole-transport material that can be used as an assist material in the light-emitting layer 113, any of the substances having high hole-transport properties that can be used for the hole-injection layer 111, the hole-transport layer 112, and the charge-generation layer 116 may be used.

Note that it is preferable that the electron-transport material and the hole-transport material do not have an absorption spectrum in the blue wavelength range. Specifically, an absorption edge of the absorption spectrum is preferably at 440 nm or less.

The organometallic complex of one embodiment of the present invention that is used as the guest material in the light-emitting layer 113 is specifically described below.

One embodiment of the present invention is an organometallic complex in which nitrogen at the 3-position of a pyrimidine ring is coordinated to a metal, a carbazole skeleton is bonded to the 4-position of the pyrimidine ring, and the carbazole skeleton is bonded to the metal.

It is preferable that the metal in the above-described structure be a Group 9 element or a Group 10 element. It is preferable that the metal is selected from iridium, platinum, palladium, and rhodium. It is particularly preferable that the Group 9 element or the Group 10 element be iridium.

That is, the organometallic complex of one embodiment of the present invention has a structure represented by General Formula (G1-1).

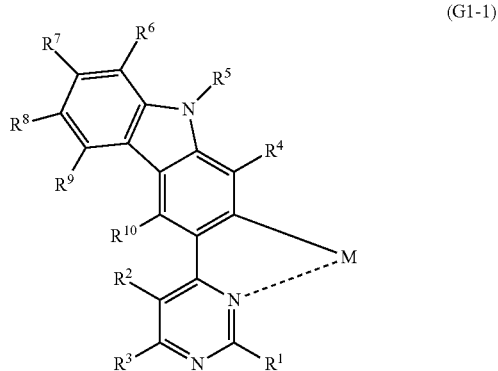

(G1-1)

In General Formula (G1-1), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element.

The organometallic complex that has the structure represented by General Formula (G1-1) is specifically represented by General Formula (G1-2) and/or General Formula (G1-3). Note that the organometallic complex that have the structure represented by General Formula (G1-1) and the organometallic complexes that has the structures represented by General Formula (G1-2) and General Formula (G1-3) are each an organometallic complex of one embodiment of the present invention.

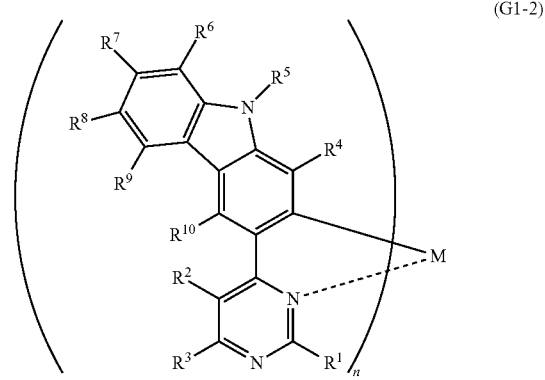

(G1-2)

In General Formula (G1-2), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 3 when M is a Group 9 element, and n is 2 when M is a Group 10 element.

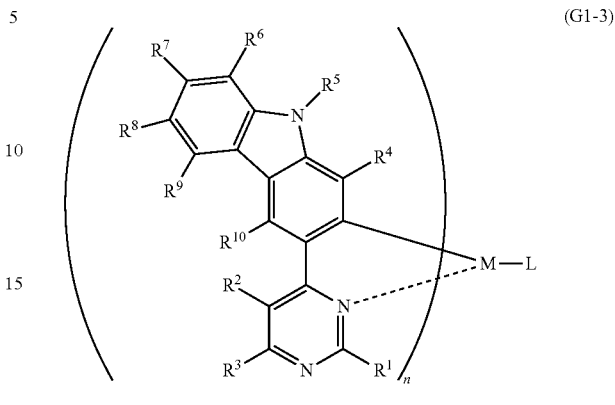

(G1-3)

In General Formula (G1-3), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 2 when M is a Group 9 element, and n is 1 when M is a Group 10 element. In addition, L represents a monoanionic ligand.

Note that in each of the organometallic complexes represented by General Formulae (G1-1) to (G1-3), the Group 9 element or the Group 10 element and a ligand have a metal-carbon bond, so that charge is easily transferred to the pyrimidine ring that is the ligand (i.e., MLCT transition easily occurs). The MLCT transition easily occurs as described above, so that a forbidden transition such as phosphorescence, easily occurs, the triplet excitation lifetime is shortened, and the emission efficiency of the organometallic complex can be increased.

The organometallic complexes represented by General Formulae (G1-1) to (G1-3) each have a bulky structure because of orthometalation by coordination of a metal ion of the Group 9 element or a metal ion of the Group 10 element to the pyrimidine ring, and thus can suppress concentration quenching.

In each of the organometallic complexes represented by General Formulae (G1-1) to (G1-3), a substituent having a carbazole skeleton is bonded to the 4-position of the pyrimidine ring. Since the carbazole skeleton with an excellent hole-trapping property is thus bonded to the nitrogen-containing aromatic ring that influences the HOMO of the MLCT transition in the ortho-metalated complex, an electrically stable substance as an EL material can be obtained.

Note that the monoanionic ligand (L) in General Formula (G1-3) is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a beta-diketone structure is particularly preferable. A beta-diketone structure is preferably included for higher solubility of an organometallic complex in an organic solvent and easier purification. A beta-diketone structure is preferably included for realization of an organometallic complex with high emission efficiency. Furthermore, inclusion of a beta-diketone structure has advantages such as a higher sublimation property and excellent evaporativity.

The monoanionic ligand (L) in General Formula (G1-3) is preferably any of ligands represented by General Formulae (L1) to (L7). These ligands have high coordinative ability and can be obtained at low price, and are thus useful.

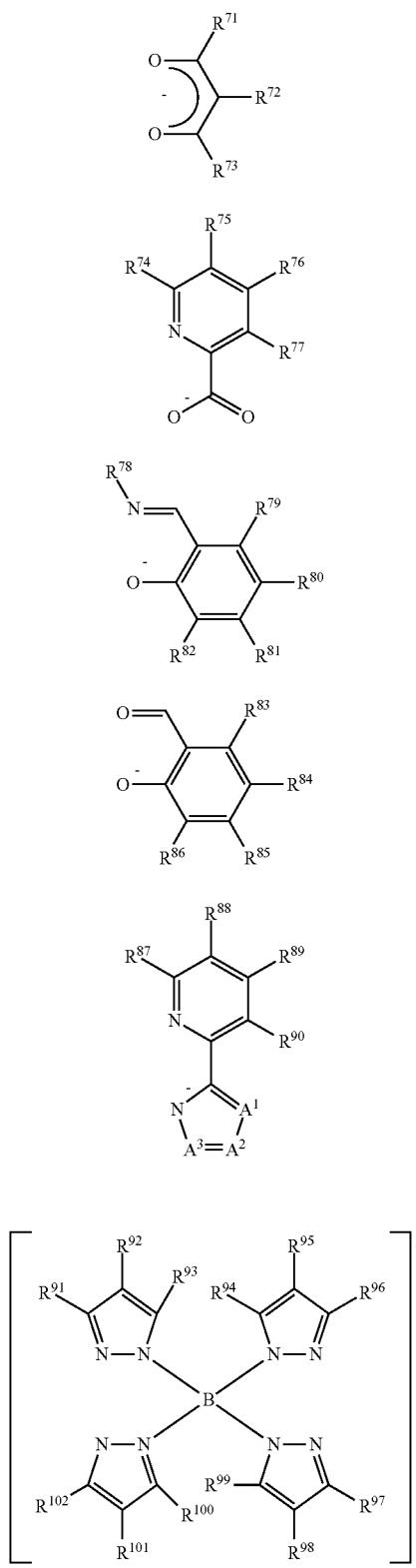

(L1)
(L2)
(L3)
(L4)
(L5)
(L6)

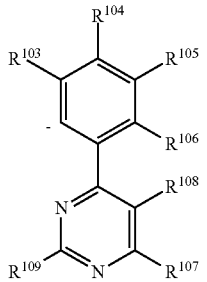

(L7)

In General Formulae (L1) to (L7), $R^{71}$ to $R^{109}$ separately represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. In addition, $A^1$ to $A^3$ separately represent nitrogen or carbon bonded to hydrogen or a substituent R. The substituent R represents any of an alkyl group having 1 to 6 carbon atoms, a halogen group, a haloalkyl group having 1 to 6 carbon atoms, and a phenyl group.

Examples of the organometallic complexes represented by any of General Formulae (G1-1) to (G1-3) include organometallic complexes represented by Structural Formulae (100) to (117). However, one embodiment of the present invention is not limited to these examples.

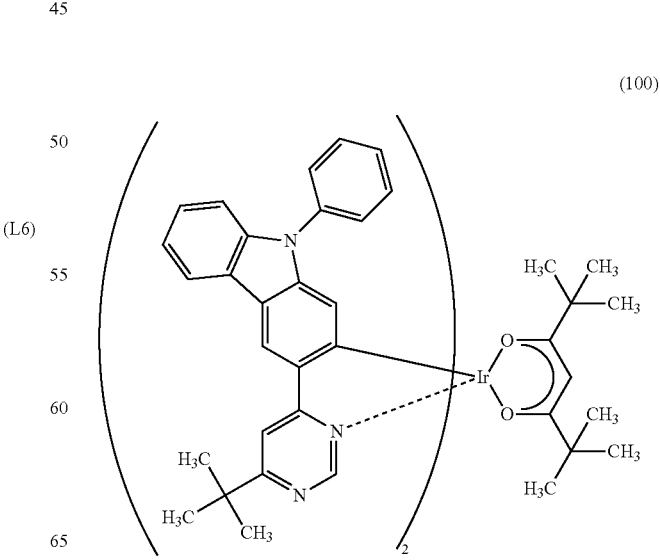

(100)

(101)
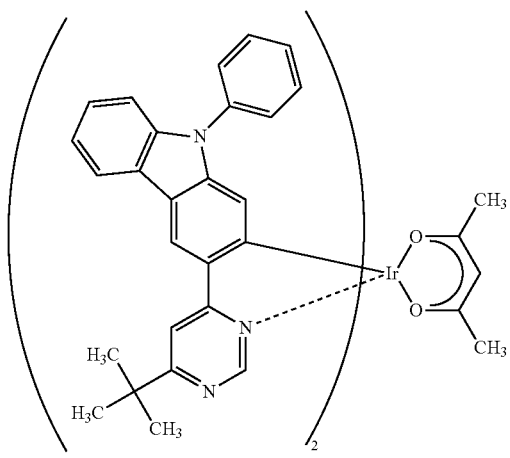
(102)
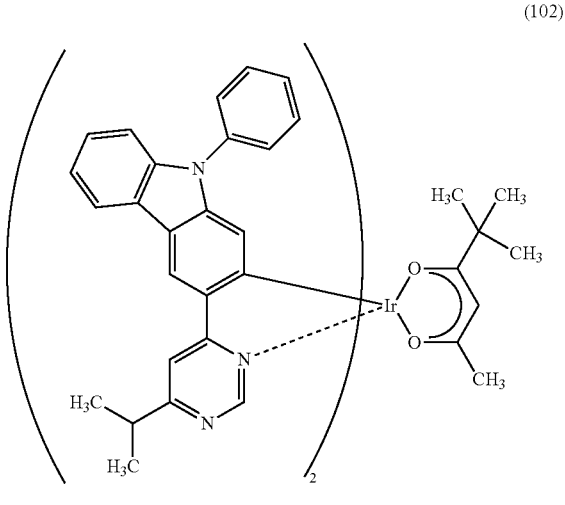
(103)
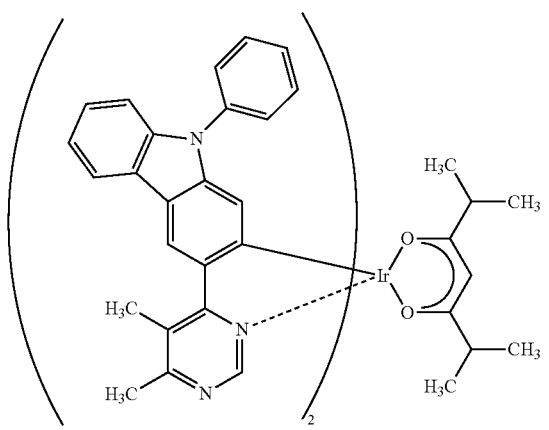
(104)
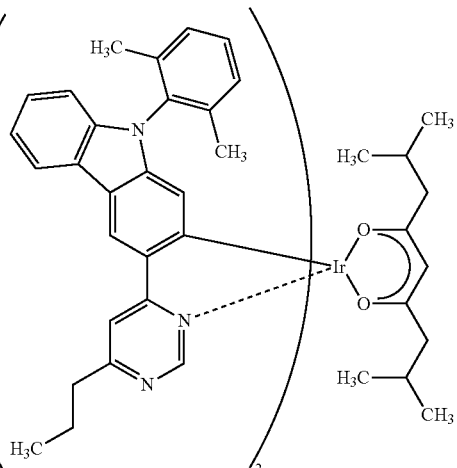
(105)
(106)
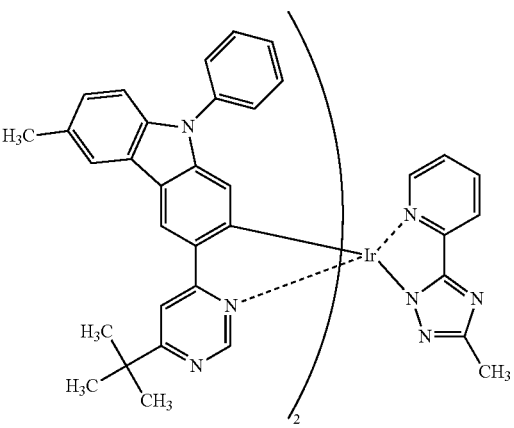

(107)
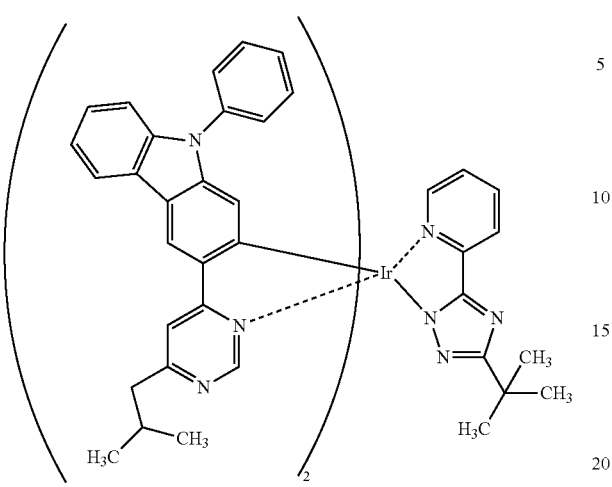
(108)
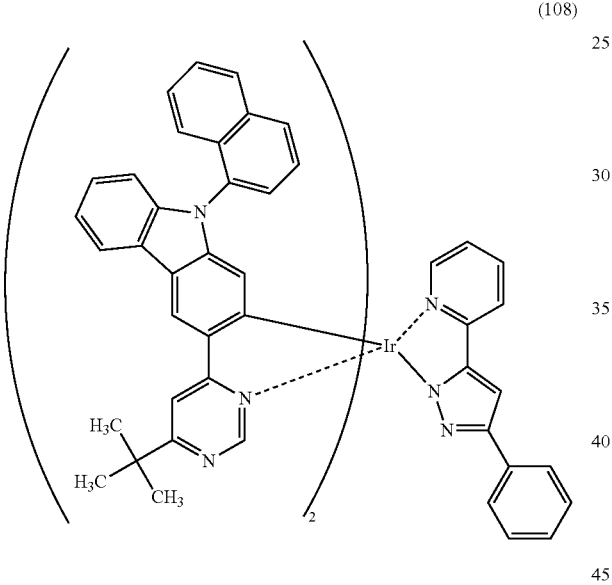
(109)
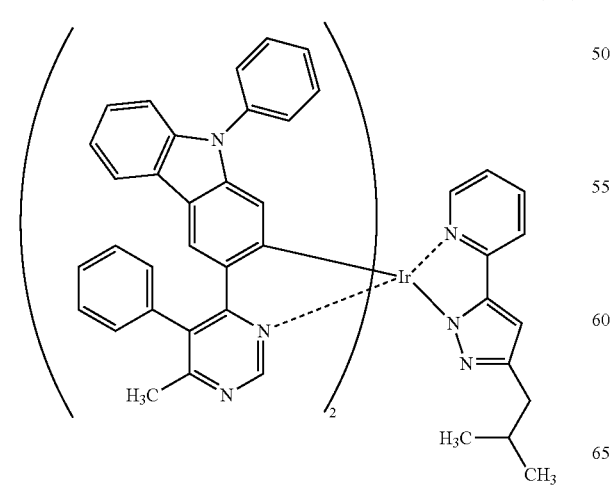
(110)
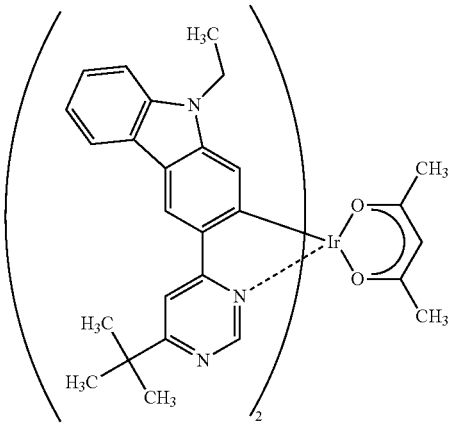
(111)
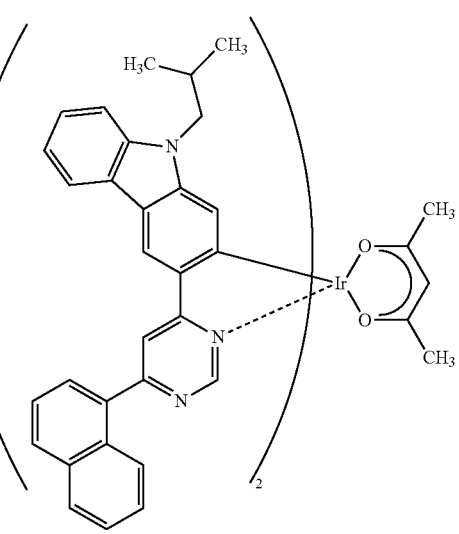
(112)
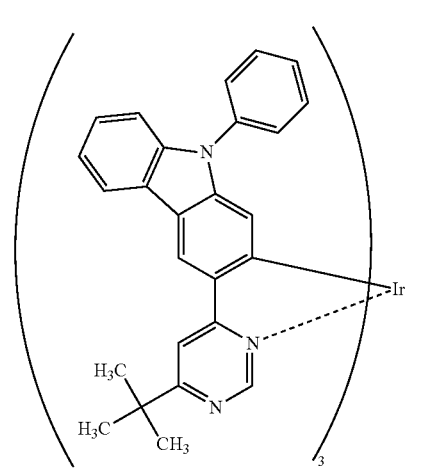

(113)
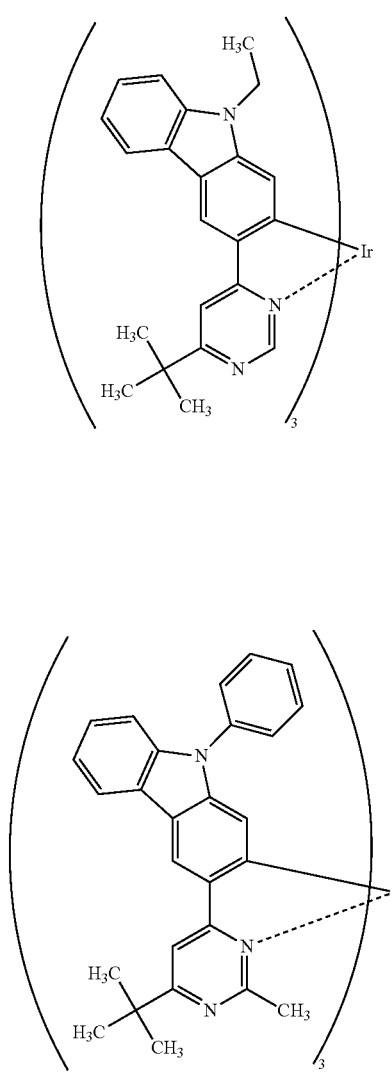

(114)

(115)

(116)
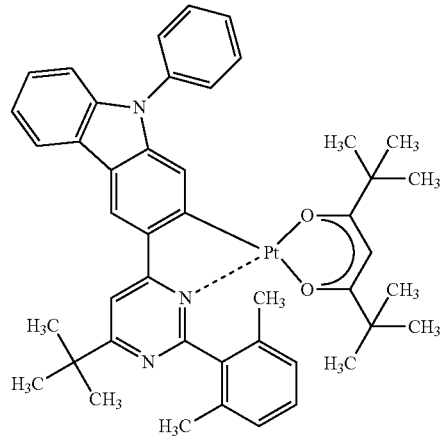

(117)
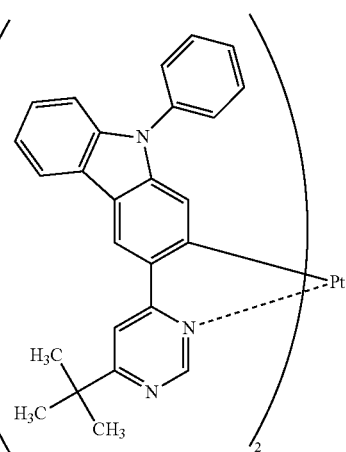

A variety of reactions can be applied to a method of synthesizing any of the organometallic complexes of one embodiment of the present invention. A method of synthesizing an organometallic complex having a structure represented by General Formula (G0) and a method of synthesizing the organometallic complex having the structure represented by General Formula (G1-2) are described below.

<<Method of Synthesizing Carbazol-3-Yl-Pyrimidine Derivative Represented by General Formula (G0)>>

A carbazol-3-yl-pyrimidine derivative represented by General Formula (G0) can be synthesized by simple Synthesis Scheme (a-1) or (a-2) shown below.

(G0)
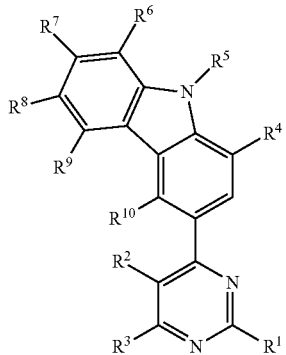

In General Formula (G0), $R^1$ to $R^{10}$ separately represent any of hydrogen, an alkyl group having 1 to 6 carbon atoms, and a substituted or unsubstituted aryl group having 6 to 10 carbon atoms.

For example, as shown in Synthesis Scheme (a-1), a carbazol-3-yl-boronic acid compound (A1) is coupled with a halogenated pyrimidine compound (A2), whereby the carbazol-3-yl-pyrimidine derivative represented by General Formula (G0) is obtained.

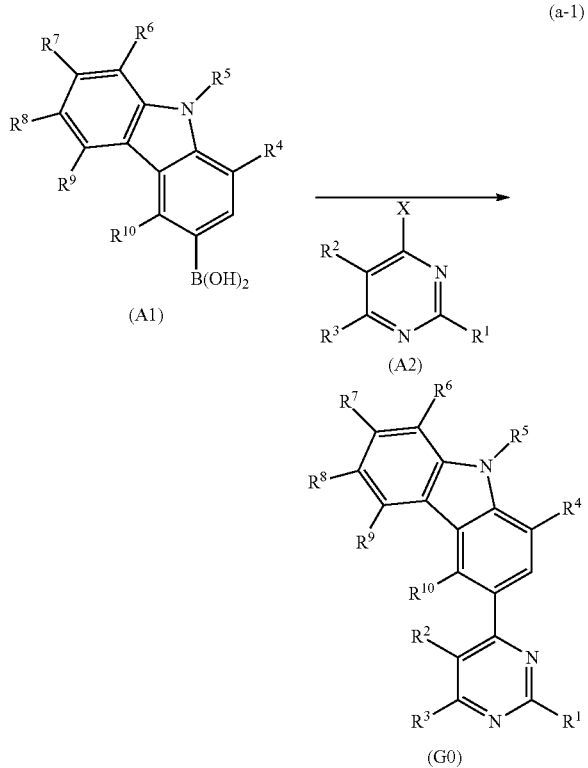

(a-1)

In Synthesis Scheme (a-1), X represents a halogen, and $R^1$ to $R^{10}$ separately represent any of hydrogen, an alkyl group having 1 to 6 carbon atoms, and a substituted or unsubstituted aryl group having 6 to 10 carbon atoms.

Alternatively, as shown in Synthesis Scheme (a-2), a 1,3-diketone (A3) of carbazole is reacted with amidine (A4), whereby the carbazol-3-yl-pyrimidine derivative represented by General Formula (G0) is obtained.

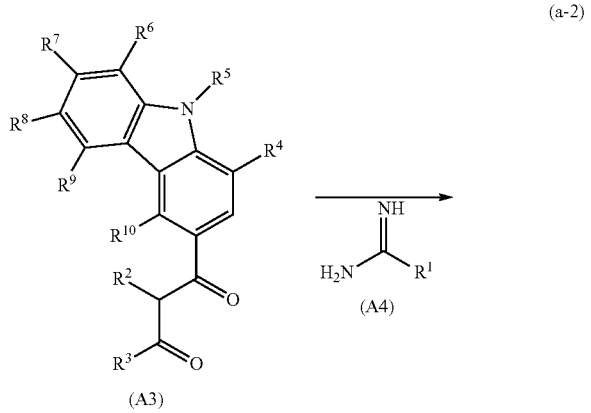

(a-2)

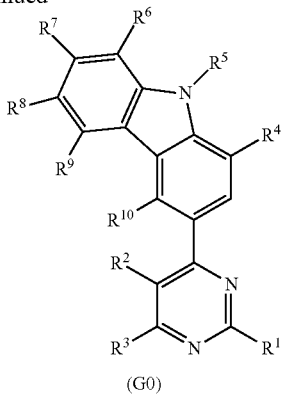

(G0)

In Synthesis Scheme (a-2), $R^1$ to $R^{10}$ separately represent any of hydrogen, an alkyl group having 1 to 6 carbon atoms, and a substituted or unsubstituted aryl group having 6 to 10 carbon atoms.

Note that in the case where $R^1$ is hydrogen in General Formula (G0), as disclosed in Non-Patent Document (H. Bredereck, R. Gompper, G Morlock, "Chemische Berichte," 90, p. 942 (1957)), a 1,3-diketone (A3) of carbazole is reacted with formamide under heating in the presence of an acid catalyst, whereby the carbazol-3-yl-pyrimidine derivative represented by General Formula (G0) is obtained.

Since a wide variety of compounds (A1) to (A4) are commercially available or their synthesis is feasible, a great variety of the carbazol-3-yl-pyrimidine derivatives represented by General Formula (G0) can be synthesized. Thus, the organometallic complex of one embodiment of the present invention has a wide variety of ligands.

<<Method of Synthesizing Organometallic Complex of One Embodiment of the Present Invention Represented by General Formula (G1-2)>>

As shown in Synthesis Scheme (b), by mixing the carbazol-3-yl-pyrimdine derivative represented by General Formula (G0) is mixed with a compound of a Group 9 metal or a Group 10 metal (e.g., rhodium chloride hydrate, palladium chloride, iridium chloride hydrate, ammonium hexachloroiridate, or potassium tetrachloroplatinate) or an organometallic complex compound of a Group 9 metal or a Group 10 metal (e.g., an acetylacetonate complex or a diethylsulfide complex), and the mixture is then heated, whereby the organometallic complex having the structure represented by General Formula (G1-2) can be obtained. This heating process may be performed after the carbazol-3-yl-pyrimdine derivative represented by General Formula (G0) and the compound of a Group 9 metal or a Group 10 metal that contains a halogen or the organometallic complex compound of a Group 9 metal or a Group 10 metal are dissolved in an alcohol-based solvent (e.g., glycerol, ethylene glycol, 2-methoxyethanol, or 2-ethoxyethanol).

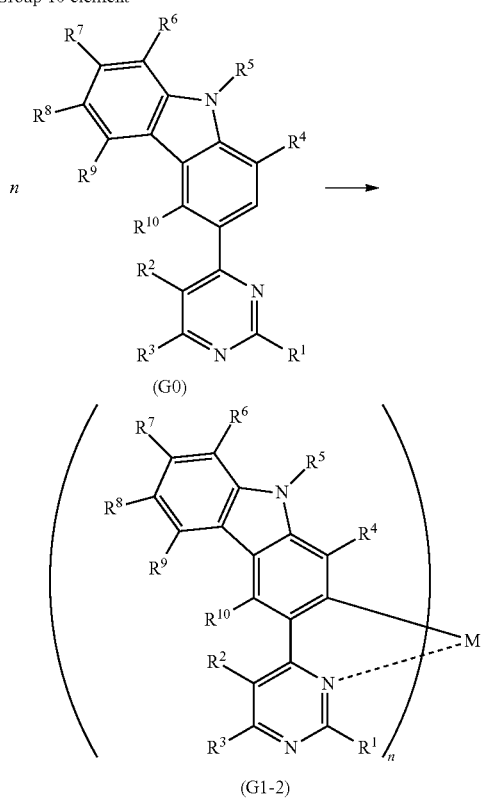

(G0)

(G1-2)

In Synthesis Scheme (b), $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 3 when M is a Group 9 element, and n is 2 when M is a Group 10 element.

In addition, in one embodiment of the present invention, a substituent is preferably bonded to the 6-position (i.e., $R^3$) of pyrimidine in order to obtain an ortho-metalated complex in which the carbazol-3-yl-pyrimdine derivative is a ligand. In particular, a substituted or unsubstituted alkyl group having 1 to 6 carbon atoms or a substituted or unsubstituted aryl group having 6 to 10 carbon atoms is used as $R^3$. Therefore, as compared to the case where hydrogen is used as $R^3$, the yield in Synthesis Scheme (b) can be higher.

<<Method of Synthesizing Organometallic Complex of One Embodiment of the Present Invention Represented by General Formula (G1-3)>>

As shown in Synthesis Scheme (c-1), the carbazol-3-yl-pyrimidine derivative represented by General Formula (G0) and a metal compound that contains halogen (e.g., palladium chloride, iridium chloride, iridium bromide, iridium iodide, or potassium tetrachloroplatinate) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more kinds of such alcohol-based solvents, whereby a dinuclear complex (P), which is one type of an organometallic complex having a halogen-bridged structure and is a novel substance, can be obtained. There is no particular limitation on a heating means, and an oil bath, a sand bath, or an aluminum block may be used. Alternatively, microwaves can be used as a heating means.

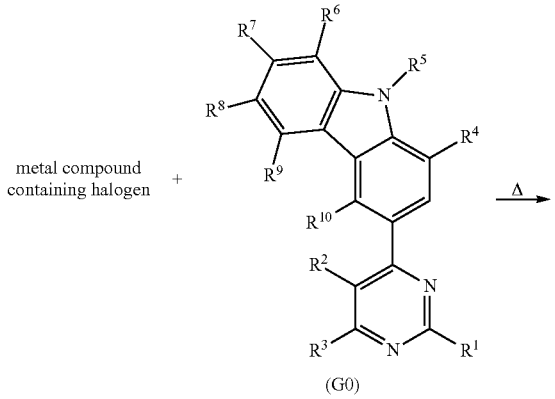

(G0)

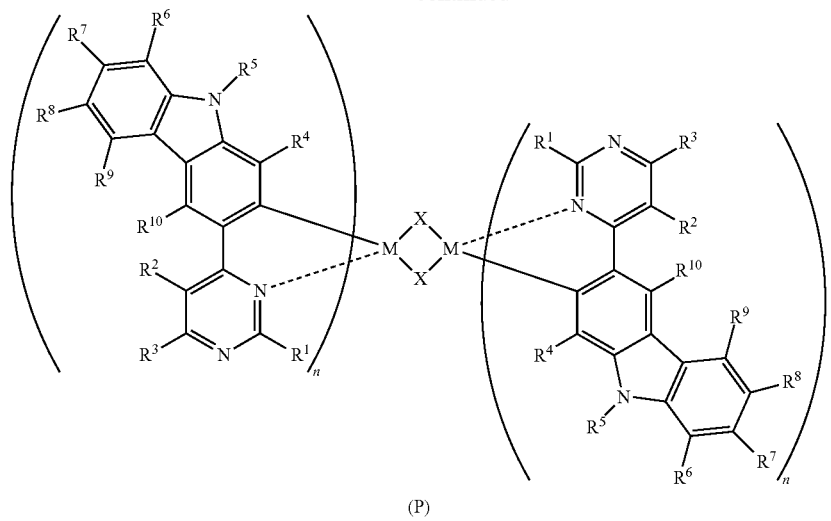

(P)

In Synthesis Scheme (c-1), X represents a halogen, and $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 2 when M is a Group 9 element, and n is 1 when M is a Group 10 element.

Furthermore, as shown in Synthesis Scheme (c-2), the dinuclear complex (P) obtained in Synthesis Scheme (c-1) is reacted with HL that is a material of a monoanionic ligand in an inert gas atmosphere, whereby a proton of HL is separated and L coordinates to the central metal M. Thus, the organometallic complex represented by General Formula (G1-3) of one embodiment of the present invention can be obtained. There is no particular limitation on a heating means, and an oil bath, a sand bath, or an aluminum block may be used. Alternatively, microwaves can be used as a heating means.

(c-2)

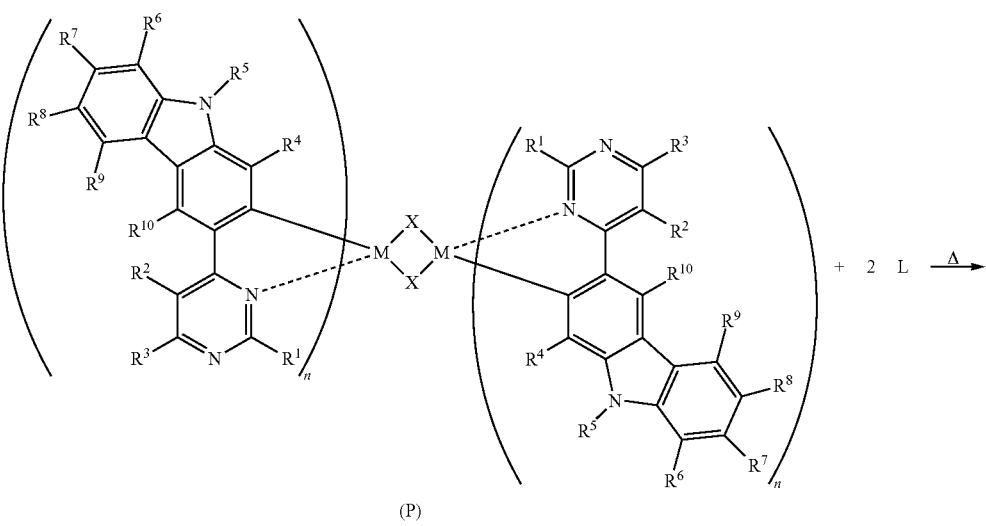

(P)

-continued

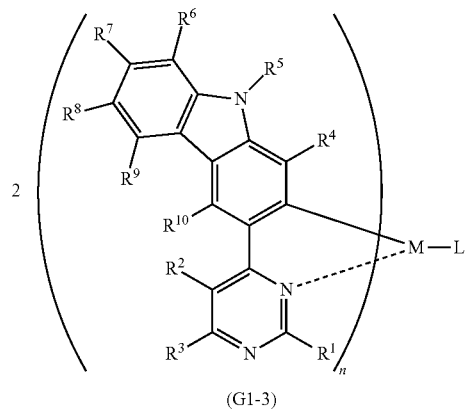

(G1-3)

In Synthesis Scheme (c-2), L represents a monoanionic ligand, X represents a halogen, and $R^1$ to $R^{10}$ separately represent any of hydrogen, an alkyl group having 1 to 6 carbon atoms, and a substituted or unsubstituted aryl group having 6 to 10 carbon atoms. In addition, M represents a Group 9 element or a Group 10 element. In addition, n is 2 when M is a Group 9 element, and n is 1 when M is a Group 10 element.

As described above, in one embodiment of the present invention, a substituent is bonded to the 4-position of the pyrimidine ring in order to obtain an ortho-metalated complex in which the pyrimidine derivative is a ligand. In particular, a carbazole skeleton is used as the substituent. Thus, as compared to the case where hydrogen is used as the substituent bonded to the 4-position of the pyrimidine ring, decomposition of the halogen-bridged dinuclear metal complex synthesized in Synthesis Scheme (c-1) is suppressed during reaction represented by Synthesis Scheme (c-2), and a drastically high yield can be obtained.

Through the above-described steps, the organometallic complexes in this embodiment can be synthesized.

Note that in the case where the light-emitting layer 113 contains a host material and a guest material that is any of the above-described organometallic complexes, phosphorescence with high emission efficiency can be obtained from the light-emitting layer 113.

In the above-described manner, the light-emitting layer 113 can be formed.

The electron-transport layer 114 provided over the light-emitting layer 113 is a layer containing a substance having a high electron-transport property. For the electron-transport layer 114, a metal complex such as Alq$_3$, tris(4-methyl-8-quinolinolato)aluminum (abbreviation: Almq$_3$), bis(10-hydroxybenzo[h]quinolinato)beryllium(II) (abbreviation: BeBq$_2$), BAlq, Zn(BOX)$_2$, or bis[2-(2-hydroxyphenyl)benzothiazolato]zinc(II) (abbreviation: Zn(BTZ)$_2$) can be used. A heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can also be used. A high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can also be used. The substances given here are mainly ones that have an electron mobility of $10^{-6}$ cm$^2$/Vs. Note that any substance other than the above substances may be used as long as the electron-transport property is higher than the hole-transport property.

The electron-transport layer 114 is not limited to a single layer, but may be a stack of two or more layers containing any of the above substances.

The electron-injection layer 115 contains a substance having a high electron-injection property. For the electron-injection layer 115, an alkali metal, an alkaline earth metal, or a compound thereof, such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. The substances for forming the electron-transport layer 114, which are given above, can also be used.

Alternatively, for the electron-injection layer 115, a composite material in which an organic compound and an electron donor (donor) are mixed may be used. Such a composite material is excellent in an electron-injection property and an electron-transport property because electrons are generated in the organic compound by the electron donor. In this case, the organic compound is preferably a material that is excellent in transporting the generated electrons. Specifically, for example, any of the above substances for forming the electron-transport layer 114 (e.g., a metal complex or a heteroaromatic compound) can be used. As the electron donor, a substance exhibiting an electron-donating property with respect to the organic compound may be used. Specific examples are an alkali metal, an alkaline earth metal, and a rare earth metal are preferable, and lithium, cesium, magnesium, calcium, erbium, and ytterbium. In addition, an alkali metal oxide or an alkaline earth metal oxide is preferable, examples of which are lithium oxide, calcium oxide, and barium oxide. Lewis base such as magnesium oxide can also be used. An organic compound such as tetrathiafulvalene (abbreviation: TTF) can also be used.

Note that each of the above-described hole-injection layer 111, hole-transport layer 112, light-emitting layer 113, electron-transport layer 114, electron-injection layer 115, and charge-generation layer 116 can be formed by a method such as an evaporation method (e.g., a vacuum evaporation method), an inkjet method, or a coating method.

In the above-described light-emitting element, current flows because of a potential difference generated between the first electrode 101 and the second electrode 103 and holes and electrons are recombined in the EL layer 102, whereby light is emitted. This emitted light is extracted outside through one or both of the first electrode 101 and the second electrode 103. Therefore, one or both of the first electrode 101 and the second electrode 103 are electrodes having light-transmitting properties.

The above-described light-emitting element can emit phosphorescence originating from the organometallic complex, and thus can have higher efficiency than a light-emitting element using a fluorescent compound.

Note that the structure described in this embodiment can be combined as appropriate with any of the structures described in the other embodiments.

Embodiment 2

In this embodiment, a light-emitting element that includes, between a pair of electrodes, an EL layer including a light-emitting layer containing an organometallic complex of one embodiment of the present invention and two or more kinds of organic compounds is described with reference to FIG. 2.

Figure 2:
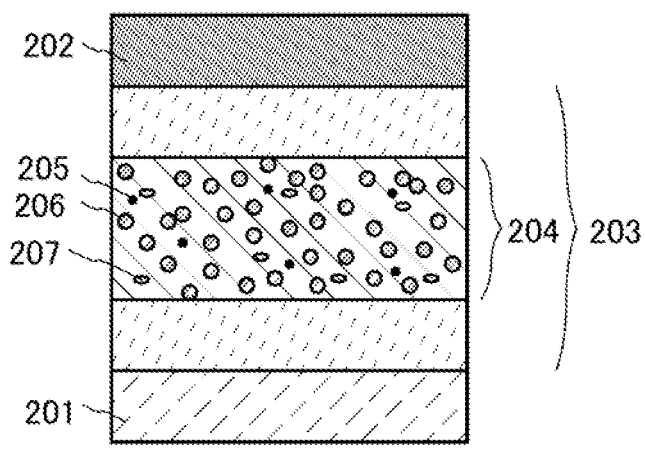
FIG. 2 illustrates a light-emitting element of one embodiment of the present invention.

A light-emitting element described in this embodiment includes an EL layer 203 between a pair of electrodes (a first electrode 201 and a second electrode 202) as illustrated in FIG. 2. Note that the EL layer 203 includes at least a light-emitting layer 204 and may include a hole-injection layer, a hole-transport layer, an electron-transport layer, an electron-injection layer, a charge-generation layer, and the like. Note that in FIG. 2, the above-described hole-injection layer, hole-transport layer, electron-transport layer, electron-injection layer, and charge-generation layer, and the like can be provided as appropriate between the first electrode 201 and the EL layer 203 and between the second electrode 202 and the EL layer 203. The substances given in Embodiment 1 can be used for the hole-injection layer, the hole-transport layer, the electron-transport layer, the electron-injection layer, and the charge-generation layer. Note that the first electrode 201 is used as an anode and the second electrode 202 is used as a cathode in this embodiment.

The light-emitting layer 204 described in this embodiment contains a phosphorescent compound 205 using the organometallic complex of one embodiment of the present invention, which is described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. In addition, it is possible to suppress concentration quenching due to high concentration of the guest material, and thus the light-emitting element can have higher emission efficiency.

Note that it is preferable that the triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency is decreased.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) largely overlap with an absorption spectrum of a guest material (specifically, spectrum in an absorption band on the longest wavelength (lowest energy) side). However, in the case of a general phosphorescent guest material, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of the host material.

Thus, in this embodiment, a combination of the first organic compound 206 and the second organic compound 207 preferably forms an exciplex. In this case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex that is located on a longer wavelength side. Moreover, when the first organic compound and the second organic compound are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

For the phosphorescent compound 205, any of the organometallic complexes of one embodiment of the present invention, which are described in Embodiment 1 is used. For the first organic compound 206 and the second organic compound 207, a combination of a compound that easily accepts electrons (a compound having an electron-trapping property) and a compound that easily accepts holes (a compound having a hole-trapping property) is preferably used.

Examples of the compound that easily accepts holes include 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N-diphenylbenzene-1,3-diamine (abbreviation: PCA2B), N-(9,9-dimethyl-2-diphenylamino-9H-fluoren-7-yl)diphenylamine (abbreviation: DPNF), 4-phenyldiphenyl-(9-phenyl-9H-carbazol-3-yl)amine (abbreviation: PCA1BP), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]-spiro-9,9'-bifluorene (abbreviation: PCASF), 2-[N-(4-diphenylaminophenyl)-N-phenylamino]spiro-9,9'-bifluorene (abbreviation: DPASF), N,N-di(biphenyl-4-yl)-N-(9-phenyl-9H-carbazol-3-yl)amine (abbreviation: PCzBBA1), N,N'-bis[4-(carbazol-9-yl)phenyl]-N,N-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

The above-described combination of the first organic compound 206 and the second organic compound 207 is an example of the combination that enables an exciplex to be formed. The combination is determined so that the emission spectrum of the exciplex overlaps with the absorption spectrum of the phosphorescent compound 205 and that the peak of the emission spectrum of the exciplex has a longer wavelength than the peak of the absorption spectrum of the phosphorescent compound 205.

Note that in the case where a compound that easily accepts electrons and a compound that easily accepts holes are used for the first organic compound 206 and the second organic compound 207, carrier balance can be controlled by the mixture ratio of the compounds. Specifically, the weight ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of a light-emitting element.

Note that in another structure of the present invention, the light-emitting layer 204 can be formed using a host material having a hole-trapping property and a host material having an electron-trapping property as the two kinds of organic compounds other than the phosphorescent compound 205 (guest material) so that a phenomenon (guest coupled with complementary hosts: GCCH) occurs in which holes and electrons are introduced to guest materials existing in the two kinds of host materials and the guest materials are brought into an excited state.

At this time, the host material having a hole-trapping property and the host material having an electron-trapping property can be respectively selected from the above-described compounds that easily accept holes and the above-described compounds that easily accept electrons.

Note that the structure described in this embodiment can be combined as appropriate with any of the structures described in the other embodiments.

Embodiment 3

In this embodiment, as one embodiment of the present invention, a light-emitting element (hereinafter referred to as tandem light-emitting element) in which a charge-generation layer is provided between a plurality of EL layers is described.

Figure 3A:
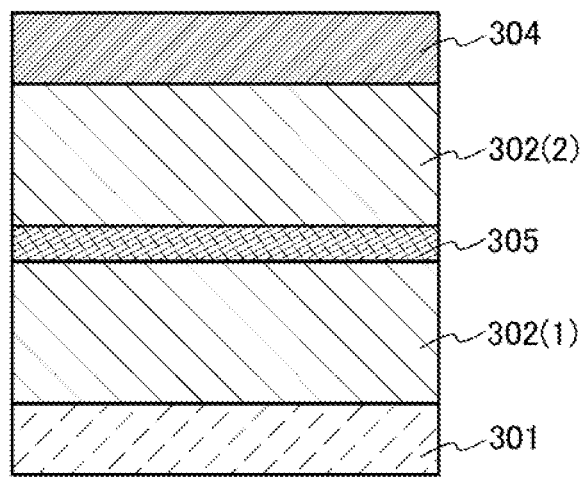
FIGS. 3A and 3B each illustrate a light-emitting element according to one embodiment of the present invention.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 1. In addition, although the plurality of EL layers (the first EL layer 302(1) and the second EL layer 302(2)) may have structures similar to those described in Embodiment 1 or 2, any of the EL layers may have a structure similar to that described in Embodiment 1 or 2. In other words, the structures of the first EL layer 302(1) and the second EL layer 302(2) may be the same or different from each other and can be similar to those described in Embodiment 1 or 2.

In addition, a charge-generation layer 305 is provided between the plurality of EL layers (the first EL layer 302(1) and the second EL layer 302(2)). The charge-generation layer 305 has a function of injecting electrons into one of the EL layers and injecting holes into the other of the EL layers when a voltage is applied to the first electrode 301 and the second electrode 304. In this embodiment, when voltage is applied such that the potential of the first electrode 301 is higher than that of the second electrode 304, the charge-generation layer 305 injects electrons into the first EL layer 302(1) and injects holes into the second EL layer 302(2).

Note that in terms of light extraction efficiency, the charge-generation layer 305 preferably has a light-transmitting property with respect to visible light (specifically, the charge-generation layer 305 has a visible light transmittance of 40% or more). The charge-generation layer 305 functions even if it has lower conductivity than the first electrode 301 or the second electrode 304.

The charge-generation layer 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances given here are mainly ones that have a hole mobility of $10^{-6}$ cm$^2$/Vs or higher. Note that any substance other than the above substances may be used as long as the hole-transport property is higher than the electron-transport property.

As the electron acceptor, 7,7,8,8-tetracyano-2,3,5,6-tetrafluoroquinodimethane (abbreviation: $F_4$-TCNQ), chloranil, and the like can be given. Transition metal oxides can also be given. Oxides of metals belonging to Groups 4 to 8 of the periodic table can also be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these oxides, molybdenum oxide is particularly preferable because it is stable in the air, has a low hygroscopic property, and is easy to handle.

In the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances given here are mainly ones that have an electron mobility of $10^{-6}$ cm$^2$/Vs or higher. The second organic compound having a pyrimidine skeleton may also be used. Note that any substance other than the above substances may be used as long as the electron-transport property is higher than the hole-transport property.

As the electron donor, an alkali metal, an alkaline earth metal, a rare earth metal, a metal belonging to Group 13 of the periodic table, or an oxide or carbonate thereof can be used. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may also be used as the electron donor.

Note that forming the charge-generation layer 305 by using any of the above materials can suppress an increase in driving voltage caused by the stack of the EL layers.

Figure 3B:
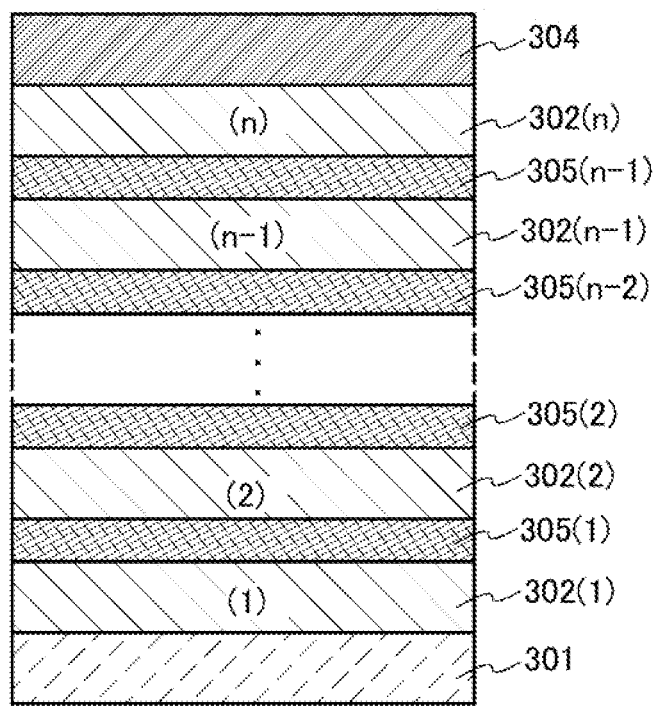

Although the light-emitting element having two EL layers is illustrated in FIG. 3A, the present invention can be similarly applied to a light-emitting element in which n EL layers (n is three or more) are stacked as illustrated in FIG. 3B. In the case where a plurality of EL layers are included between a pair of electrodes as in the light-emitting element of this embodiment, by providing the charge-generation layer between the EL layers, the light-emitting element can emit light in a high luminance region while the current density is kept low. Since the current density can be kept low, the element can have a long lifetime. In addition, when the light emitting element is applied to a lighting system for example, uniform light emission in a large area is possible because voltage drop due to resistance of an electrode material can be decreased. A light-emitting device that can be driven at a low voltage and has low power consumption can be realized.

When the EL layers have different emission colors, a desired emission color can be obtained from the whole light-emitting element. For example, in the light-emitting element having two EL layers, when an emission color of the first EL layer and an emission color of the second EL layer are made to be complementary colors, a light-emitting element emitting white light as a whole light-emitting element can also be obtained. Note that the term "complementary" means color relationship in which an achromatic color is obtained when colors are mixed. That is, white light emission can be obtained by mixture of light emitted from substances whose emission colors are complementary colors.

The same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 4

In this embodiment, a light-emitting device that includes a light-emitting element including an EL layer containing an organometallic complex is described with reference to FIG. 4.

A light-emitting device described in this embodiment has a micro optical resonator (microcavity) structure in which a light resonant effect between a pair of electrodes is utilized. The light-emitting device includes a plurality of light-emitting elements each of which has at least an EL layer 455 between a pair of electrodes (a reflective electrode 451 and a semi-transmissive and semi-reflective electrode 452) as illustrated in FIG. 4. The EL layer 455 may further include at least a first light-emitting layer 454B, a second light-emitting layer 454G, and a third light-emitting layer 454R, each of which serves as a light-emitting region. The EL layer 455 may further include a hole-injection layer, a hole-transport layer, an electron-transport layer, an electron-injection layer, a charge generating layer, and the like. Note that an organometallic complex of one embodiment of the present invention is contained in at least one of the first light-emitting layer 454B, the second light-emitting layer 454G and the third light-emitting layer 454R.

Figure 4:
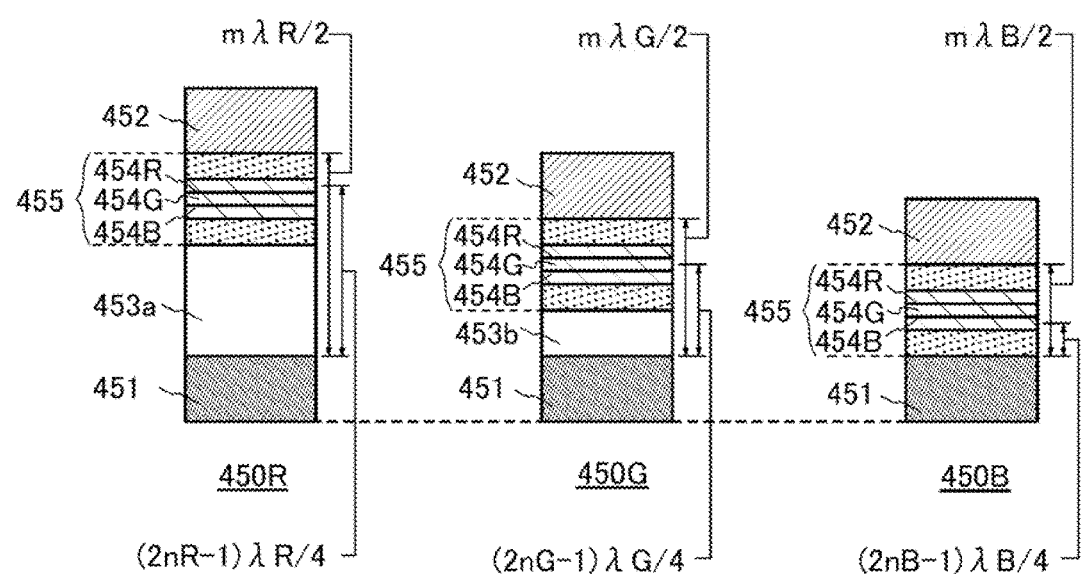
FIG. 4 illustrates light-emitting devices of one embodiment of the present invention.

Described in this embodiment is a light-emitting device that includes light-emitting elements (a first light-emitting element 450R, a second light-emitting element 450G, and a third light-emitting element 450B) that have different structures as illustrated in FIG. 4.

The first light-emitting element 450R has a structure in which a first transparent conductive layer 453a, the EL layer 455, the semi-transmissive and semi-reflective electrode 452 are sequentially stacked over the reflective electrode 451. The second light-emitting element 450G has a structure in which a second transparent conductive layer 453b, the EL layer 455, and the semi-transmissive and semi-reflective electrode 452 are sequentially stacked over the reflective electrode 451. The third light-emitting element 450B has a structure in which the EL layer 455 and the semi-transmissive and semi-reflective electrode 452 are sequentially stacked over the reflective electrode 451.

Note that the reflective electrode 451, the EL layer 455, and the semi-transmissive and semi-reflective electrode 452 are common to the light-emitting elements (the first light-emitting element 450R, the second light-emitting element 450G, and the third light-emitting element 450B).

The EL layer 455 includes the first light-emitting layer 454B, the second light-emitting layer 454G, and the third light-emitting layer 454R. The first light-emitting layer 454B, the second light-emitting layer 454G, and the third light-emitting layer 454R emit a light ($\lambda_B$) having a peak in a wavelength range from 420 nm to 480 nm, a light ($\lambda_G$) having a peak in a wavelength range from 500 nm to 550 nm, and a light ($\lambda_R$) having a peak in a wavelength range from 600 nm to 760 nm, respectively. Thus, in each of the light-emitting elements (the first light-emitting element 450R, the second light-emitting element 450G, and the third light-emitting element 450B), the lights emitted from the first light-emitting layer 454B, the second light-emitting layer 454G, and the third light-emitting layer 454R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 455 is interposed between the reflective electrode 451 and the semi-transmissive and semi-reflective electrode 452. The lights emitted in all directions from the light-emitting layers included in the EL layer 455 are resonated by the reflective electrode 451 and the semi-transmissive and semi-reflective electrode 452 that function as a micro optical resonator (microcavity). Note that the reflective electrode 451 is formed using a conductive material having reflectivity, and a film whose visible light reflectivity is 40% to 100%, preferably 70% to 100%, and whose resistivity is $1 \times 10^{-2}$ $\Omega$cm or lower is used. In addition, the semi-transmissive and semi-reflective electrode 452 is formed using a conductive material having reflectivity and a conductive material having a light-transmitting property, and a film whose visible light reflectivity is 20% to 80%, preferably 40% to 70%, and whose resistivity is $1 \times 10^{-2}$ $\Omega$cm or lower is used.

In this embodiment, the thicknesses of the transparent conductive layers (the first transparent conductive layer 453a and the second transparent conductive layer 453b) provided in the first light-emitting element 450R and the second light-emitting element 450G, respectively, are varied between the light-emitting elements, whereby the light-emitting elements differ in the optical path length from the reflective electrode 451 to the semi-transmissive and semi-reflective electrode 452. In other words, in light having a broad emission spectrum, which is emitted from the light-emitting layers of each of the light-emitting elements, light with a wavelength that is resonated between the reflective electrode 451 and the semi-transmissive and semi-reflective electrode 452 can be enhanced while light with a wavelength that is not resonated therebetween can be attenuated. Thus, when the elements differ in the optical path length from the reflective electrode 451 to the semi-transmissive and semi-reflective electrode 452, light with different wavelengths can be extracted.

Note that the optical path length (also referred to as optical distance) is expressed as a product of an actual distance and a refractive index, and in this embodiment, is a product of an actual thickness and n (refractive index). That is, the following relation is satisfied: optical path length=actual thickness×n (refractive index).

The optical path length from the reflective electrode 451 to the semi-transmissive and semi-reflective electrode 452 is set to m$\lambda_R$/2 (m is a natural number of 1 or more) in the first light-emitting element 450R; the optical path length from the reflective electrode 451 to the semi-transmissive and semi-reflective electrode 452 is set to m$\lambda_G$/2 (m is a natural number of 1 or more) in the second light-emitting element 450G; and the optical path length from the reflective electrode 451 to the semi-transmissive and semi-reflective electrode 452 is set to m$\lambda_B$/2 (m is a natural number of 1 or more) in the third light-emitting element 450B.

In this manner, the light ($\lambda_R$) emitted from the third light-emitting layer 454R included in the EL layer 455 is mainly extracted from the first light-emitting element 450R, the light ($\lambda_G$) emitted from the second light-emitting layer 454G included in the EL layer 455 is mainly extracted from the second light-emitting element 450G, and the light ($\lambda_B$) emitted from the first light-emitting layer 454B included in the EL layer 455 is mainly extracted from the third light-emitting element 450B. Note that the light extracted from each of the light-emitting elements is emitted through the semi-transmissive and semi-reflective electrode 452 side.

Strictly speaking, the optical path length from the reflective electrode 451 to the semi-transmissive and semi-reflective electrode 452 can be the distance from a reflection region in the reflective electrode 451 to a reflection region in the semi-transmissive and semi-reflective electrode 452. However, it is difficult to precisely determine the positions of the reflection regions in the reflective electrode 451 and the semi-transmissive and semi-reflective electrode 452; therefore, it is assumed that the above effect can be sufficiently obtained wherever the reflection regions may be set in the reflective electrode 451 and the semi-transmissive and semi-reflective electrode 452.

Next, the optical path length from the reflective electrode 451 to the third light-emitting layer 454R is adjusted to $(2n_R-1)\lambda_R/4$ ($n_R$ is a natural number of 1 or more) because in the first light-emitting element 450R, light (first reflected light) that is reflected by the reflective electrode 451 of the light emitted from the third light-emitting layer 454R interferes with light (first incident light) that directly enters the semi-transmissive and semi-reflective electrode 452 from the third light-emitting layer 454R. By adjusting the optical path length, the phases of the first reflected light and the first incident light can be aligned with each other and the light emitted from the third light-emitting layer 454R can be amplified.

Note that, strictly speaking, the optical path length from the reflective electrode 451 to the third light-emitting layer 454R can be the optical path length from a reflection region in the reflective electrode 451 to a light-emitting region in the third light-emitting layer 454R. However, it is difficult to precisely determine the positions of the reflection region in the reflective electrode 451 and the light-emitting region in the third light-emitting layer 454R; therefore, it is assumed that the above effect can be sufficiently obtained wherever the reflection region and the light-emitting region may be set in the reflective electrode 451 and the third light-emitting layer 454R, respectively.

Next, the optical path length from the reflective electrode 451 to the second light-emitting layer 454G is adjusted to $(2n_G-1)\lambda_G/4$ ($n_G$ is a natural number of 1 or more) because in the second light-emitting element 450G, light (second reflected light) that is reflected by the reflective electrode 451 of the light emitted from the second light-emitting layer 454G interferes with light (second incident light) that directly enters the semi-transmissive and semi-reflective electrode 452 from the second light-emitting layer 454G. By adjusting the optical path length, the phases of the second reflected light and the second incident light can be aligned with each other and the light emitted from the second light-emitting layer 454G can be amplified.

Note that, strictly speaking, the optical path length from the reflective electrode 451 to the second light-emitting layer 454G can be the optical path length from a reflection region in the reflective electrode 451 to a light-emitting region in the second light-emitting layer 454G. However, it is difficult to precisely determine the positions of the reflection region in the reflective electrode 451 and the light-emitting region in the second light-emitting layer 454G; therefore, it is assumed that the above effect can be sufficiently obtained wherever the reflection region and the light-emitting region may be set in the reflective electrode 451 and the second light-emitting layer 454G, respectively.

Next, the optical path length from the reflective electrode 451 to the first light-emitting layer 454B is adjusted to $(2n_B-1)\lambda_B/4$ ($n_B$ is a natural number of 1 or more) because in the third light-emitting element 450B, light (third reflected light) that is reflected by the reflective electrode 451 of the light emitted from the first light-emitting layer 454B interferes with light (third incident light) that directly enters the semi-transmissive and semi-reflective electrode 452 from the first light-emitting layer 454B. By adjusting the optical path length, the phases of the third reflected light and the third incident light can be aligned with each other and the light emitted from the first light-emitting layer 454B can be amplified.

Note that, strictly speaking, the optical path length from the reflective electrode 451 to the first light-emitting layer 454B can be the optical path length from a reflection region in the reflective electrode 451 to a light-emitting region in the first light-emitting layer 454B. However, it is difficult to precisely determine the positions of the reflection region in the reflective electrode 451 and the light-emitting region in the first light-emitting layer 454B; therefore, it is assumed that the above effect can be sufficiently obtained wherever the reflection region and the light-emitting region may be set in the reflective electrode 451 and the first light-emitting layer 454B, respectively.

Note that although each of the light-emitting elements in the above-described structure includes a plurality of light-emitting layers in the EL layer, the present invention is not limited thereto; for example, the structure of the tandem (stacked type) light-emitting element that is described in Embodiment 3 can be combined, in which case a plurality of EL layers is provided so that a charge generating layer is interposed therebetween in one light-emitting element and one or more light-emitting layers are formed in each of the EL layers.

The light-emitting device described in this embodiment has a microcavity structure, in which light with wavelengths that differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

Note that the structure described in this embodiment can be combined as appropriate with any of the structures described in the other embodiments.

Embodiment 5

In this embodiment, a light-emitting device including a light-emitting element according to one embodiment of the present invention is described with reference to FIGS. 5A and 5B.

The light-emitting device including the light-emitting element according to one embodiment of the present invention can be either a passive matrix light-emitting device or an active matrix light-emitting device. Note that any of the light-emitting elements described in the other embodiments can be applied to the light-emitting device described in this embodiment.

In this embodiment, as a light-emitting device including the light-emitting element of one embodiment of the present invention, an active matrix light-emitting device is described with reference to FIGS. 5A and 5B.

Figure 5A:
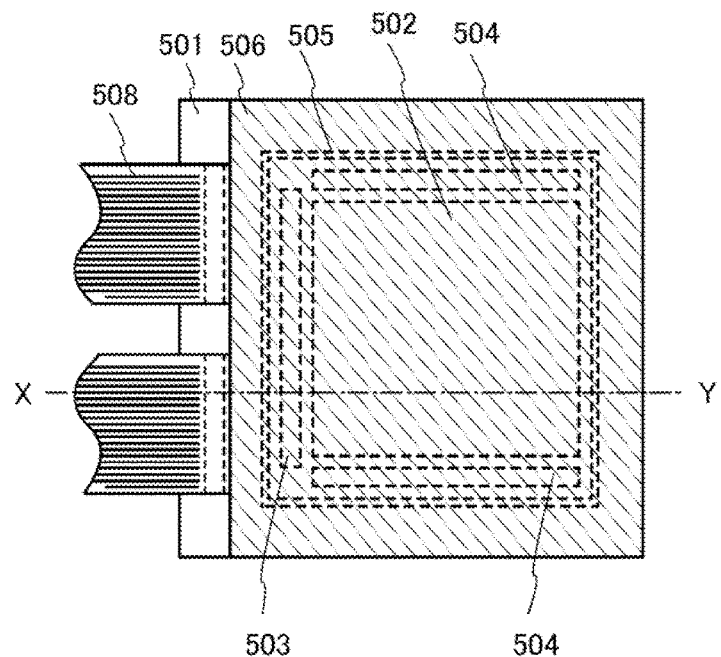
FIGS. 5A and 5B illustrate a light-emitting device of one embodiment of the present invention.
Figure 5B:
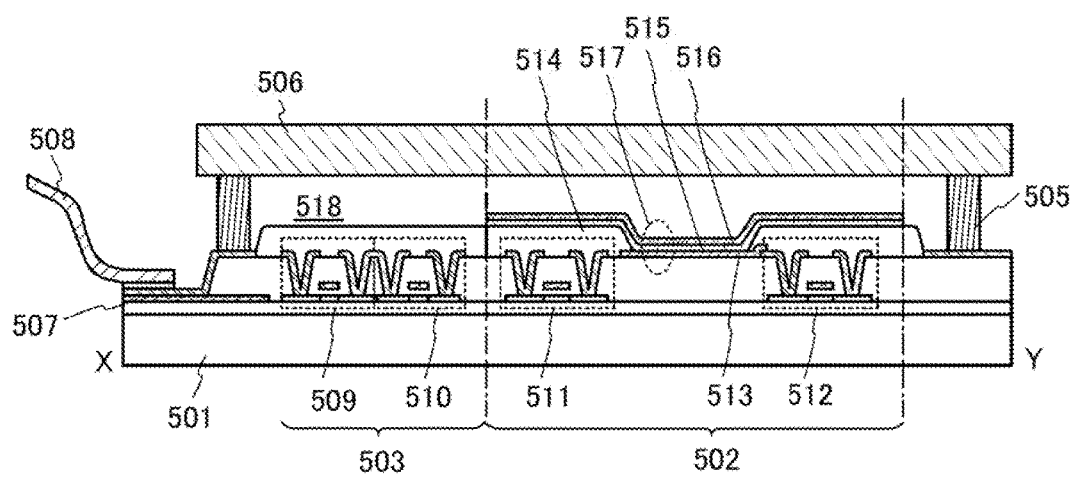

FIG. 5A is a top view of the light-emitting device and FIG. 5B is a cross-sectional view taken along the dashed-dotted line X-Y in FIG. 5A. The active matrix light-emitting device according to this embodiment includes a pixel portion 502 provided over an element substrate 501, a driver circuit portion (a source line driver circuit) 503, and a driver circuit portion (a gate line driver circuit) 504. The pixel portion 502, the driver circuit portion 503, and the driver circuit portion 504 are sealed with a sealant 505 between the element substrate 501 and a sealing substrate 506.

In addition, over the element substrate 501, a lead wiring 507 for connecting an external input terminal, through which a signal (e.g., a video signal, a clock signal, a start signal, a reset signal, or the like) or electric potential from the outside is transmitted to the driver circuit portion 503 and the driver circuit portion 504, is provided. Here, an example is described in which an FPC 508 is provided as the external input terminal. Although only the FPC is illustrated here, the FPC may be provided with a printed wiring board (PWB). The light-emitting device in this specification includes not only a light-emitting device itself but also a light-emitting device with an FPC or a PWB attached.

Next, a cross-sectional structure is described with reference to FIG. 5B. The driver circuit portion and the pixel portion are formed over the element substrate 501; here are illustrated the driver circuit portion 503 that is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. In this embodiment, although a driver-integrated type structure in which a driver circuit is formed over a substrate is described, a driver circuit is not necessarily formed over a substrate but can be formed outside a substrate.

The pixel portion 502 is formed of a plurality of pixels each of which includes a switching TFT 511, a current control TFT 512, and a first electrode 513 that is electrically connected to a wiring (a source electrode or a drain electrode) of the current control TFT 512. Note that an insulator 514 is formed to cover end portions of the first electrode 513. In this embodiment, the insulator 514 is formed using a positive photosensitive acrylic resin. Note that the first electrode 513 is used as an anode and a second electrode 516 is used as a cathode in this embodiment.

In addition, in order to obtain favorable coverage by a film that is to be stacked over the insulator 514, the insulator 514 is preferably formed so as to have a curved surface with curvature at an upper edge portion or a lower edge portion. For example, in the case of using a positive photosensitive acrylic resin as a material for the insulator 514, the insulator 514 is preferably formed so as to have a curved surface with a curvature radius (0.2 μm to 3 μm) at the upper edge portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode 516 are stacked over the first electrode 513. In the EL layer 515, at least a light-emitting layer is provided that contains an organometallic complex that is one embodiment of the present invention. In addition, in the EL layer 515, a hole-injection layer, a hole-transport layer, an electron-transport layer, an electron-injection layer, a charge-generation layer, and the like can be provided as appropriate in addition to the light-emitting layer.

A light-emitting element 517 is formed of a stacked structure of the first electrode 513, the EL layer 515, and the second electrode 516. For the first electrode 513, the EL layer 515, and the second electrode 516, the materials described in Embodiment 1 can be used. Although not illustrated, the second electrode 516 is electrically connected to an FPC 508 that is an external input terminal.

In addition, although the cross-sectional view of FIG. 5B illustrates only one light-emitting element 517, a plurality of light-emitting elements are arranged in matrix in the pixel portion 502. Light-emitting elements that emit light of three kinds of colors (R, G, and B) are selectively formed in the pixel portion 502, whereby a light-emitting device capable of full color display can be obtained. Alternatively, a light-emitting device that is capable of full color display may be manufactured by a combination with color filters.

Furthermore, the sealing substrate 506 is attached to the element substrate 501 with the sealant 505, whereby a light-emitting element 517 is provided in a space 518 surrounded by the element substrate 501, the sealing substrate 506, and the sealant 505. Note that the space 518 may be filled with an inert gas (such as nitrogen and argon) or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiber reinforced plastic (FRP), poly(vinyl fluoride) (PVF), polyester, acrylic, or the like can be used.

As described above, an active matrix light-emitting device can be obtained.

Note that the structure described in this embodiment can be combined as appropriate with any of the structures described in the other embodiments.

Embodiment 6

In this embodiment, electronic appliances each of that includes the light-emitting device of one embodiment of the present invention described in the above embodiment. Examples of the electronic appliances include cameras such as digital video cameras and digital cameras, goggle type displays, navigation systems, audio reproducing devices (e.g., car audio systems and audio systems), computers, game machines, portable information terminals (e.g., mobile computers, tablet terminals, mobile phones, portable game machines, and e-book readers), image reproducing devices in which a recording medium is provided (specifically, devices that are capable of replaying recording media such as digital versatile discs (DVDs) and equipped with a display device that can display an image). Specific examples of the electronic appliances are illustrated in FIGS. 6A to 6D and FIGS. 7A1, 7A2, 7A3, and 7B.

Figure 6A:
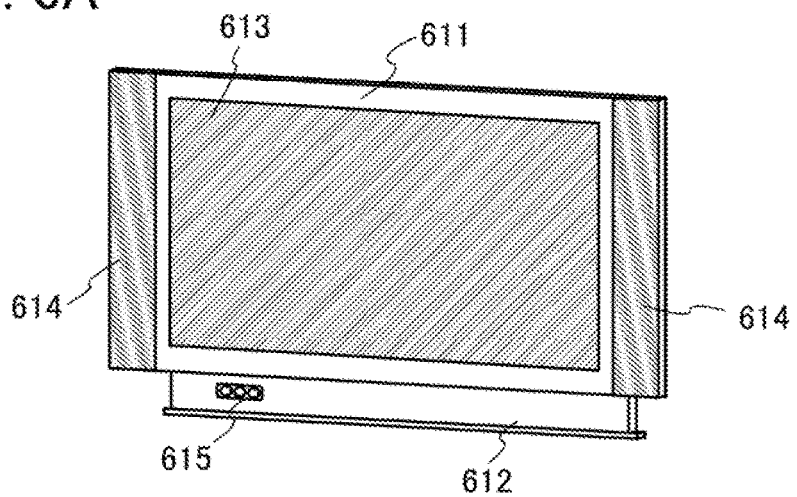
FIGS. 6A to 6D each illustrate an electronic appliance of one embodiment of the present invention.

FIG. 6A illustrates a television set of one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention is driven at low voltage and has high current efficiency, by the application of the light-emitting device of one embodiment of the present invention, a television set with reduced power consumption can be obtained.

Figure 6B:
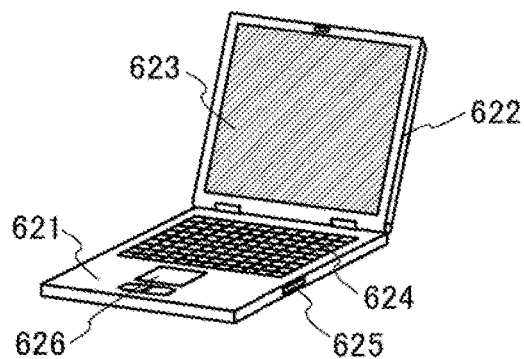

FIG. 6B illustrates a computer of one embodiment of the present invention, which includes a main body 621, a housing 622, a display portion 623, a keyboard 624, an external connection port 625, a pointing device 626, and the like. In this computer, the light-emitting device of one embodiment of the present invention can be applied to the display portion 623. Since the light-emitting device of one embodiment of the present invention is driven at low voltage and has high current efficiency, by the application of the light-emitting device of one embodiment of the present invention, a computer with reduced power consumption can be obtained.

Figure 6C:
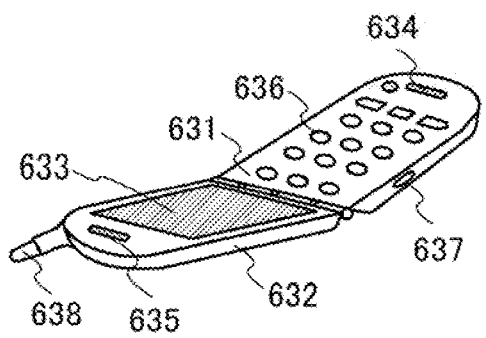

FIG. 6C illustrates a mobile phone of one embodiment of the present invention, which includes a main body 631, a housing 632, a display portion 633, an audio input portion 634, an audio output portion 635, operation keys 636, an external connection port 637, an antenna 638, and the like. In this mobile phone, the light-emitting device of one embodiment of the present invention can be applied to the display portion 633. Since the light-emitting device of one embodiment of the present invention is driven at low voltage and has high current efficiency, by the application of the light-emitting device of one embodiment of the present invention, a mobile phone with reduced power consumption can be obtained.

Figure 6D:
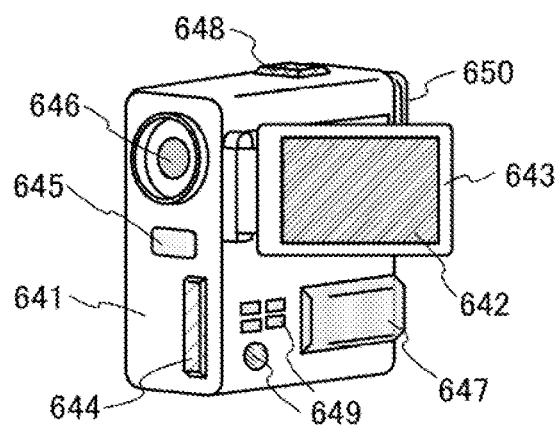

FIG. 6D illustrates a digital video camera of one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this digital video camera, the light-emitting device of one embodiment of the present invention can be applied to the display portion 642. Since the light-emitting device of one embodiment of the present invention is driven at low voltage and has high current efficiency, by the application of the light-emitting device of one embodiment of the present invention, a camera with reduced power consumption can be obtained.

FIGS. 7A1, 7A2, 7A3, and 7B illustrate examples of a tablet terminal. FIGS. 7A1, 7A2, and 7A3 illustrate a tablet terminal 5000. FIG. 7B illustrates a tablet terminal 6000.

FIGS. 7A1, 7A2, and 7A3 are a front view, a side view, and a rear view of the tablet terminal 5000, respectively. FIG. 7B is a front view of the tablet terminal 6000.

The tablet terminal 5000 includes a housing 5001, a display portion 5003, a power button 5005, a front camera 5007, a rear camera 5009, a first external connection terminal 5011, a second external connection terminal 5013, and the like.

In addition, the display portion 5003 is incorporated in the housing 5001 and can be used as a touch panel. For example, e-mailing or schedule management can be performed by touching an icon 5015 and the like on the display portion 5003. In addition, the front camera 5007 is incorporated on the front side of the housing 5001, whereby an image on the user's side can be taken. The rear camera 5009 is incorporated in the rear side of the housing 5001, whereby an image on the opposite side of the user can be taken. Furthermore, the housing 5001 includes the first external connection terminal 5011 and the second external connection terminal 5013. For example, sound can be output to an earphone or the like through the first external connection terminal 5011, and data can be moved through the second external connection terminal 5013.

The tablet terminal 6000 in FIG. 7B includes a first housing 6001, a second housing 6003, a hinge portion 6005, a first display portion 6007, a second display portion 6009, a power button 6011, a first camera 6013, a second camera 6015, and the like.

The first display portion 6007 is incorporated in the first housing 6001. The second display portion 6009 is incorporated in the second housing 6003. For example, the first display portion 6007 and the second display portion 6009 are used as a display panel and a touch panel, respectively. A user can select images, enter characters, and so on by touching an icon 6019 displayed on the second display portion 6009 or a keyboard 6021 (a keyboard image displayed on the second display portion 6009) while looking at a text icon 6017 displayed on the first display portion 6007. Alternatively, the first display portion 6007 and the second display portion 6009 may be a touch panel and a display panel, respectively; the first display portion 6007 and the second display portion 6009 may be touch panels.

The first housing 6001 and the second housing 6003 are connected to each other and open and close on the hinge portion 6005. In such a structure, the first display portion 6007 incorporated in the housing 6001 and the display portion 6009 incorporated in the second housing 6003 are preferably made to face each other, in which case the surfaces of the display portion 6007 and the display portion 6009 (e.g., plastic substrates) can be protected when the tablet terminal 6000 is carried.

Alternatively, the first housing 6001 and the second housing 6003 may be separated by the hinge portion 6005 (convertible type). Thus, the application range of the tablet terminal 6000 can be extended, and for example, the first housing 6001 is used in a vertical orientation and the second housing 6003 is used in a horizontal orientation.

The first camera 6013 and the second camera 6015 can take 3D images.

The tablet terminal 5000 and the tablet terminal 6000 may send and receive data wirelessly. For example, through wireless internet connection, desired data can be purchased and downloaded.

The tablet terminals 5000 and 6000 can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs). A detector such as a photodetector capable of optimizing display luminance in accordance with the amount of outside light or a sensor for detecting inclination, like a gyroscope or an acceleration sensor, can be included.

The light-emitting device of one embodiment of the present invention can be applied to the display portion 5003 of the tablet terminal 5000, the first display portion 6007 of the tablet terminal 6000, and/or the second display portion 6009 of the tablet terminal 6000. Since the light-emitting device of one embodiment of the present invention is driven at a low voltage and has high emission efficiency, a tablet terminal with reduced power consumption can be obtained.

As described above, the applicable range of the light-emitting device of one embodiment of the present invention is so wide that the light-emitting device can be applied to electronic appliances in a variety of fields. With the use of the light-emitting device of one embodiment of the present invention, an electronic appliance with reduced power consumption can be obtained.

Figure 8A:
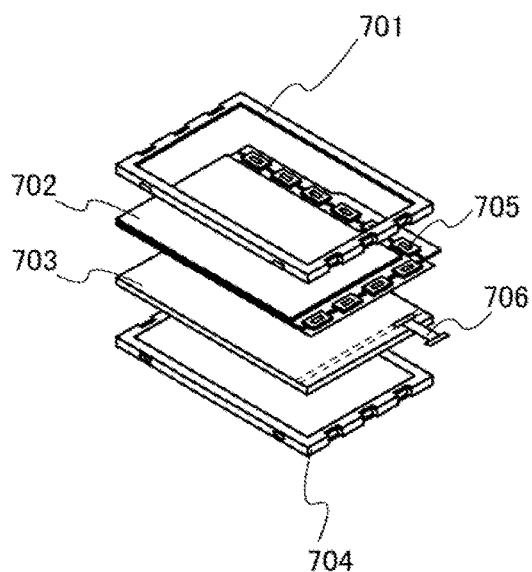
FIGS. 8A to 8C each illustrate a lighting device of one embodiment of the present invention.

The light-emitting device of one embodiment of the present invention can also be used as a lighting device. FIG. 8A illustrates an example of a liquid crystal display device using the light-emitting device of one embodiment of the present invention as a backlight. The liquid crystal display device illustrated in FIG. 8A includes a housing 701, a liquid crystal layer 702, a backlight 703, and a housing 704. The liquid crystal layer 702 is connected to a driver IC 705. The light-emitting device of one embodiment of the present invention is used as the backlight 703, and current is supplied to the backlight 703 through a terminal 706.

By using a light-emitting device of one embodiment of the present invention as a backlight of a liquid crystal display device as described above, a backlight having reduced power consumption can be obtained. Moreover, since the light-emitting device of one embodiment of the present invention is a lighting device for surface light emission and the enlargement of the light-emitting device is possible, the backlight can be made larger. Therefore, a larger-area liquid crystal display device that consumes low power can be obtained.

Figure 8B:
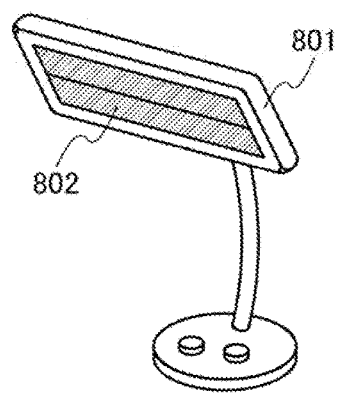

FIG. 8B illustrates an example in which the light-emitting device of one embodiment of the present invention is used for a desk lamp that is a lighting device. The desk lamp illustrated in FIG. 8B includes a housing 801 and a light source 802, and the light-emitting device of one embodiment of the present invention is used as the light source 802. Since the light-emitting device of one embodiment of the present invention is driven at low voltage and has high current efficiency, by the application of the light-emitting device of one embodiment of the present invention, a desk lamp with reduced power consumption can be obtained.

Figure 8C:
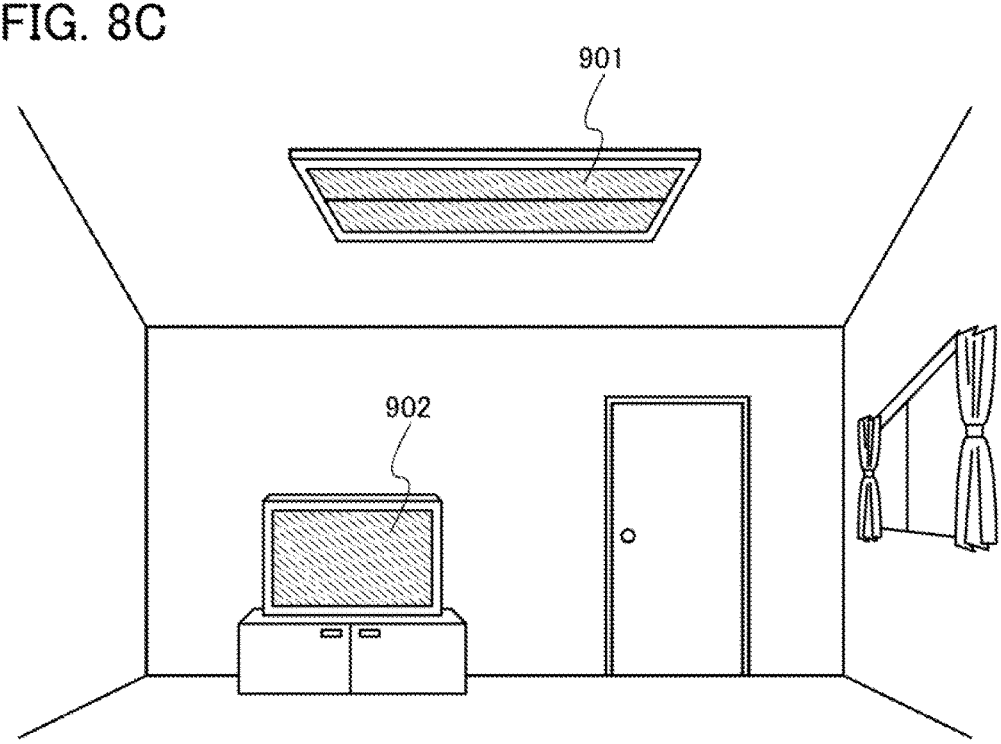

FIG. 8C illustrates an example in which the light-emitting device of one embodiment of the present invention is used for an indoor lighting device 901. Since the light-emitting device of one embodiment of the present invention can have a larger area, it can be used as a lighting device having a large area. Since the light-emitting device of one embodiment of the present invention is driven at low voltage and has high current efficiency, by the application of the light-emitting device of one embodiment of the present invention, a lighting device with reduced power consumption can be obtained. In a room where the light-emitting device of one embodiment of the present invention is used for the indoor lighting device 901 as described above, a television set 902 of one embodiment of the present invention as described with reference to FIG. 6A can be installed so that public broadcasting and movies can be watched.

Note that this embodiment can be combined as appropriate with any of the other embodiments.

Example 1

Synthesis Example 1

In Synthesis Example 1, a method of synthesizing bis[3-(6-tert-butyl-4-pyrimidinyl-κN3)-9-phenyl-9H-carbazol-2-yl-κC](2,2',6,6'-tetramethyl-3,5-heptanedionato-κ²O,O') iridium(III) (abbreviation: Ir(tBupczpm)₂(dpm)), which is the organometallic complex of one embodiment of the present invention represented by Structural Formula (100) and described in Embodiment 1, is specifically described.

<Method of Synthesizing Ir(tBupczpm)₂(Dpm) Represented by Structural Formula (100)>

First, an example of a method of synthesizing Ir(tBupczpm)₂(dpm) represented by Structural Formula (100) is described.

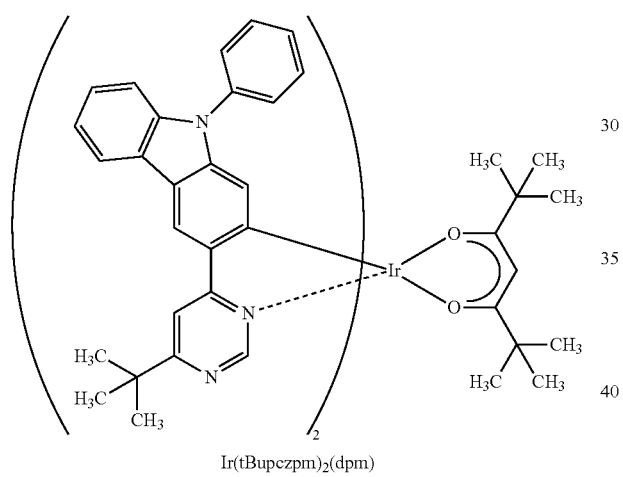

Ir(tBupczpm)₂(dpm)

Step 1: Synthesis of
4-tert-butyl-6-hydroxypyrimidine

First, 7.2 g of formamidine acetate, 7.5 g of sodium methoxide, and 70 mL of methanol were put in a 100-mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was condensed, and the given residue was dissolved in water. The solution was subjected to extraction with ethyl acetate. The obtained solution of the extract was washed with saturated saline, and anhydrate magnesium sulfate was added to the organic layer for drying. The magnesium sulfate was removed by gravity filtration, and the filtrate was concentrated to give a solid. This solid was washed with ethyl acetate to give 4-tert-butyl-6-hydroxypyrimidine (white powder, yield of 49%). A synthesis scheme of Step 1 is shown in (d-1).

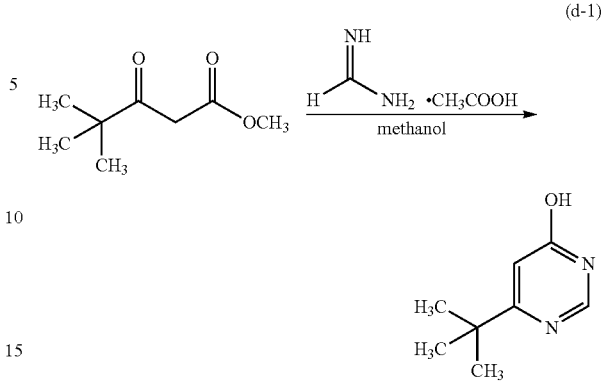

Step 2: Synthesis of 4-tert-butyl-6-chloropyrimidine

Next, 4.7 g of 4-tert-butyl-6-hydroxypyrimidine obtained in Step 1 and 14 mL of phosphoryl chloride were put into a 50-mL three-neck flask, and the mixture was heated and refluxed for 1.5 hours. After the reflux, phosphoryl chloride was distilled off under reduced pressure. The obtained residue was dissolved in dichloromethane, and washed with water and a saturated aqueous solution of sodium hydrogen carbonate. Anhydrate magnesium sulfate was added to the obtained organic layer for drying. The magnesium sulfate was removed by gravity filtration, and the filtrate was concentrated to give a solid. The obtained residue was purified by silica gel column chromatography using hexane and ethyl acetate as a developing solvent in a ratio of 10:1 to give 4-tert-butyl-6-chloropyrimidine (white powder, yield of 78%). A synthesis scheme of Step 2 is shown in (d-2).

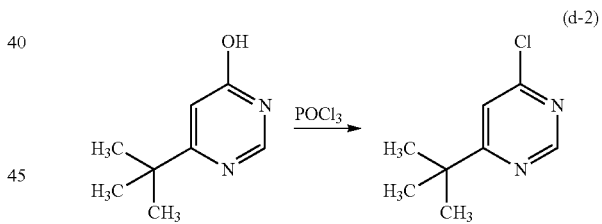

Step 3: Synthesis of 4-tert-butyl-6-(9-phenyl-9H-carbazol-3-yl)pyrimidine (Abbreviation: Htbupczpm)

Next, in a recovery flask equipped with a reflux pipe were put 1.00 g of 4-tert-butyl-6-chloropyrimidine obtained in Step 2, 3.44 g of 9-phenyl-9H-carbazol-3-ylboronic acid, 1.32 g of sodium carbonate, 0.050 g of bis(triphenylphosphine)palladium(II)dichloride (abbreviation: PdCl₂(PPh₃)₂), 20 mL of water, and 20 mL of DMF, and the air in the flask was replaced with argon. This flask was subjected to irradiation with microwaves (2.45 GHz, 100 W) for 60 minutes to be heated. Then, water was added to this solution and the organic layer was extracted with dichloromethane. The obtained organic layer was washed with water and saturated saline, and was dried with magnesium sulfate. The solution after the drying was filtered to remove the magnesium sulfate. The solvent of this solution was distilled off, and then the given residue was purified by flash column chromatography using hexane and ethyl acetate as a developing solvent in a ratio of 2:1 to give HtBupczpm, which was an objective pyrimidine derivative (white powder, yield of 95%). Note that the irradiation with microwaves was performed using a microwave synthesis system (Discover, manufactured by CEM Corporation). A synthesis scheme of Step 3 is shown in (d-3).

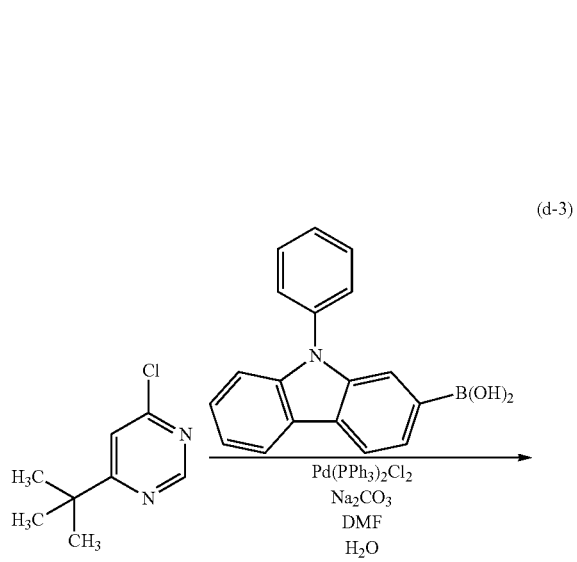

(d-3)

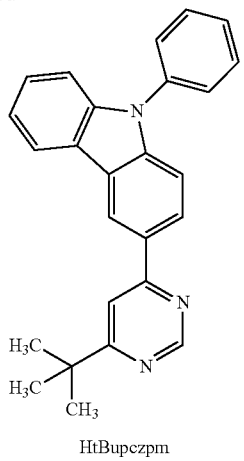

HtBupczpm

Step 4: Synthesis of di-μ-chloro-tetrakis[3-(6-tert-butyl-4-pyrimidinyl-κN3)-9-phenyl-9H-carbazol-2-yl-κC]diiridium(III) (abbreviation: [Ir(tBupczpm)$_2$Cl]$_2$)

Next, in a recovery flask equipped with a reflux pipe were put 30 mL of 2-ethoxyethanol, 10 mL of water, 2.10 g of HtBupczpm (abbreviation) obtained in Step 3, and 0.80 g of iridium chloride hydrate (IrCl$_3$.H$_2$O) (produced by Sigma-Aldrich Corporation), and the air in the flask was replaced with argon. After that, irradiation with microwaves (2.45 GHz, 100 W) was performed for 1 hour to cause a reaction. The solvent was distilled off, and then the given residue was suction-filtered and washed with ethanol to give [Ir(tBupczpm)$_2$Cl]$_2$ (abbreviation), which is a dinuclear complex, (green powder, yield of 72%). A synthesis scheme of Step 4 is shown in (d-4).

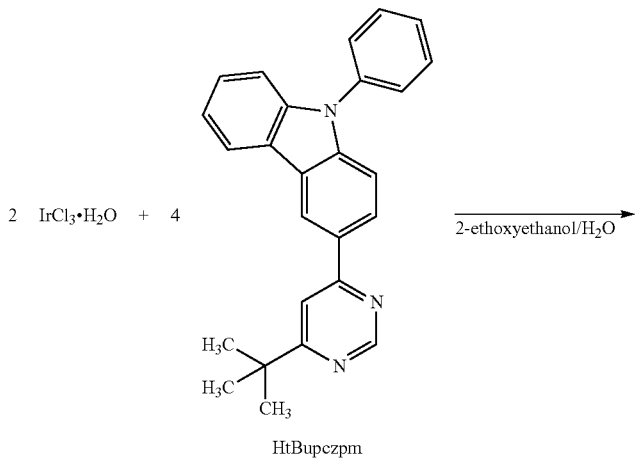

(d-4)

HtBupczpm

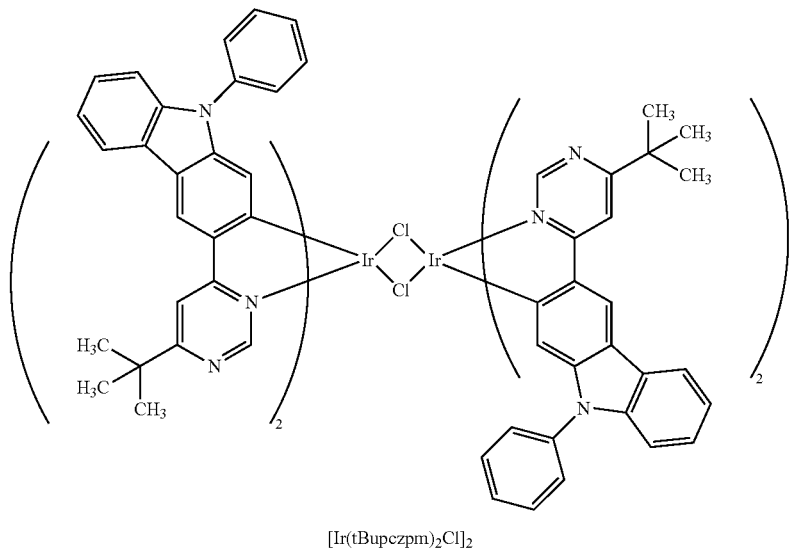

[Ir(tBupczpm)₂Cl]₂

Step 5: Synthesis of Ir(tBupczpm)₂(dpm)

Furthermore, in a recovery flask equipped with a reflux pipe were put 30 mL of 2-ethoxyethanol, 0.93 g of [Ir(tBupczpm)₂Cl]₂ that is the dinuclear complex obtained in Step 4, 0.26 g of dipivaloylmethane (abbreviation: Hdpm), and 0.50 g of sodium carbonate, and the air in the flask was replaced with argon. After that, the mixture was heated by irradiation with microwaves (2.45 GHz, 200 W) for 60 minutes. Here, 0.26 g of Hdpm was added, and the flask was subjected to irradiation with microwaves (2.45 GHz, 200 W) for 60 minutes to be heated. The solvent was distilled off, and the given residue was suction-filtered with ethanol. The obtained solid was washed with water and ethanol. The obtained solid was dissolved in dichloromethane and filtered through a filter aid in which Celite, alumina, and Celite were stacked in this order. Then, recrystallization was carried out with a mixed solvent of dichloromethane and ethanol. The obtained solid was purified by flash column chromatography using hexane and ethyl acetate as a developing solvent in a ratio of 5:1, and recrystallization was carried out with a mixed solvent of dichloromethane and methanol; thus, Ir(tBupczpm)₂(dpm), which is the organometallic complex of one embodiment of the present invention, was obtained as yellow orange powder (yield: 21%). A synthesis scheme of Step 5 is shown in (d-5).

(d-5)

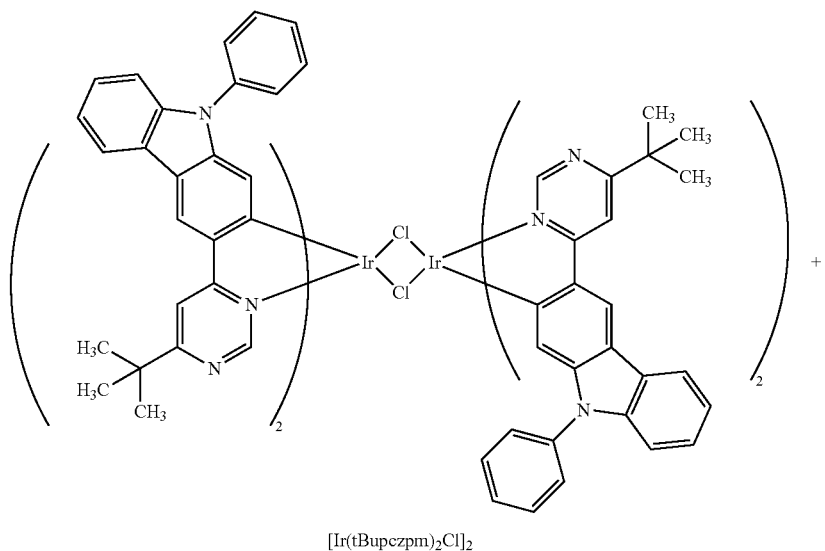

[Ir(tBupczpm)₂Cl]₂ +

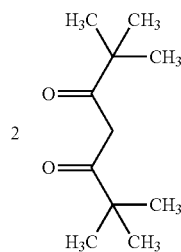 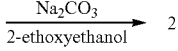 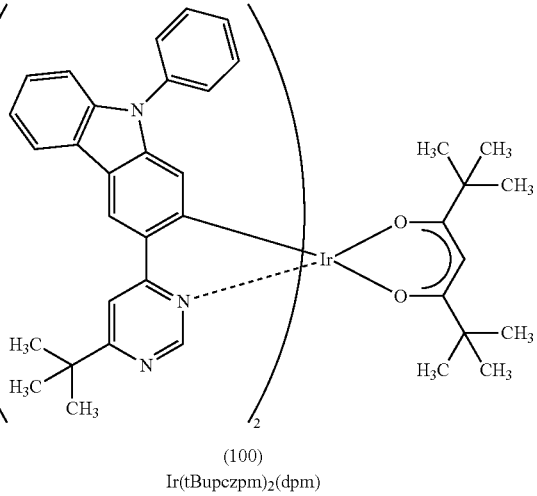

(100)
Ir(tBupczpm)₂(dpm)

Figure 9:
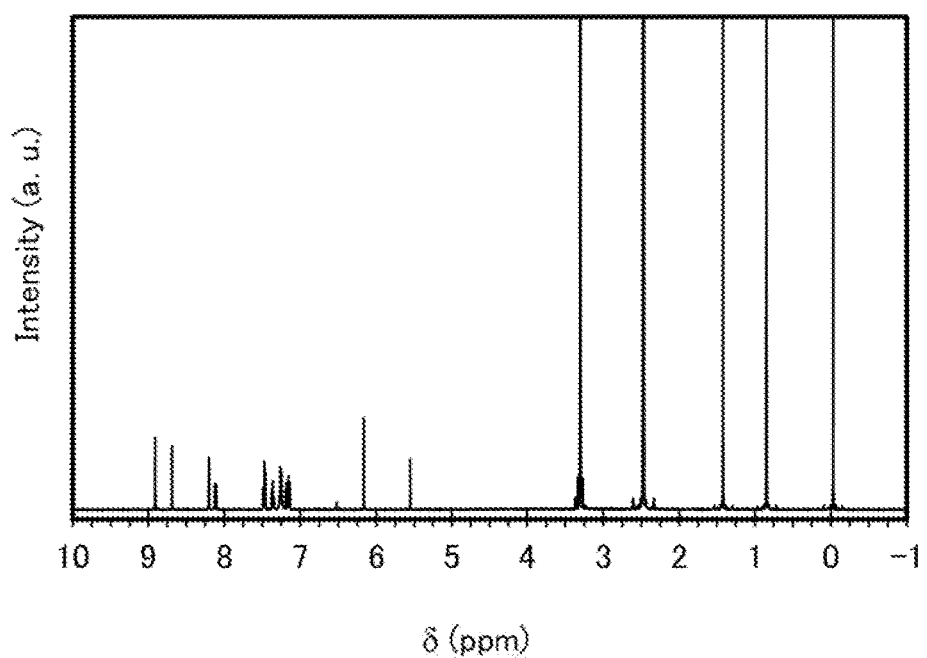
FIG. 9 is a $^1$H-NMR chart of an organometallic complex synthesized in Example 1.

Results of analysis of the yellow orange powder obtained in Step 5 by nuclear magnetic resonance spectrometry (¹H-NMR) are shown below. FIG. 9 is a ¹H-NMR chart. The results revealed that Ir(tBupczpm)₂(dpm), which is the organometallic complex of one embodiment of the present invention represented by Structural Formula (100), was obtained in Synthesis Example 1.

¹H-NMR. δ (DMSO-d₆): 0.87 (s, 18H), 1.45 (s, 18H), 5.58 (s, 1H), 6.19 (s, 2H), 7.18 (d, 2H), 7.21 (t, 2H), 7.28-7.30 (m, 6H), 7.39 (t, 2H), 7.50 (t, 4H), 8.14 (d, 2H), 8.23 (s, 2H), 8.71 (s, 2H), 8.94 (s, 2H).

Figure 10:
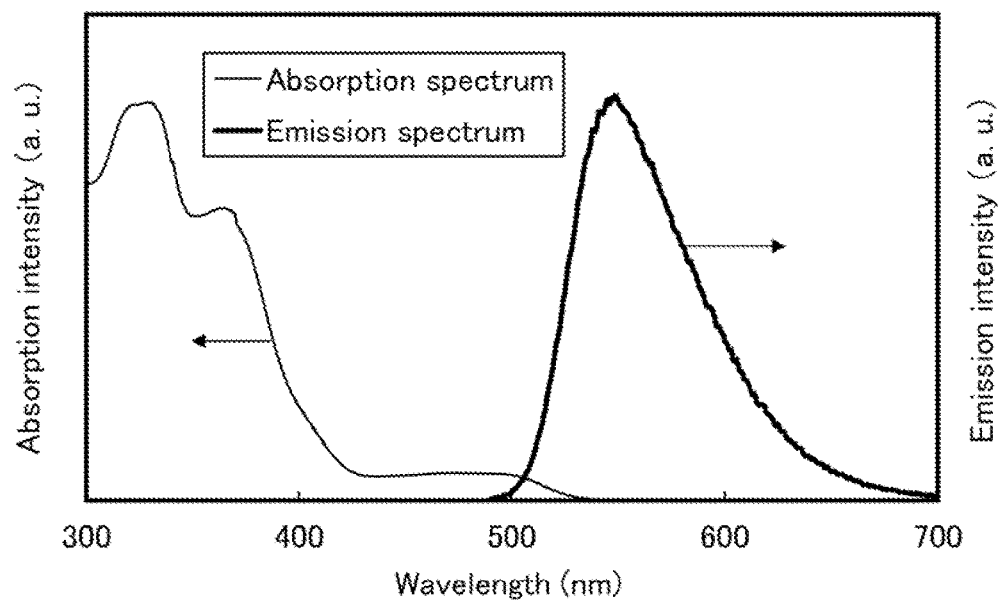
FIG. 10 shows an ultraviolet-visible absorption spectrum and an emission spectrum of Ir(tBupczpm)$_2$(dpm), which is an organometallic complex of one embodiment of the present invention, in a dichloromethane solution.

Next, an ultraviolet-visible absorption spectrum (hereinafter, simply referred to as an absorption spectrum) and an emission spectrum of Ir(tBupczpm)₂(dpm) in a dichloromethane solution were measured. The absorption spectrum was measured with the use of an ultraviolet-visible light spectrophotometer (V550 type manufactured by Japan Spectroscopy Corporation) in the state where the dichloromethane solution (0.059 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.059 mmol/L) was put in a quartz cell at room temperature. FIG. 10 shows measurement results of the absorption spectrum and the emission spectrum. The horizontal axis represents wavelength and the vertical axes represent absorption intensity and emission intensity. In FIG. 10, two solid lines are shown: a thin line represents the absorption spectrum, and a thick line represents the emission spectrum. Note that the absorption spectrum in FIG. 10 is a result obtained by subtraction of a measured absorption spectrum of only dichloromethane that was put in a quartz cell from the measured absorption spectrum of the dichloromethane solution (0.059 mmol/L) in a quartz cell.

As shown in FIG. 10, Ir(tBupczpm)₂(dpm), which is the organometallic complex of one embodiment of the present invention, had an emission peak at 549 nm, and yellow green light emission was observed from the dichloromethane solution.

Next, Ir(tBupczpm)₂(dpm) obtained in this example was analyzed by liquid chromatography mass spectrometry (LC/MS).

In the analysis by LC/MS, liquid chromatography (LC) separation was carried out with Acquity UPLC (manufactured by Waters Corporation), and mass spectrometry (MS) analysis was carried out with Xevo G2 Tof MS (manufactured by Waters Corporation). ACQUITY UPLC BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. A sample was prepared in such a manner that Ir(tBupczpm)₂(dpm) was dissolved in chloroform at a given concentration and the mixture was diluted with acetonitrile. The injection amount was 5.0 μL.

In the LC separation, a gradient method in which the composition of mobile phases is changed was employed. The ratio of Mobile Phase A to Mobile Phase B was 85:15 for 0 to 1 minute after the start of the measurement, and then the composition was changed so that the ratio of Mobile Phase A to Mobile Phase B in the 10th minute was 95:5. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. The mass range for the measurement was m/z=100 to 1300.

A component with m/z of 1129.48, which underwent the separation and the ionization under the above-described conditions, was collided with an argon gas in a collision cell to dissociate into product ions. The energy (collision energy) for the collision with argon was 70 eV. The detection results of the dissociated product ions by time-of-flight (TOF) MS are shown in FIG. 11.

Figure 11:
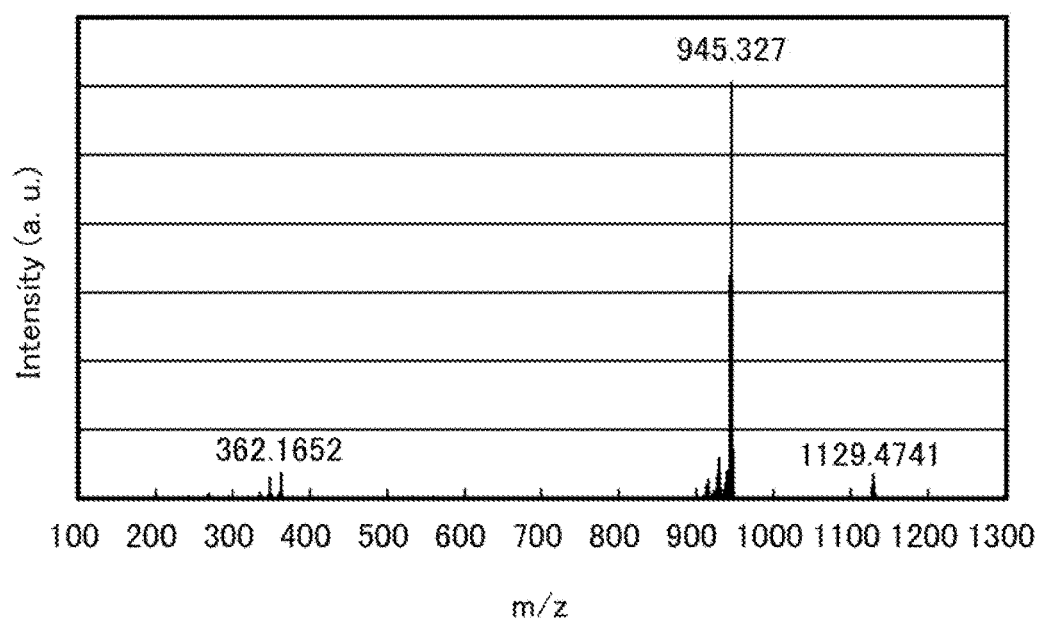
FIG. 11 shows LC/MS measurement results of Ir(tBupczpm)$_2$(dpm), which is the organometallic complex of one embodiment of the present invention.

The results in FIG. 11 show that product ions of Ir(tBupczpm)₂(dpm), which is the organometallic complex of one embodiment of the present invention represented by Structural Formula (100), were detected mainly around m/z=945.33 and around m/z=362.17. The results in FIG. 11 show characteristics derived from Ir(tBupczpm)₂(dpm) and can thus be regarded as important data in identification of Ir(tBupczpm)₂(dpm) contained in a mixture.

It is presumed that the product ion around m/z 945.33 is a cation in a state where dipivaloylmethane was eliminated from the compound represented by Structural Formula (100), and this is a characteristic of the organometallic complex of one embodiment of the present invention.

Example 2

Synthesis Example 2

In Synthesis Example 2, a method of synthesizing bis[3-(6-tert-butyl-4-pyrimidinyl-κN3)-9-phenyl-9H-carbazol-2-yl-κC](2,4-pentanedionato-κ²O,O')iridium(III) (abbreviation: Ir(tBupczpm)₂(acac)), which is the organometallic complex of one embodiment of the present invention represented by Structural Formula (101) and described in Embodiment 1, is specifically described.

<Method of Synthesizing Ir(tBupczpm)₂(Acac) Represented by Structural Formula (101)>

First, an example of a method of synthesizing Ir(tBupczpm)₂(acac) represented by Structural Formula (101) is described.

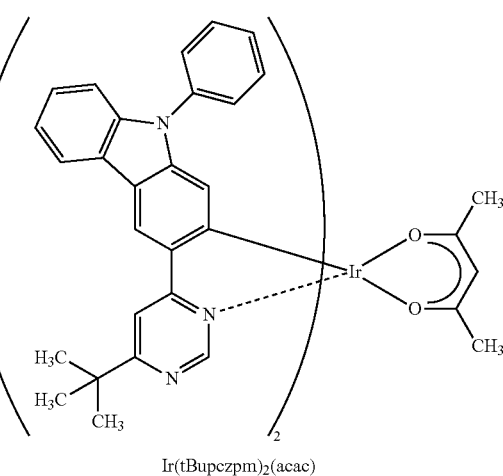

Ir(tBupczpm)₂(acac)

(101)

Synthesis of 4-tert-butyl-6-hydroxypyrimidine

First, 7.2 g of formamidine acetate, 7.5 g of sodium methoxide, and 70 mL of methanol were put in a 100-mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was concentrated, and the given residue was dissolved in water. The solution was subjected to extraction with ethyl acetate. The obtained solution of the extract was washed with saturated saline, and anhydrate magnesium sulfate was added to the organic layer for drying. The magnesium sulfate was removed by gravity filtration, and the filtrate was concentrated to give a solid. This solid was washed with ethyl acetate to give 4-tert-butyl-6-hydroxypyrimidine (white powder, yield of 49%). A synthesis scheme of Step 1 is shown in (e-1).

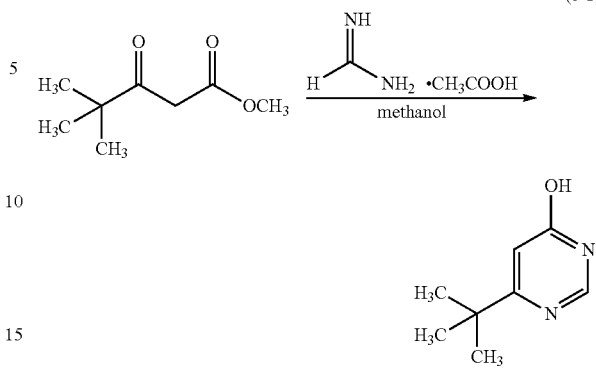

Step 2: Synthesis of 4-tert-butyl-6-chloropyrimidine

Next, 4.7 g of 4-tert-butyl-6-hydroxypyrimidine obtained in Step 1 and 14 mL of phosphoryl chloride were put into a 50-mL three-neck flask, and the mixture was heated and refluxed for 1.5 hours. After the reflux, phosphoryl chloride was distilled off under reduced pressure. The obtained residue was dissolved in dichloromethane, and washed with water and a saturated aqueous solution of sodium hydrogen carbonate. Anhydrate magnesium sulfate was added to the obtained organic layer for drying. The magnesium sulfate was removed by gravity filtration, and the filtrate was concentrated to give a solid. The obtained residue was purified by silica gel column chromatography using hexane and ethyl acetate as a developing solvent in a ratio of 10:1 to give 4-tert-butyl-6-chloropyrimidine (white powder, yield of 78%). A synthesis scheme of Step 2 is shown in (e-2).

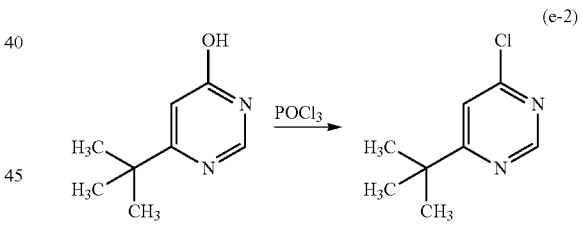

Step 3: Synthesis of 4-tert-butyl-6-(9-phenyl-9H-carbazol-3-yl)pyrimidine (Abbreviation: HtBupczpm)

Next, in a recovery flask equipped with a reflux pipe were put 1.00 g of 4-tert-butyl-6-chloropyrimidine obtained in Step 2, 3.44 g of 9-phenyl-9H-carbazol-3-ylboronic acid, 1.32 g of sodium carbonate, 0.050 g of bis(triphenylphosphine)palladium(II)dichloride (abbreviation: PdCl₂(PPh₃)₂), 20 mL of water, and 20 mL of DMF, and the air in the flask was replaced with argon. This flask was subjected to irradiation with microwaves (2.45 GHz, 100 W) for 60 minutes to be heated. Then, water was added to this solution and the organic layer was extracted with dichloromethane. The obtained organic layer was washed with water and saturated saline, and was dried with magnesium sulfate. The solution obtained by the drying was filtered to remove the magnesium sulfate. The solvent of this solution was distilled off, and then the given residue was purified by flash column chromatography using hexane and ethyl acetate as a developing solvent in a ratio of 2:1 to give HtBupczpm, which was an objective pyrimidine derivative (white powder, yield of 95%). Note that the irradiation with microwaves was performed using a microwave synthesis system (Discover, manufactured by CEM Corporation). A synthesis scheme of Step 3 is shown in (e-3).

(e-3)

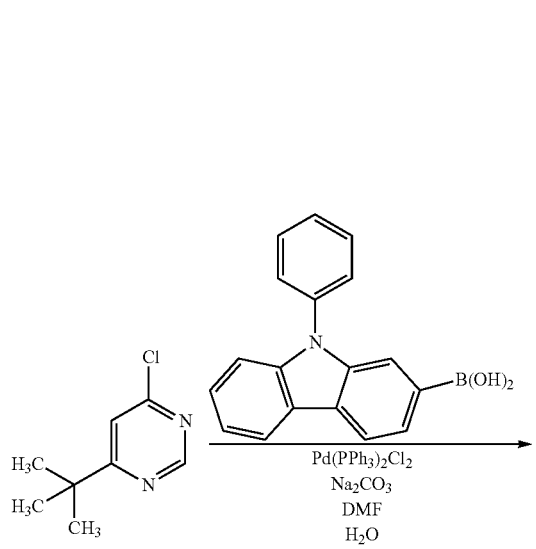

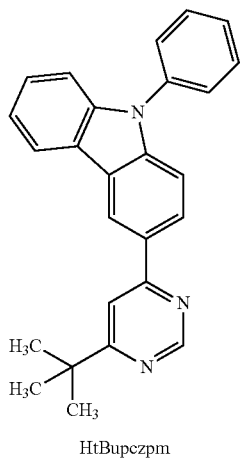

HtBupczpm

Step 4: Synthesis of di-μ-chloro-tetrakis[3-(6-tert-butyl-4-pyrimidinyl-κN3)-9-phenyl-9H-carbazol-2-yl-κC]diiridium(III) (abbreviation: [Ir(tBupczpm)$_2$Cl]$_2$)

Next, in a recovery flask equipped with a reflux pipe were put 30 mL of 2-ethoxyethanol, 10 mL of water, 2.10 g of HtBupczpm (abbreviation) obtained in Step 3, and 0.80 g of iridium chloride hydrate (IrCl$_3$.H$_2$O) (produced by Sigma-Aldrich Corporation), and the air in the flask was replaced with argon. After that, irradiation with microwaves (2.45 GHz, 100 W) was performed for 1 hour to cause a reaction. The solvent was distilled off, and then the given residue was suction-filtered and washed with ethanol to give [Ir(tBupczpm)$_2$Cl]$_2$ (abbreviation), which is a dinuclear complex, (green powder, yield of 72%). A synthesis scheme of Step 4 is shown in (e-4).

(e-4)

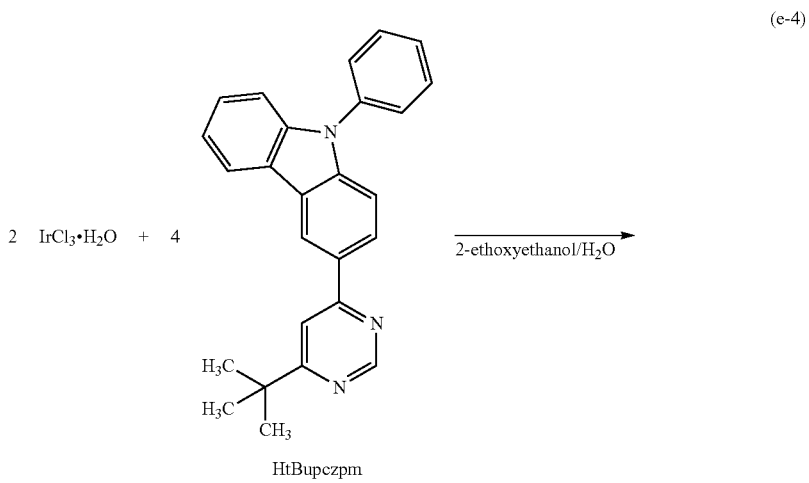

HtBupczpm

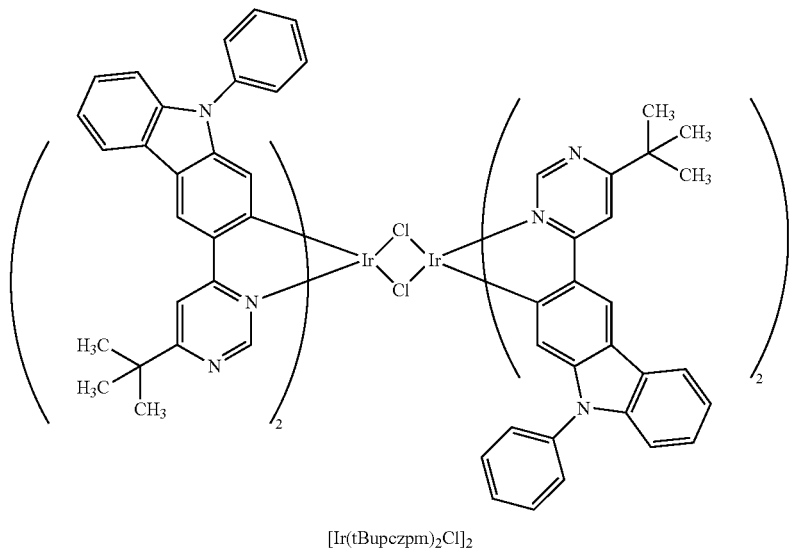

[Ir(tBupczpm)₂Cl]₂

Step 5: Synthesis of Ir(tBupczpm)₂(acac)

Furthermore, in a recovery flask equipped with a reflux pipe were put 30 mL of 2-ethoxyethanol, 0.99 g of [Ir(tBupczpm)₂Cl]₂ that is the dinuclear complex obtained in Step 4, 0.15 g of acetylacetone (abbreviation: Hacac), and 0.53 g of sodium carbonate, and the air in the flask was replaced with argon. After that, the mixture was heated by irradiation with microwaves (2.45 GHz, 200 W) for 60 minutes. Here, 0.15 g of Hacac was added, and the flask was subjected to irradiation with microwaves (2.45 GHz, 120 W) for 60 minutes to be heated. The solvent was distilled off, and the given residue was suction-filtered with ethanol. The obtained solid was washed with water and ethanol. The obtained solid was dissolved in dichloromethane and filtered through a filter aid in which Celite, alumina, and Celite were stacked in this order. The filtrate was concentrated to give a solid. The obtained solid was purified by flash column chromatography using dichloromethane and ethyl acetate as a developing solvent in a ratio of 10:1, and recrystallization was carried out with a mixed solvent of dichloromethane and methanol; thus, Ir(tBupczpm)₂(acac), which is the organometallic complex of one embodiment of the present invention, was obtained as yellow orange powder (yield: 22%). A synthesis scheme of Step 5 is shown in (e-5).

(e-5)

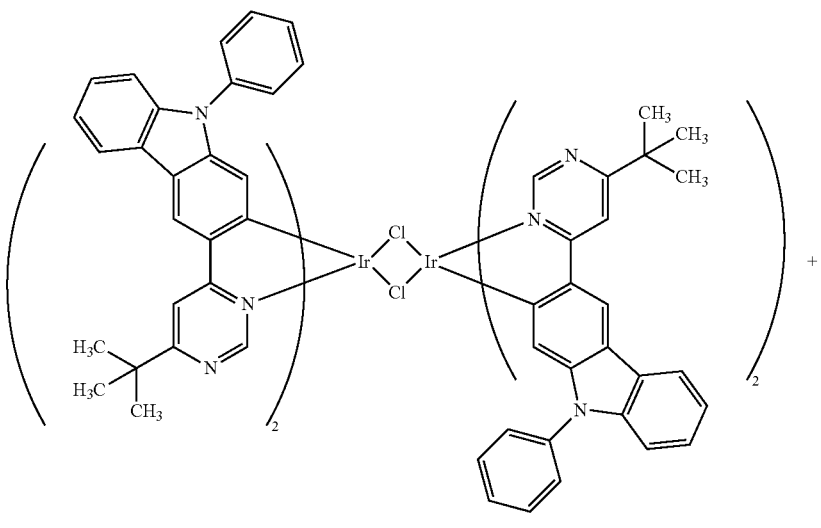

[Ir(tBupczpm)₂Cl]₂ +

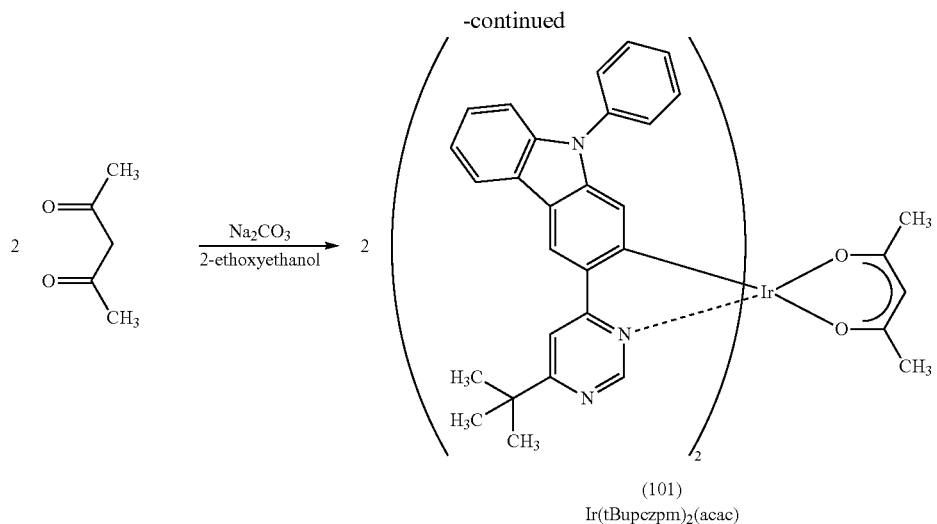

(101)
Ir(tBupczpm)₂(acac)

Figure 12:
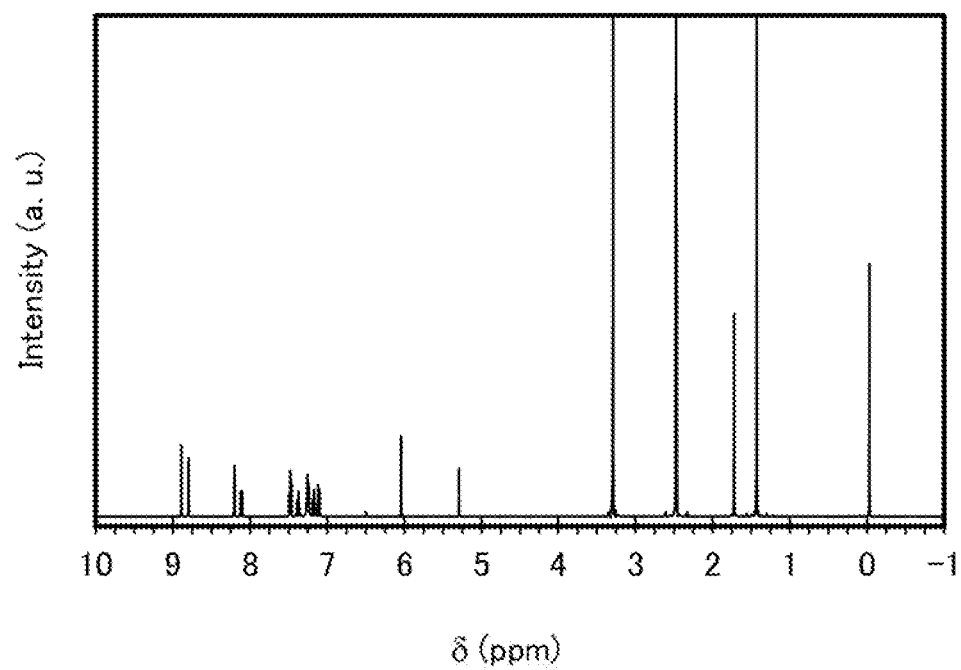
FIG. 12 is a $^1$H-NMR chart of an organometallic complex synthesized in Example 2.

Results of analysis of the yellow powder obtained in Step 5 by nuclear magnetic resonance spectrometry ($^1$H-NMR) are shown below. FIG. 12 is a $^1$H-NMR chart. The results revealed that Ir(tBupczpm)₂(acac), which is the organometallic complex of one embodiment of the present invention represented by Structural Formula (101), was obtained in Synthesis Example 2.

$^1$H-NMR. δ(DMSO-d₆): 1.46 (s, 18H), 1.75 (s, 6H), 5.32 (s, 1H), 6.07 (s, 2H), 7.14 (d, 2H), 7.20 (t, 2H), 7.27-7.30 (m, 6H), 7.40 (t, 2H), 7.51 (t, 4H), 8.14 (d, 2H), 8.23 (s, 2H), 8.83 (s, 2H), 8.92 (s, 2H).

Figure 13:
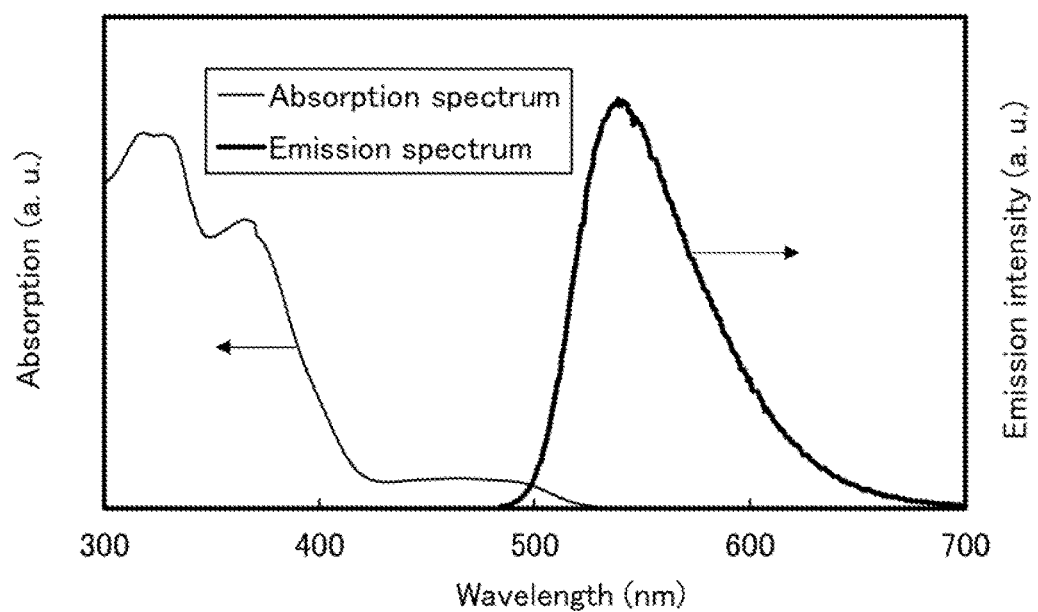
FIG. 13 shows an ultraviolet-visible absorption spectrum and an emission spectrum of Ir(tBupczpm)$_2$(acac), which is an organometallic complex of one embodiment of the present invention, in a dichloromethane solution.

Next, an ultraviolet-visible absorption spectrum (absorption spectrum) and an emission spectrum of Ir(tBupczpm)₂(acac) in a dichloromethane solution were measured. The absorption spectrum and the emission spectrum were measured using the same apparatus and method as Example 1. FIG. 13 shows measurement results of the absorption spectrum and the emission spectrum. The horizontal axis represents wavelength and the vertical axes represent absorption intensity and emission intensity. In FIG. 13, two solid lines are shown: a thin line represents the absorption spectrum, and a thick line represents the emission spectrum. Note that the absorption spectrum in FIG. 13 is a result obtained by subtraction of a measured absorption spectrum of only dichloromethane that was put in a quartz cell from the measured absorption spectrum of the dichloromethane solution (0.064 mmol/L) in a quartz cell.

As shown in FIG. 13, Ir(tBupczpm)₂(acac), which is the organometallic complex of one embodiment of the present invention, had an emission peak at 539 nm, and yellow green light emission was observed from the dichloromethane solution.

Next, Ir(tBupczpm)₂(acac) obtained in this example was analyzed by LC/MS.

The LC/MS analysis was performed using the same measurement apparatus and measurement method as Example 1. Note that a sample was prepared in such a manner that Ir(tBupczpm)₂(acac) was dissolved in chloroform at a given concentration and the mixture was diluted with acetonitrile. The injection amount was 5.0 μL.

In the LC separation, a gradient method in which the composition of mobile phases is changed was employed. The ratio of Mobile Phase A to Mobile Phase B was 75:25 for 0 to 1 minute after the start of the measurement, and then the composition was changed so that the ratio of Mobile Phase A to Mobile Phase B in the 10th minute was 95:5. The composition was changed linearly. In the MS analysis, ionization was carried out by ESI. At this time, the capillary voltage and the sample cone voltage were set to 3.0 kV and 30 V, respectively, and detection was performed in a positive mode. The mass range for the measurement was m/z=100 to 1200.

A component with m/z of 1044.40, which underwent the separation and the ionization under the above-described conditions, was collided with an argon gas in a collision cell to dissociate into product ions. The energy (collision energy) for the collision with argon was 30 eV. The detection results of the dissociated product ions by time-of-flight (TOF) MS are shown in FIG. 14.

Figure 14:
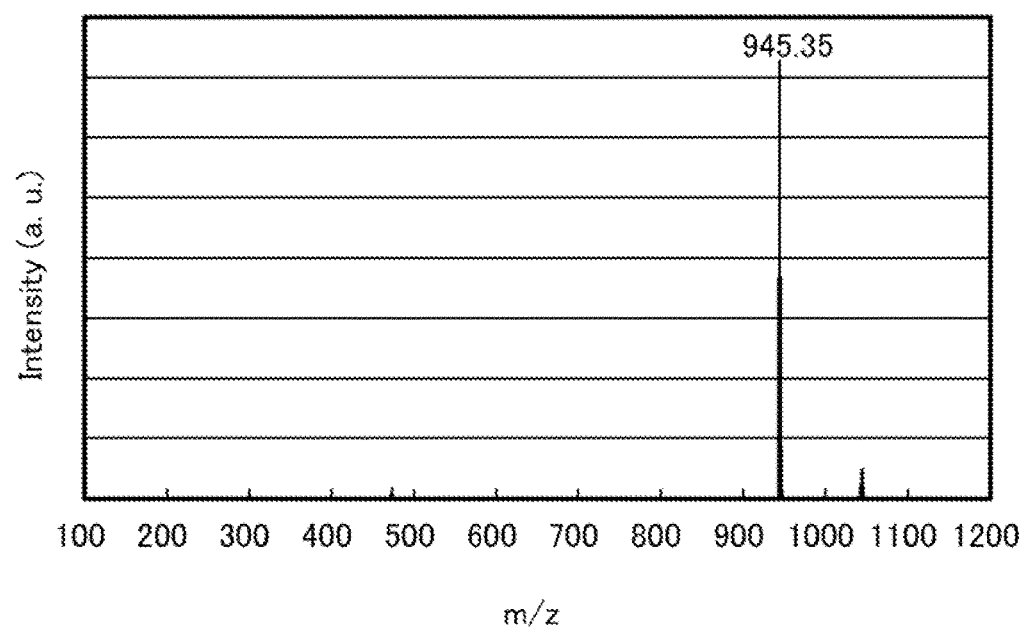
FIG. 14 shows LC/MS measurement results of Ir(tBupczpm)$_2$(acac), which is the organometallic complex of one embodiment of the present invention.

The results in FIG. 14 show that a product ion of Ir(tBupczpm)₂(acac), which is the organometallic complex of one embodiment of the present invention represented by Structural Formula (101), was detected mainly around m/z=945.35. The results in FIG. 14 show characteristics derived from Ir(tBupczpm)₂(acac) and can thus be regarded as important data in identification of Ir(tBupczpm)₂(acac) contained in a mixture.

It is presumed that the product ion around m/z 945.35 is a cation in a state where acetylacetone was eliminated from the compound represented by Structural Formula (101), and this is a characteristic of the organometallic complex of one embodiment of the present invention.

Example 3

Synthesis Example 3

In Synthesis Example 3, a method of synthesizing tris[3-(6-tert-butyl-4-pyrimidinyl-κN3)-9-phenyl-9H-carbazol-2-yl-κC]iridium(III) (abbreviation: Ir(tBupczpm)₃), which is the organometallic complex of one embodiment of the present invention represented by Structural Formula (112) and described in Embodiment 1, is specifically described.

<Method of Synthesizing Ir(tBupczpm)₃ Represented by Structural Formula (112)>

First, an example of a method of synthesizing Ir(tBupczpm)₃ represented by Structural Formula (112) is described.

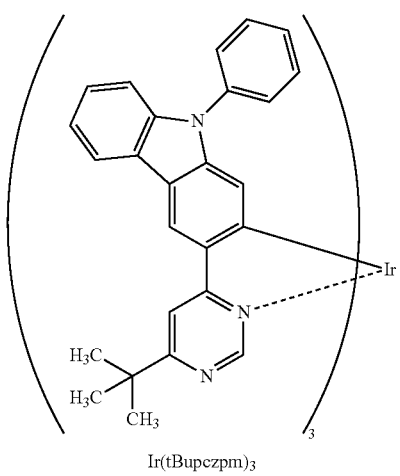

Ir(tBupczpm)₃

Step 1: Synthesis of 4-tert-butyl-6-hydroxypyrimidine

First, 7.2 g of formamidine acetate, 7.5 g of sodium methoxide, and 70 mL of methanol were put in a 100-mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was condensed, and the given residue was dissolved in water. The solution was subjected to extraction with ethyl acetate. The obtained solution of the extract was washed with saturated saline, and anhydrate magnesium sulfate was added to the organic layer for drying. The magnesium sulfate was removed by gravity filtration, and the filtrate was concentrated to give a solid. This solid was washed with ethyl acetate to give 4-tert-butyl-6-hydroxypyrimidine (white powder, yield of 49%). A synthesis scheme of Step 1 is shown in (f-1).

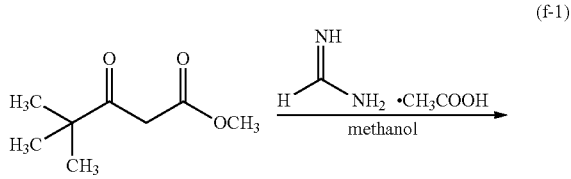

(f-1)

Step 2: Synthesis of 4-tert-butyl-6-chloropyrimidine

Next, 4.7 g of 4-tert-butyl-6-hydroxypyrimidine obtained in Step 1 and 14 mL of phosphoryl chloride were put into a 50-mL three-neck flask, and the mixture was heated and refluxed for 1.5 hours. After the reflux, phosphoryl chloride was distilled off under reduced pressure. The obtained residue was dissolved in dichloromethane, and washed with water and a saturated aqueous solution of sodium hydrogen carbonate. Anhydrate magnesium sulfate was added to the obtained organic layer for drying. The magnesium sulfate was removed by gravity filtration, and the filtrate was concentrated to give a solid. The obtained residue was purified by silica gel column chromatography using hexane and ethyl acetate as a developing solvent in a ratio of 10:1 to give 4-tert-butyl-6-chloropyrimidine (white powder, yield of 78%). A synthesis scheme of Step 2 is shown in (f-2).

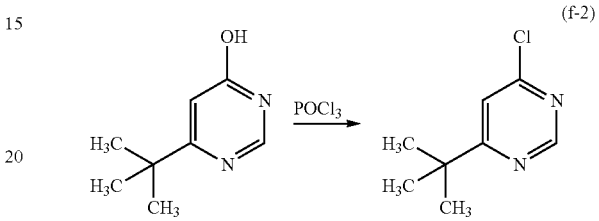

(f-2)

Step 3: Synthesis of 4-tert-butyl-6-(9-phenyl-9H-carbazol-3-yl)pyrimidine (Abbreviation: HtBupczpm)

Next, in a recovery flask equipped with a reflux pipe were put 1.00 g of 4-tert-butyl-6-chloropyrimidine obtained in Step 2, 3.44 g of 9-phenyl-9H-carbazol-3-ylboronic acid, 1.32 g of sodium carbonate, 0.050 g of bis(triphenylphosphine)palladium(II)dichloride (abbreviation: PdCl₂(PPh₃)₂), 20 mL of water, and 20 mL of DMF, and the air in the flask was replaced with argon. This flask was subjected to irradiation with microwaves (2.45 GHz, 100 W) for 60 minutes to be heated. Then, water was added to this solution and the organic layer was extracted with dichloromethane. The obtained organic layer was washed with water and saturated saline, and was dried with magnesium sulfate. The solution obtained by the drying was filtered to remove the magnesium sulfate. The solvent of this solution was distilled off, and then the given residue was purified by flash column chromatography using hexane and ethyl acetate as a developing solvent in a ratio of 2:1 to give HtBupczpm, which was an objective pyrimidine derivative (white powder, yield of 95%). Note that the irradiation with microwaves was performed using a microwave synthesis system (Discover, manufactured by CEM Corporation). A synthesis scheme of Step 3 is shown in (f-3).

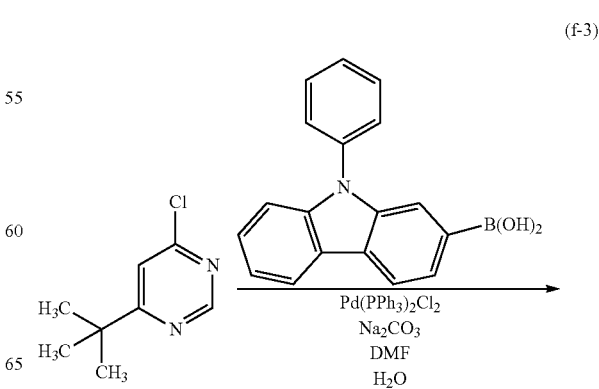

(f-3)

-continued

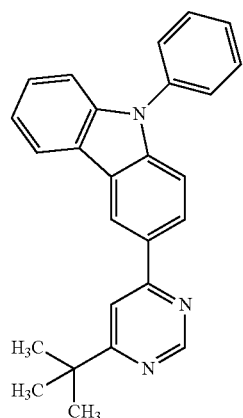

HtBupczpm

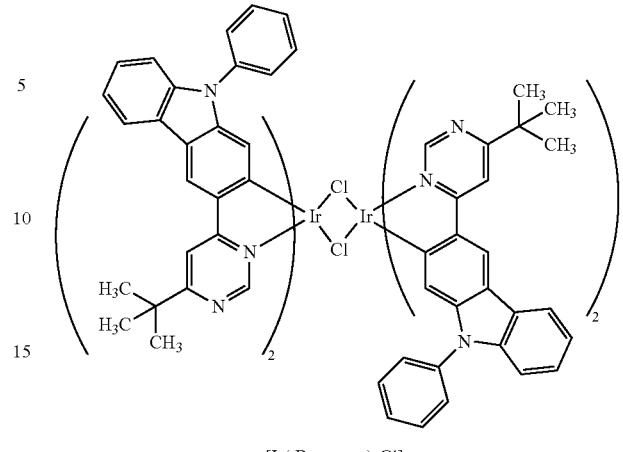

[Ir(tBupczpm)₂Cl]₂

Step 4: Synthesis of di-μ-chloro-tetrakis[3-(6-tert-butyl-4-pyrimidinyl-κN3)-9-phenyl-9H-carbazol-2-yl-κC]diiridium(III) (abbreviation: [Ir(tBupczpm)₂Cl]₂)

Next, in a recovery flask equipped with a reflux pipe were put 30 mL of 2-ethoxyethanol, 10 mL of water, 2.10 g of HtBupczpm (abbreviation) obtained in Step 3, and 0.80 g of iridium chloride hydrate (IrCl₃·H₂O) (produced by Sigma-Aldrich Corporation), and the air in the flask was replaced with argon. After that, irradiation with microwaves (2.45 GHz, 100 W) was performed for 1 hour to cause a reaction. The solvent was distilled off, and then the given residue was suction-filtered and washed with ethanol to give [Ir(tBupczpm)₂Cl]₂, a dinuclear complex (green powder, yield of 72%). A synthesis scheme of Step 4 is shown in (f-4).

Step 5: Synthesis of Ir(tBupczpm)₃

Furthermore, in a 100-mL three-neck flask equipped with a reflux pipe were put 10 g of phenol, 1.07 g of [Ir(tBupczpm)₂Cl]₂ that is the dinuclear complex obtained in Step 4, 1.06 g of HtBupczpm, and 0.77 g of potassium carbonate, and the air in the flask was replaced with nitrogen. After that, the mixture was heated at 185° C. for 9 hours to be reacted. The obtained residue was irradiated with ultrasonic waves and suction-filtered in methanol. The obtained solid was dissolved in dichloromethane and washed with water and saturated saline. The obtained organic layer was dried with magnesium sulfate, and the solution after the drying was filtered to remove the magnesium sulfate. The solvent of this solution was distilled off, and the obtained residue was dissolved in dichloromethane and filtered through Celite/alumina/Celite. Then, recrystallization was carried out with a mixed solvent of dichloromethane and ethanol; thus, Ir(tBupczpm)₃, which is the organometallic complex of one embodiment of the present invention, was obtained as yellow powder (yield: 74%). A synthesis scheme of Step 5 is shown in (f-5).

(f-4)

2 IrCl₃·H₂O +

(f-5)

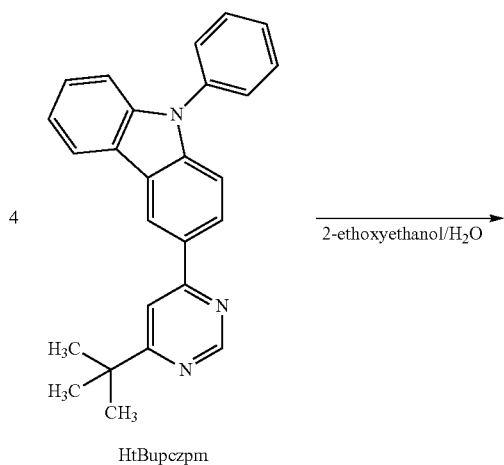

4

HtBupczpm

→ 2-ethoxyethanol/H₂O

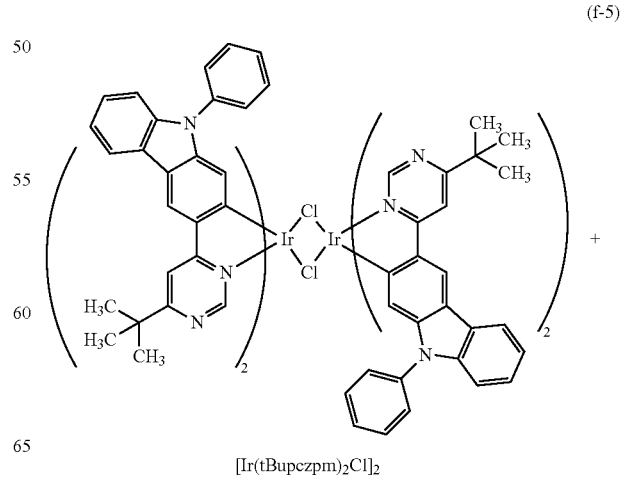

[Ir(tBupczpm)₂Cl]₂

+

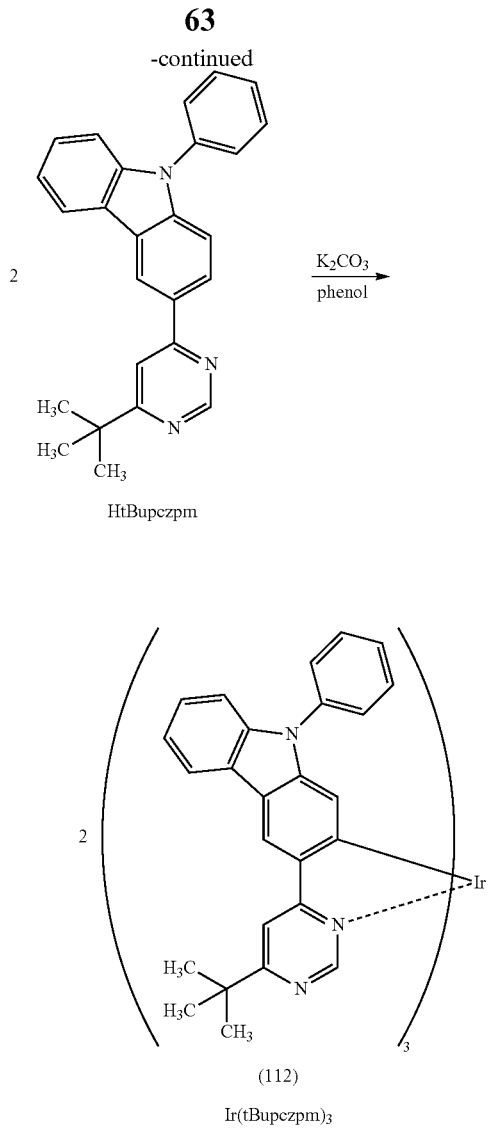

HtBupczpm

Ir(tBupczpm)₃

Figure 15:
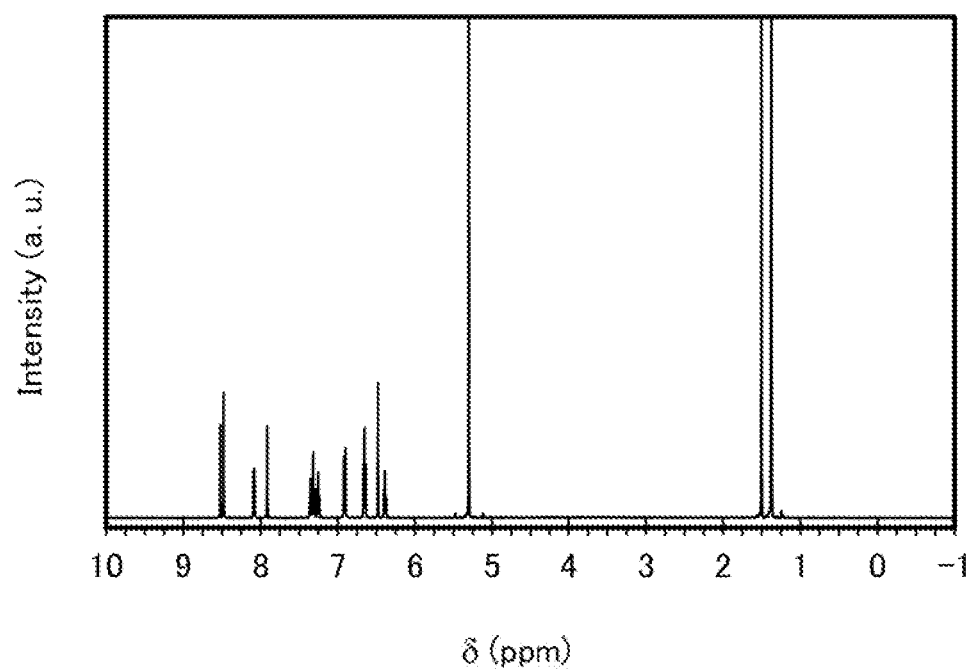
FIG. 15 is a $^1$H-NMR chart of an organometallic complex synthesized in Example 3.

Results of analysis of the yellow powder obtained in Step 5 by nuclear magnetic resonance spectrometry (¹H-NMR) are shown below. FIG. 15 is a ¹H-NMR chart. The results revealed that Ir(tBupczpm)₃, which is the organometallic complex of one embodiment of the present invention represented by Structural Formula (112), was obtained in Synthesis Example 3.

¹H-NMR. δ (CD₂Cl₂): 1.39 (s, 27H), 6.41 (t, 3H), 6.50 (s, 3H), 6.67 (t, 6H), 6.93 (d, 6H), 7.27 (t, 3H), 7.32-7.37 (m, 6H), 7.93 (s, 3H), 8.10 (d, 3H), 8.50 (s, 3H), 8.54 (s, 3H).

Figure 16:
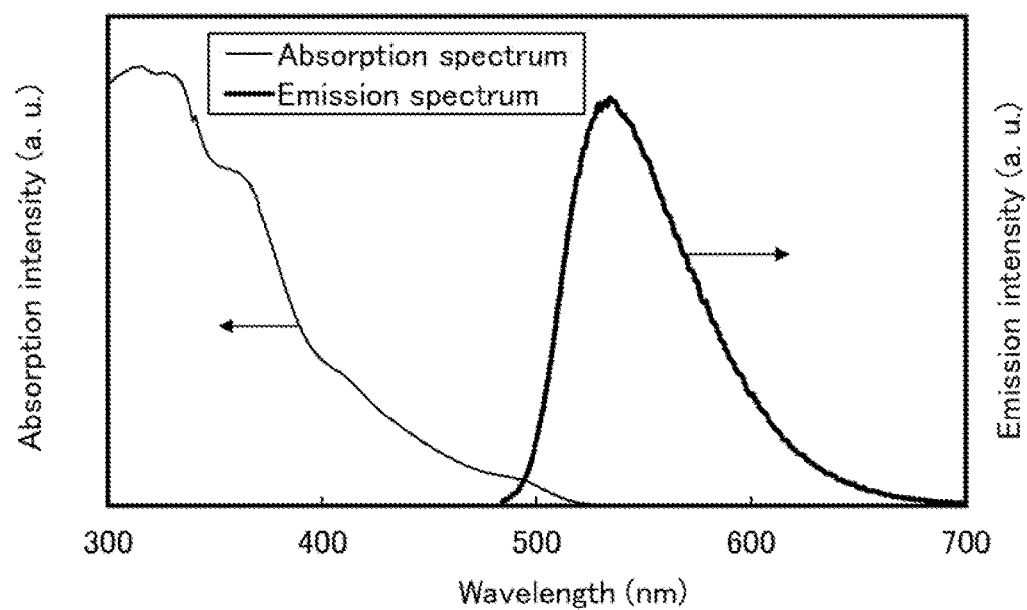
FIG. 16 shows an ultraviolet-visible absorption spectrum and an emission spectrum of Ir(tBupczpm)$_3$, which is an organometallic complex of one embodiment of the present invention, in a dichloromethane solution.

Next, an ultraviolet-visible absorption spectrum (absorption spectrum) and an emission spectrum of Ir(tBupczpm)₃ in a dichloromethane solution were measured. The absorption spectrum and the emission spectrum were measured using the same apparatus and method as Example 1. FIG. 16 shows measurement results of the absorption spectrum and the emission spectrum. The horizontal axis represents wavelength and the vertical axes represent absorption intensity and emission intensity. In FIG. 16, two solid lines are shown: a thin line represents the absorption spectrum, and a thick line represents the emission spectrum. The absorption spectrum in FIG. 16 is a result obtained by subtraction of a measured absorption spectrum of only dichloromethane that was put in a quartz cell from the measured absorption spectrum of the dichloromethane solution (0.055 mmol/L) in a quartz cell.

As shown in FIG. 16, Ir(tBupczpm)₃, which is the organometallic complex of one embodiment of the present invention, had an emission peak at 534 nm, and green light emission was observed from the dichloromethane solution.

Next, Ir(tBupczpm)₂(acac) obtained in this example was analyzed by LC/MS.

The LC/MS analysis was performed using the same measurement apparatus and measurement method as Example 1. Note that a sample was prepared in such a manner that Ir(tBupczpm)₃ was dissolved in chloroform at a given concentration and the mixture was diluted with acetonitrile. The injection amount was 5.0 μL.

In the LC separation, a gradient method in which the composition of mobile phases is changed was employed. The ratio of Mobile Phase A to Mobile Phase B was 70:30 for 0 to 1 minute after the start of the measurement, and then the composition was changed so that the ratio of Mobile Phase A to Mobile Phase B in the 10th minute was 95:5. The composition was changed linearly. In the MS analysis, ionization was carried out by ESI. At this time, the capillary voltage and the sample cone voltage were set to 3.0 kV and 30 V, respectively, and detection was performed in a positive mode. The mass range for the measurement was m/z=100 to 1500.

A component with m/z of 1321.51, which underwent the separation and the ionization under the above-described conditions, was collided with an argon gas in a collision cell to dissociate into product ions. The energy (collision energy) for the collision with argon was 70 eV. The detection results of the dissociated product ions by time-of-flight (TOF) MS are shown in FIG. 17.

Figure 17:
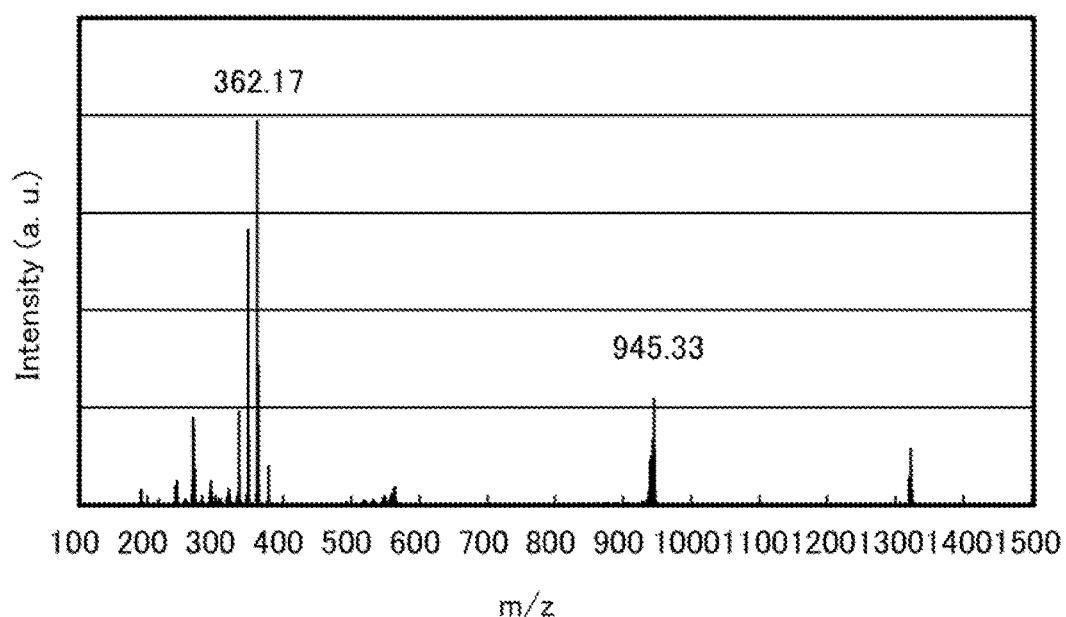
FIG. 17 shows LC/MS measurement results of Ir(tBupczpm)$_3$, which is the organometallic complex of one embodiment of the present invention.

The results in FIG. 17 show that product ions of Ir(tBupczpm)₃, which is the organometallic complex of one embodiment of the present invention represented by Structural Formula (112), were detected mainly around m/z=945.33 and around m/z=362.17. The results in FIG. 17 show characteristics derived from Ir(tBupczpm)₃ and can thus be regarded as important data in identification of Ir(tBupczpm)₃ contained in a mixture.

Example 4

Synthesis Example 4

In Synthesis Example 4, a method of synthesizing bis[3-(6-tert-butyl-4-pyrimidinyl-κN3)-9-ethyl-9H-carbazol-2-yl-κC](2,4-pentanedionato-κ²O,O')iridium(III) (abbreviation: Ir(tBueczpm)₂(acac)), which is the organometallic complex of one embodiment of the present invention represented by Structural Formula (110) and described in Embodiment 1, is specifically described.

<Method of Synthesizing Ir(tBueczpm)₂(Acac) Represented by Structural Formula (110)>

First, an example of a method of synthesizing Ir(tBueczpm)₂(acac) represented by Structural Formula (110) is described.

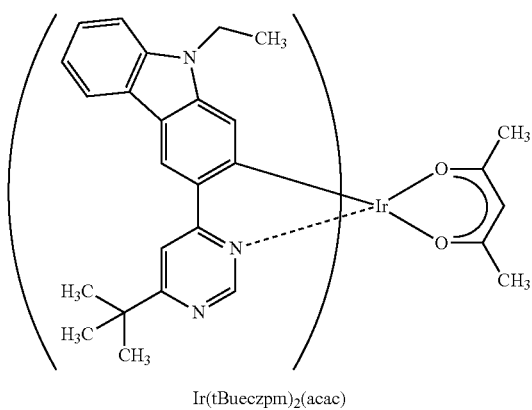

Ir(tBueczpm)₂(acac)

Step 1: Synthesis of
4-tert-butyl-6-hydroxypyrimidine

First, 7.2 g of formamidine acetate, 7.5 g of sodium methoxide, and 70 mL of methanol were put in a 100-mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was condensed, and the given residue was dissolved in water. The solution was subjected to extraction with ethyl acetate. The obtained solution of the extract was washed with saturated saline, and anhydrate magnesium sulfate was added to the organic layer for drying. The magnesium sulfate was removed by gravity filtration, and the filtrate was concentrated to give a solid. This solid was washed with ethyl acetate to give 4-tert-butyl-6-hydroxypyrimidine (white powder, yield of 49%). A synthesis scheme of Step 1 is shown in (h-1).

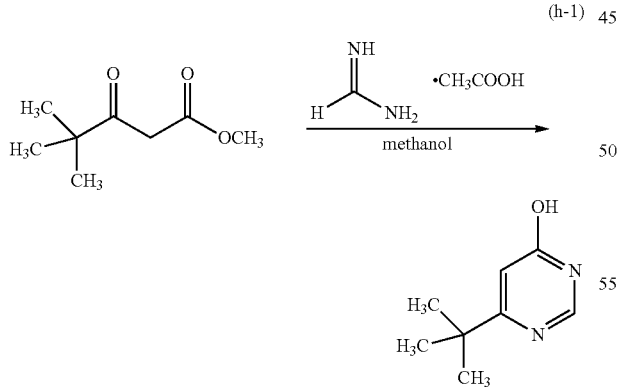

(h-1)

Step 2: Synthesis of 4-tert-butyl-6-chloropyrimidine

Next, 4.7 g of 4-tert-butyl-6-hydroxypyrimidine obtained in Step 1 and 14 mL of phosphoryl chloride were put into a 50-mL three-neck flask, and the mixture was heated and refluxed for 1.5 hours. After the reflux, phosphoryl chloride was distilled off under reduced pressure. The obtained residue was dissolved in dichloromethane, and washed with water and a saturated aqueous solution of sodium hydrogen carbonate. Anhydrate magnesium sulfate was added to the obtained organic layer for drying. The magnesium sulfate was removed by gravity filtration, and the filtrate was concentrated to give a solid. The obtained residue was purified by silica gel column chromatography using hexane and ethyl acetate as a developing solvent in a ratio of 10:1 to give 4-tert-butyl-6-chloropyrimidine (white powder, yield of 78%). A synthesis scheme of Step 2 is shown in (h-2).

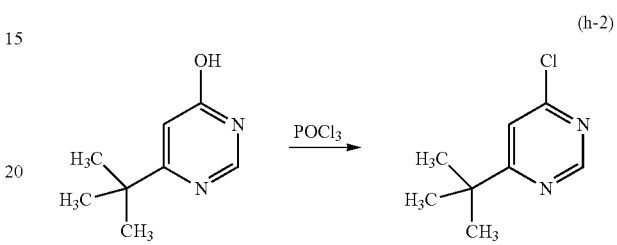

(h-2)

Step 3: Synthesis of 4-tert-butyl-6-(9-ethyl-9H-carbazol-3-yl)pyrimidine (Abbreviation: HtBueczpm)

Next, in a 100-mL round-bottom flask equipped with a reflux pipe were put 2.21 g of 4-tert-butyl-6-chloropyrimidine obtained in Step 2, 4.97 g of 9-ethyl-9H-carbazole-3-boronic acid pinacol ester, 20 mL of 1M aqueous solution of potassium acetate, 20 mL of 1M aqueous solution of sodium carbonate, and 50 mL of acetonitrile, and the air in the flask was replaced with argon. To this mixture, 0.78 g of tetrakis(triphenylphosphine)palladium(0) was added, and the flask was heated by being irradiated with microwaves (2.45 GHz, 400 W) for 2 hours. Then, water was added to this solution and the organic layer was extracted with dichloromethane. The obtained organic layer was washed with water and saturated saline, and was dried with magnesium sulfate. The solution after the drying was filtered to remove the magnesium sulfate. The solvent of this solution was distilled off, and then the given residue was purified by silica gel column chromatography using toluene and ethyl acetate as a developing solvent in a ratio of 4:1 to give HtBueczpm, which was an objective pyrimidine derivative (light yellow powder, yield of 71%). Note that the irradiation with microwaves was performed using a microwave synthesis system (MicroSYNTH, manufactured by MILESTONE Inc.). A synthesis scheme of Step 3 is shown in (h-3).

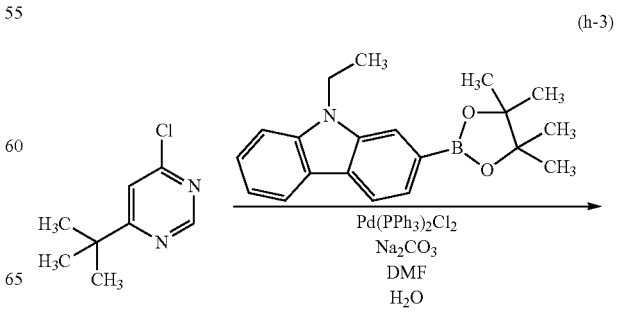

(h-3)

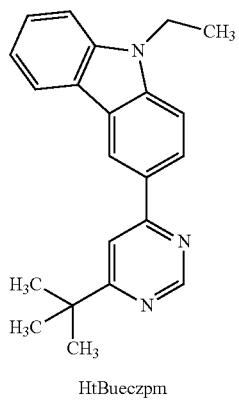

HtBueczpm

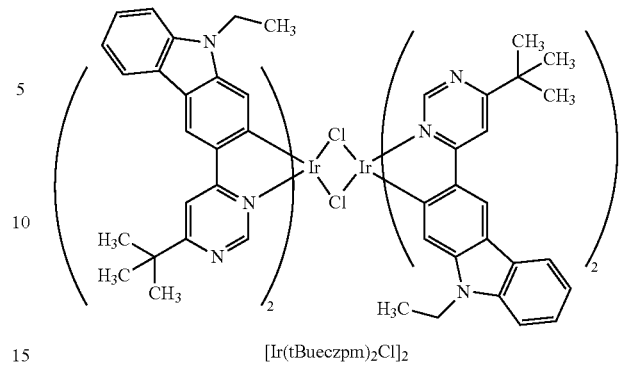

[Ir(tBueczpm)₂Cl]₂

Step 4: Synthesis of di-μ-chloro-tetrakis[3-(6-tert-butyl-4-pyrimidinyl-κN3)-9-ethyl-9H-carbazol-2-yl-κC]diiridium(III) (Abbreviation: [Ir(tBueczpm)₂Cl]₂)

Next, in a recovery flask equipped with a reflux pipe were put 30 mL of 2-ethoxyethanol, 10 mL of water, 1.96 g of HtBueczpm (abbreviation) obtained in Step 3, and 0.90 g of iridium chloride hydrate (IrCl₃.H₂O) (produced by Sigma-Aldrich Corporation), and the air in the flask was replaced with argon. After that, irradiation with microwaves (2.45 GHz, 100 W) was performed for 1 hour to cause a reaction. The solvent was distilled off, and then the given residue was suction-filtered and washed with ethanol to give [Ir(tBueczpm)₂Cl]₂ (abbreviation), a dinuclear complex (brown powder, yield of 68%). A synthesis scheme of Step 4 is shown in (h-4).

Step 5: Synthesis of Ir(tBueczpm)₂(acac)

Furthermore, in a recovery flask equipped with a reflux pipe were put 20 mL of 2-ethoxyethanol, 0.88 g of [Ir(tBueczpm)₂Cl]₂ that is the dinuclear complex obtained in Step 4, 0.15 g of acetylacetone (abbreviation: Hacac), and 0.53 g of sodium carbonate, and the air in the flask was replaced with argon. After that, the mixture was heated by irradiation with microwaves (2.45 GHz, 120 W) for 60 minutes. The solvent was distilled off, and the given residue was suction-filtered with ethanol. The obtained solid was washed with water and ethanol. The obtained solid was dissolved in dichloromethane and filtered through a filter aid in which Celite, alumina, and Celite were stacked in this order. Then, recrystallization was carried out with a mixed solvent of dichloromethane and ethanol; thus, Ir(tBueczpm)₂(acac), which is the organometallic complex of one embodiment of the present invention, was obtained as yellow orange powder (yield: 42%). A synthesis scheme of Step 5 is shown in (h-5).

(h-4)

2 IrCl₃·H₂O +

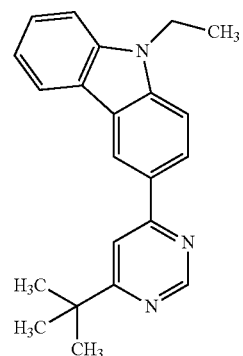

HtBueczpm

→ 2-ethoxyethanol/H₂O (h-5)

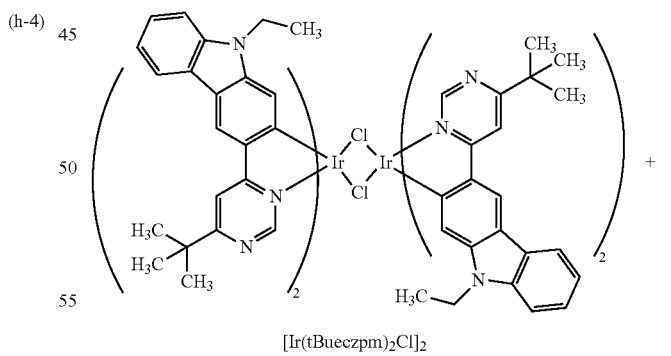

[Ir(tBueczpm)₂Cl]₂

+

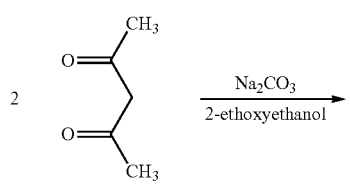

→ Na₂CO₃ / 2-ethoxyethanol

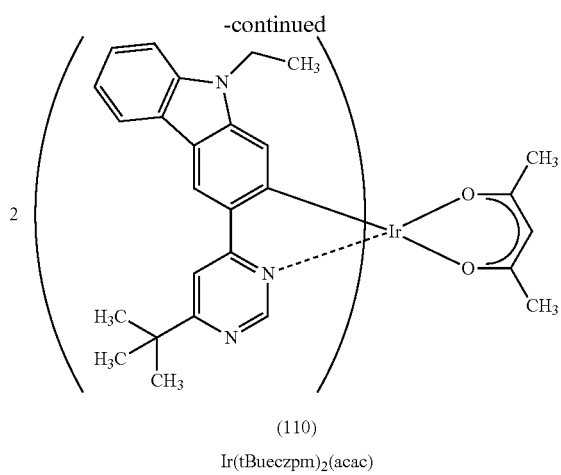

(110)

Ir(tBueczpm)₂(acac)

Figure 18:
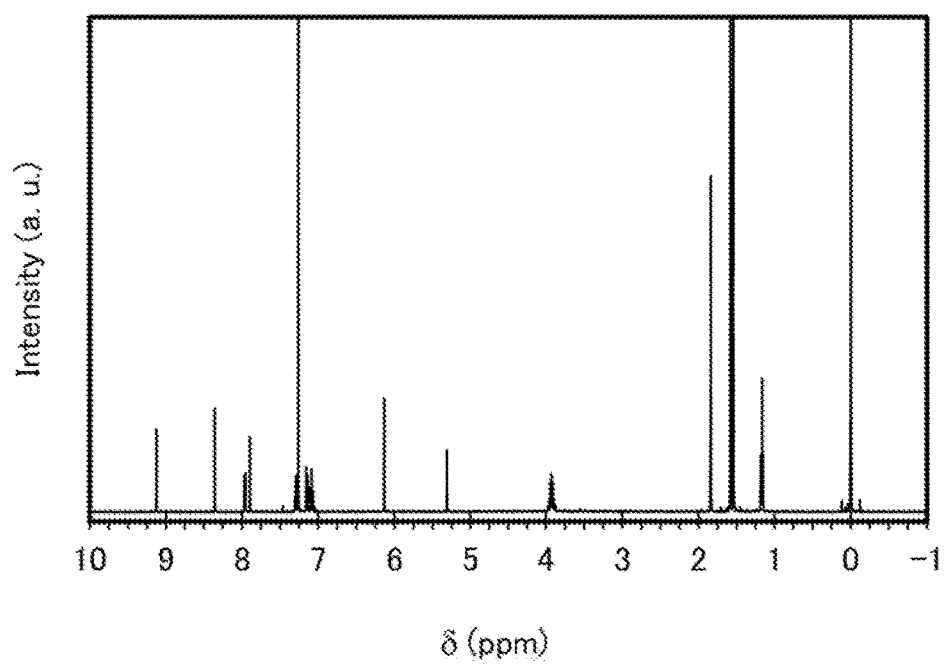
FIG. 18 is a ¹H-NMR chart of an organometallic complex synthesized in Example 4.

Results of analysis of the yellow orange powder obtained in Step 5 by nuclear magnetic resonance spectrometry (¹H-NMR) are shown below. FIG. 18 is a ¹H-NMR chart. The results revealed that Ir(tBueczpm)₂(acac), which is the organometallic complex of one embodiment of the present invention represented by Structural Formula (110), was obtained in Synthesis Example 4.

¹H-NMR. δ (CDCl₃): 1.16 (t, 6H), 1.58 (s, 18H), 1.84 (s, 6H), 3.90-3.96 (m, 4H), 5.32 (s, 1H), 6.14 (s, 2H), 7.09 (t, 2H), 7.15 (d, 2H), 7.29 (t, 2H), 7.90 (s, 2H), 7.96 (d, 2H), 8.35 (s, 2H), 9.13 (s, 2H).

Figure 19:
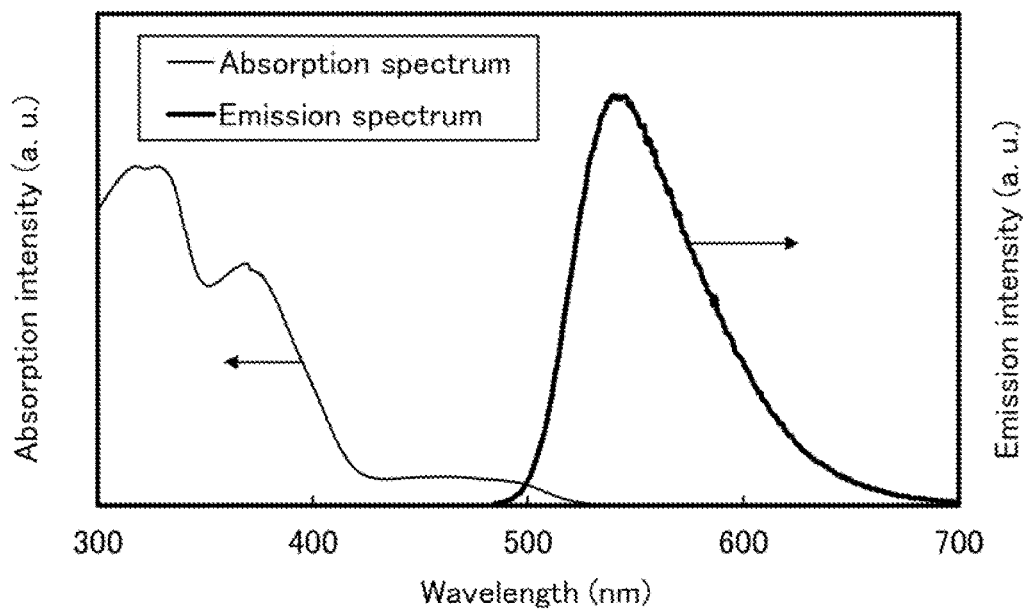
FIG. 19 shows an ultraviolet-visible absorption spectrum and an emission spectrum of Ir(tBueczpm)$_2$(acac), which is an organometallic complex of one embodiment of the present invention, in a dichloromethane solution.

Next, an ultraviolet-visible absorption spectrum (absorption spectrum) and an emission spectrum of Ir(tBueczpm)₂(acac) in a dichloromethane solution were measured. The absorption spectrum and the emission spectrum were measured using the same apparatus and method as Example 1. FIG. 19 shows measurement results of the absorption spectrum and the emission spectrum. The horizontal axis represents wavelength and the vertical axes represent absorption intensity and emission intensity. In FIG. 19, two solid lines are shown: a thin line represents the absorption spectrum, and a thick line represents the emission spectrum. The absorption spectrum in FIG. 19 is a result obtained by subtraction of a measured absorption spectrum of only dichloromethane that was put in a quartz cell from the measured absorption spectrum of the dichloromethane solution (0.070 mmol/L) in a quartz cell.

As shown in FIG. 19, Ir(tBueczpm)₂(acac), which is the organometallic complex of one embodiment of the present invention, had an emission peak at 540 nm, and yellow green light emission was observed from the dichloromethane solution.

Next, Ir(tBueczpm)₂(acac) obtained in this example was analyzed by LC/MS.

The LC/MS analysis was performed using the same measurement apparatus and measurement method as Example 1. Note that a sample was prepared in such a manner that Ir(tBueczpm)₂(acac) was dissolved in chloroform at a given concentration and the mixture was diluted with acetonitrile. The injection amount was 5.0 μL.

In the LC separation, a gradient method in which the composition of mobile phases is changed was employed. The ratio of Mobile Phase A to Mobile Phase B was 70:30 for 0 to 1 minute after the start of the measurement, and then the composition was changed so that the ratio of Mobile Phase A to Mobile Phase B in the 10th minute was 95:5. The composition was changed linearly. In the MS analysis, ionization was carried out by ESI. At this time, the capillary voltage and the sample cone voltage were set to 3.0 kV and 30 V, respectively, and detection was performed in a positive mode. The mass range for the measurement was m/z=100 to 1200.

A component with m/z of 948.37, which underwent the separation and the ionization under the above-described conditions, was collided with an argon gas in a collision cell to dissociate into product ions. The energy (collision energy) for the collision with argon was 30 eV. The detection results of the dissociated product ions by time-of-flight (TOF) MS are shown in FIG. 20.

Figure 20:
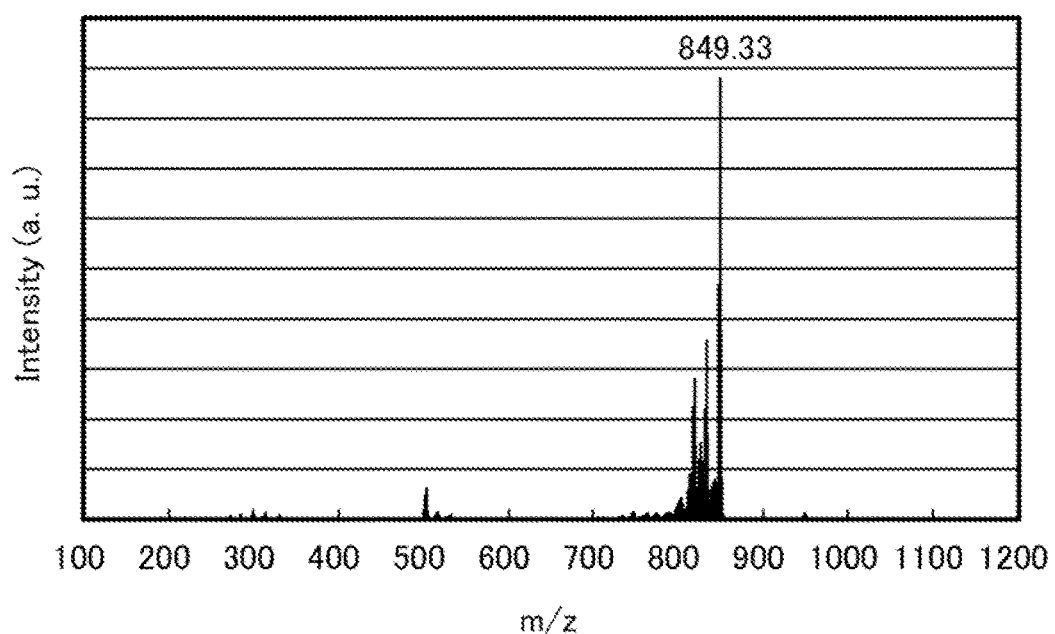
FIG. 20 shows LC/MS measurement results of Ir(tBueczpm)$_2$(acac), which is the organometallic complex of one embodiment of the present invention.

The results in FIG. 20 show that a product ion of Ir(tBueczpm)₂(acac), which is the organometallic complex of one embodiment of the present invention represented by Structural Formula (100), was detected mainly around m/z=849.33. The results in FIG. 20 show characteristics derived from Ir(tBueczpm)₂(acac) and can thus be regarded as important data in identification of Ir(tBueczpm)₂(acac) contained in a mixture.

Example 5

Synthesis Example 5

In Synthesis Example 5, a method of synthesizing tris[3-(6-tert-butyl-4-pyrimidinyl-κN3)-9-ethyl-9H-carbazol-2-yl-κC]iridium(III) (abbreviation: Ir(tBueczpm)₃), which is the organometallic complex of one embodiment of the present invention represented by Structural Formula (113) and described in Embodiment 1, is specifically described.

<Method of Synthesizing Ir(tBueczpm)₃ Represented by Structural Formula (113)>

First, an example of a method of synthesizing Ir(tBueczpm)₃ represented by Structural Formula (113) is described.

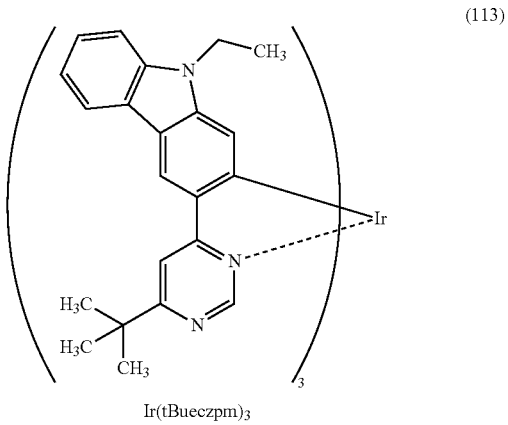

(113)

Ir(tBueczpm)₃

Step 1: Synthesis of
4-tert-butyl-6-hydroxypyrimidine

First, 7.2 g of formamidine acetate, 7.5 g of sodium methoxide, and 70 mL of methanol were put in a 100-mL three-neck flask. Then, 10 g of methyl 4,4-dimethyloxovalerate was added to this mixed solution. The mixture was stirred at room temperature for 24 hours. After a predetermined time elapsed, a mixed solution of 17 mL of water and 7.2 mL of acetic acid was added to the mixture, and the mixture was stirred at room temperature. This mixture was condensed, and the given residue was dissolved in water. The solution was subjected to extraction with ethyl acetate. The obtained solution of the extract was washed with saturated saline, and anhydrate magnesium sulfate was added to the organic layer for drying. The magnesium sulfate was removed by gravity filtration, and the filtrate was concentrated to give a solid. This solid was washed with ethyl acetate to give 4-tert-butyl-6-hydroxypyrimidine (white powder, yield of 49%). A synthesis scheme of Step 1 is shown in (j-1).

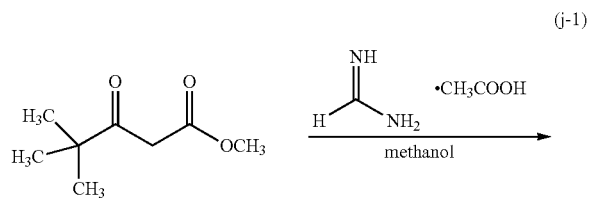

(j-1)

Step 2: Synthesis of 4-tert-butyl-6-chloropyrimidine

Next, 4.7 g of 4-tert-butyl-6-hydroxypyrimidine obtained in Step 1 and 14 mL of phosphoryl chloride were put into a 50-mL three-neck flask, and the mixture was heated and refluxed for 1.5 hours. After the reflux, phosphoryl chloride was distilled off under reduced pressure. The obtained residue was dissolved in dichloromethane, and washed with water and a saturated aqueous solution of sodium hydrogen carbonate. Anhydrate magnesium sulfate was added to the obtained organic layer for drying. The magnesium sulfate was removed by gravity filtration, and the filtrate was concentrated to give a solid. The obtained residue was purified by silica gel column chromatography using hexane and ethyl acetate as a developing solvent in a ratio of 10:1 to give 4-tert-butyl-6-chloropyrimidine (white powder, yield of 78%). A synthesis scheme of Step 2 is shown in (j-2).

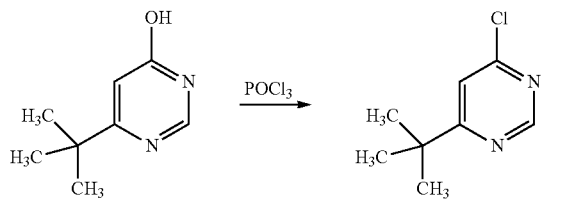

(j-2)

Step 3: Synthesis of 4-tert-butyl-6-(9-ethyl-9H-carbazol-3-yl)pyrimidine (abbreviation: HtBueczpm)

Next, in a 100-mL round-bottom flask equipped with a reflux pipe were put 2.21 g of 4-tert-butyl-6-chloropyrimidine obtained in Step 2, 4.97 g of 9-ethyl-9H-carbazole-3-boronic acid pinacol ester, 20 mL of 1M aqueous solution of potassium acetate, 20 mL of 1M aqueous solution of sodium carbonate, and 50 mL of acetonitrile, and the air in the flask was replaced with argon. To this mixture, 0.78 g of tetrakis(triphenylphosphine)palladium(0) was added, and the flask was heated by being irradiated with microwaves (2.45 GHz, 400 W) for 2 hours. Then, water was added to this solution and the organic layer was extracted with dichloromethane. The obtained organic layer was washed with water and saturated saline, and was dried with magnesium sulfate. The solution after the drying was filtered to remove the magnesium sulfate. The solvent of this solution was distilled off, and then the given residue was purified by silica gel column chromatography using toluene and ethyl acetate as a developing solvent in a ratio of 4:1 to give HtBueczpm, which was an objective pyrimidine derivative (light yellow powder, yield of 71%). Note that the irradiation with microwaves was performed using a microwave synthesis system (MicroSYNTH, manufactured by MILESTONE Inc.). A synthesis scheme of Step 3 is shown in (j-3).

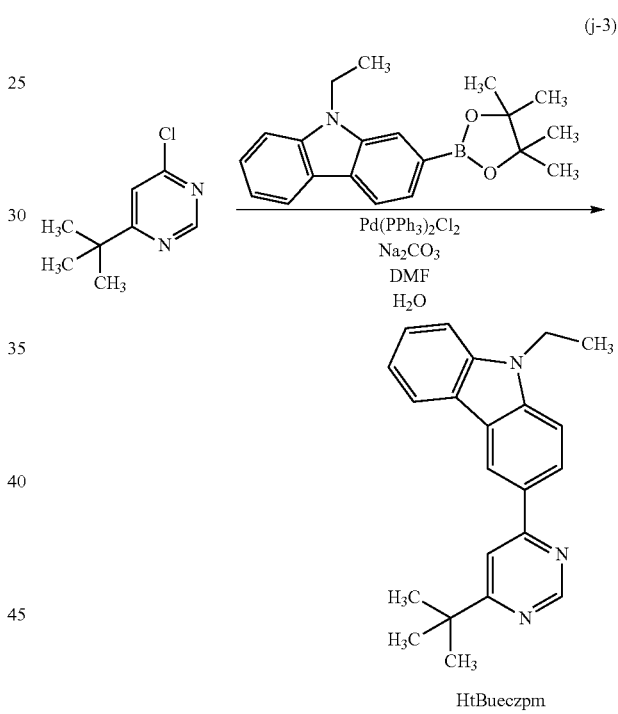

(j-3)

Step 4: Synthesis of di-μ-chloro-tetrakis[3-(6-tert-butyl-4-pyrimidinyl-κN3)-9-ethyl-9H-carbazol-2-yl-κC]diiridium(III) (Abbreviation: [Ir(tBueczpm)$_2$Cl]$_2$)

Next, in a recovery flask equipped with a reflux pipe were put 30 mL of 2-ethoxyethanol, 10 mL of water, 1.96 g of HtBueczpm obtained in Step 3, and 0.90 g of iridium chloride hydrate (IrCl$_3$—H$_2$O) (produced by Sigma-Aldrich Corporation), and the air in the flask was replaced with argon. After that, irradiation with microwaves (2.45 GHz, 100 W) was performed for 1 hour to cause a reaction. The solvent was distilled off, and then the given residue was suction-filtered and washed with ethanol to give [Ir(tBueczpm)$_2$Cl]$_2$, a dinuclear complex (brown powder, yield of 68%). A synthesis scheme of Step 4 is shown in (j-4).

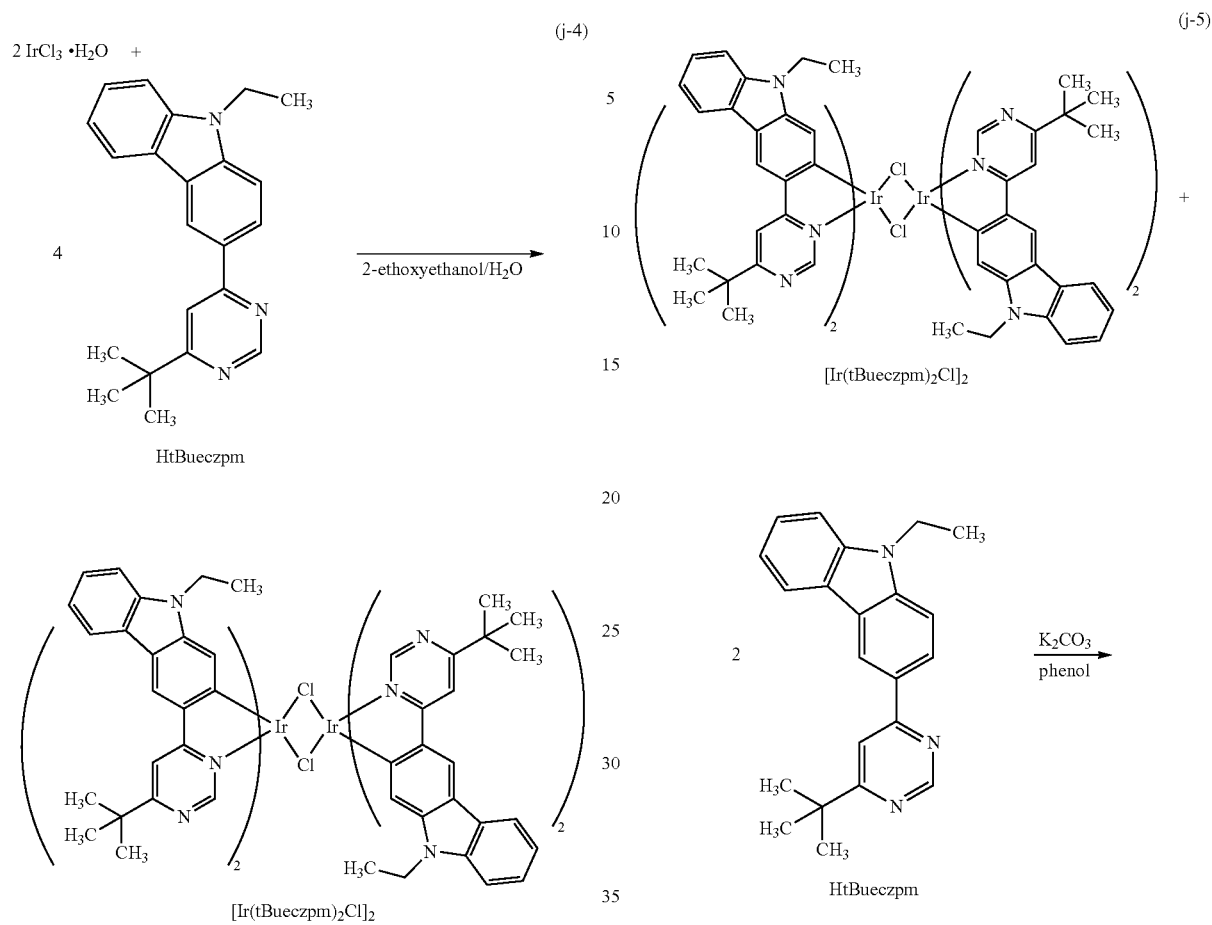

Step 5: Synthesis of Ir(tBueczpm)₃

Furthermore, in a 200 mL three-neck flask equipped with a reflux pipe were put 8 g of phenol, 0.89 g of [Ir(tBueczpm)₂Cl]₂ that is the dinuclear complex obtained in Step 4, 0.82 g of HtBueczpm, and 0.69 g of potassium carbonate, and the air in the flask was replaced with nitrogen. After that, the mixture was heated at 185° C. for 9 hours to be reacted. The obtained residue was irradiated with ultrasonic waves and suction-filtered in methanol. The obtained solid was dissolved in dichloromethane and washed with water and saturated saline. The obtained organic layer was dried with magnesium sulfate, and the solution after the drying was filtered to remove the magnesium sulfate. The solvent of this solution was distilled off, and the obtained residue was dissolved in dichloromethane and filtered through Celite/alumina/Celite. Then, recrystallization was carried out with a mixed solvent of dichloromethane and ethanol; thus, Ir(tBueczpm)₃, which is the organometallic complex of one embodiment of the present invention, was obtained as a yellow powder (yield: 59%). A synthesis scheme of Step 5 is shown in (j-5).

Figure 21:
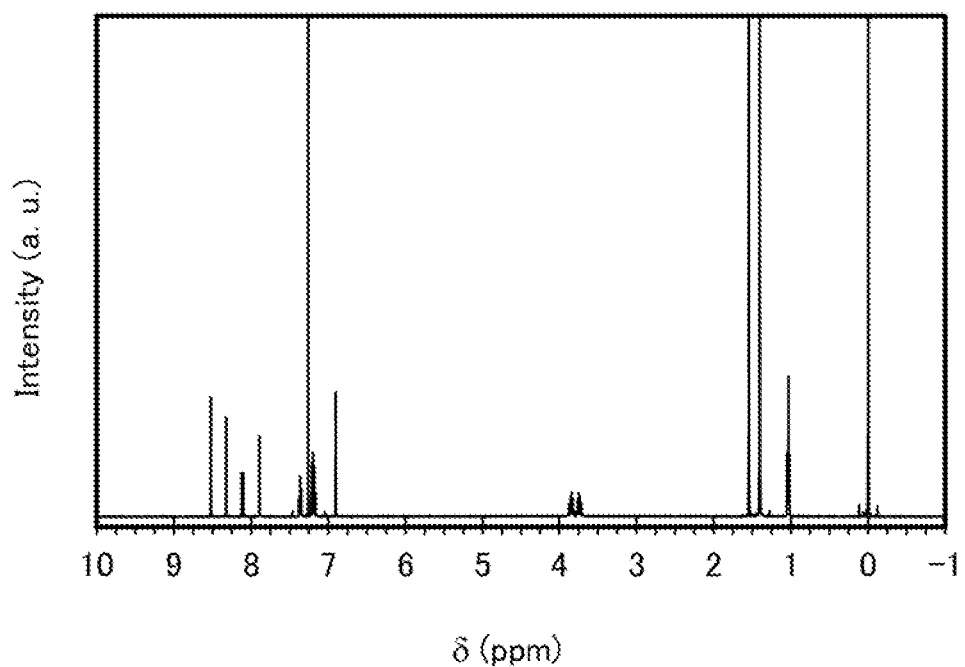
FIG. 21 is a ¹H-NMR chart of an organometallic complex synthesized in Example 5.

Results of analysis of the yellow powder obtained in Step 5 by nuclear magnetic resonance spectrometry ($^1$H-NMR) are shown below. FIG. 21 is a $^1$H-NMR chart. The results revealed that Ir(tBueczpm)₃, which is the organometallic complex of one embodiment of the present invention represented by Structural Formula (113), was obtained in Synthesis Example 5.

$^1$H-NMR. δ (CDCl$_3$): 1.03 (t, 9H), 1.41 (s, 27H), 3.70-3.78 (m, 3H), 3.82-3.89 (m, 3H), 6.91 (s, 3H), 7.17-7.22 (m, 6H), 7.37 (t, 3H), 7.89 (s, 3H), 8.11 (d, 3H), 8.32 (s, 3H), 8.52 (s, 3H).

Figure 22:
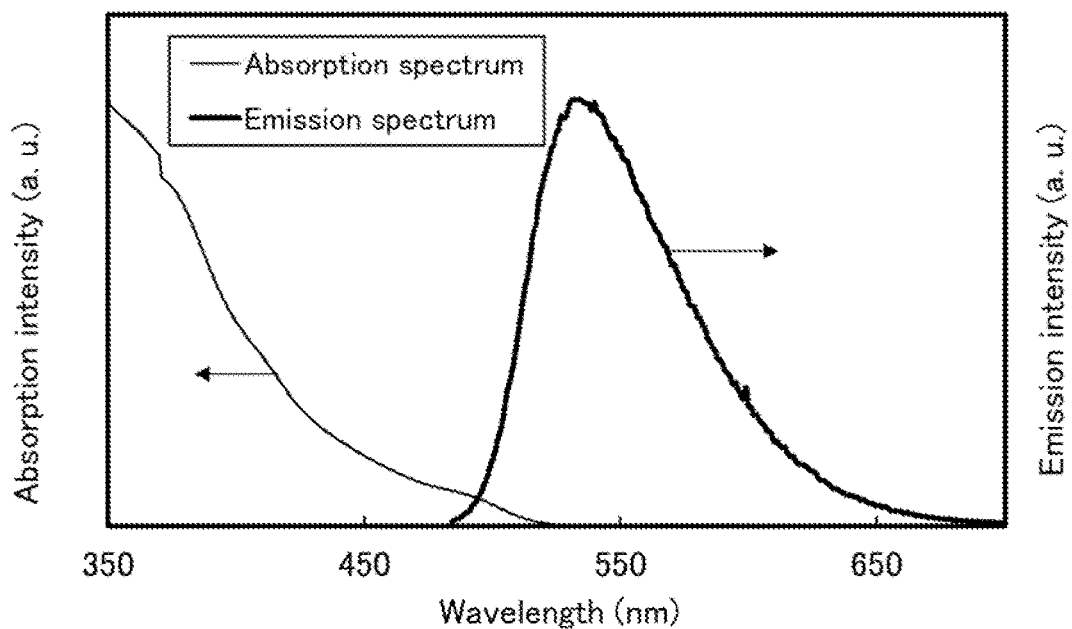
FIG. 22 shows an ultraviolet-visible absorption spectrum and an emission spectrum of Ir(tBueczpm)$_3$, which is an organometallic complex of one embodiment of the present invention, in a dichloromethane solution.

Next, an ultraviolet-visible absorption spectrum (absorption spectrum) and an emission spectrum of Ir(tBueczpm)$_3$ in a dichloromethane solution were measured. The absorption spectrum and the emission spectrum were measured using the same apparatus and method as Example 1. FIG. 22 shows measurement results of the absorption spectrum and the emission spectrum. The horizontal axis represents wavelength and the vertical axes represent absorption intensity and emission intensity. In FIG. 22, two solid lines are shown: a thin line represents the absorption spectrum, and a thick line represents the emission spectrum. Note that the absorption spectrum in FIG. 22 is a result obtained by subtraction of a measured absorption spectrum of only dichloromethane that was put in a quartz cell from the measured absorption spectrum of the dichloromethane solution (0.059 mmol/L) in a quartz cell.

As shown in FIG. 22, Ir(tBueczpm)$_3$, which is the organometallic complex of one embodiment of the present invention, had an emission peak at 532 nm, and green light emission was observed from the dichloromethane solution.

Next, Ir(tBueczpm)$_3$ obtained in this example was analyzed by LC/MS.

The LC/MS analysis was performed using the same measurement apparatus and measurement method as Example 1. Note that a sample was prepared in such a manner that Ir(tBueczpm)$_3$ was dissolved in chloroform at a given concentration and the mixture was diluted with acetonitrile. The injection amount was 5.0 μL.

The LC separation was performed using the same method as Example 1. In the MS analysis, ionization was carried out by ESI. At this time, the capillary voltage and the sample cone voltage were set to 3.0 kV and 30 V, respectively, and detection was performed in a positive mode. The mass range for the measurement was m/z=100 to 1200.

A component with m/z of 1178.51, which underwent the separation and the ionization under the above-described conditions, was collided with an argon gas in a collision cell to dissociate into product ions. The energy (collision energy) for the collision with argon was 70 eV. The detection results of the dissociated product ions by time-of-flight (TOF) MS are shown in FIG. 23.

Figure 23:
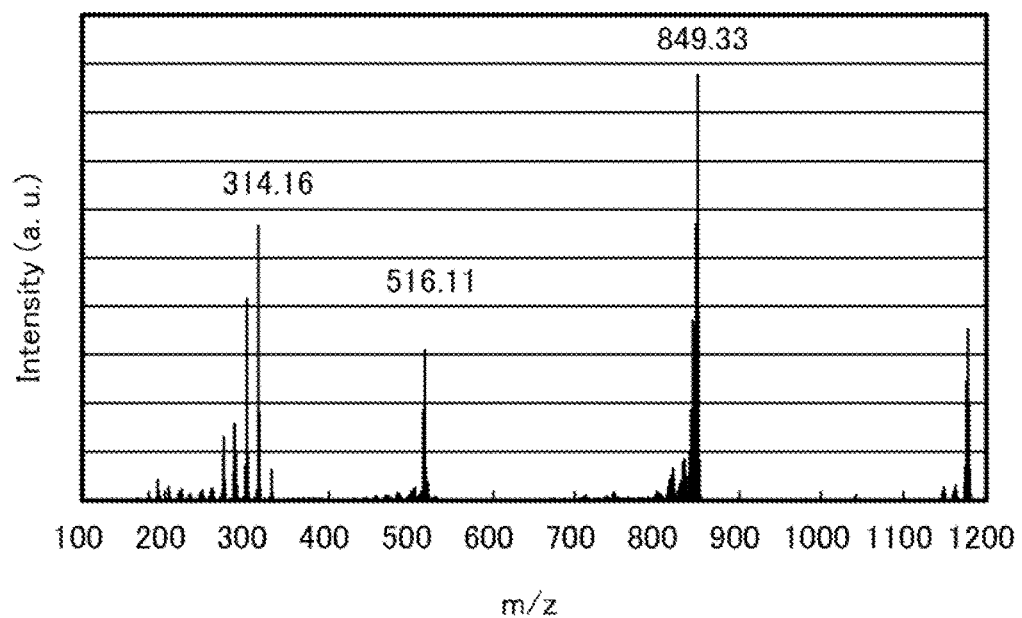
FIG. 23 shows LC/MS measurement results of Ir(tBueczpm)$_3$, which is the organometallic complex of one embodiment of the present invention.

The results in FIG. 23 show that product ions of Ir(tBueczpm)$_2$(acac), which is the organometallic complex of one embodiment of the present invention represented by Structural Formula (113), were detected mainly around m/z=849.33, around m/z=516.11, and around m/z=314.16. The results in FIG. 23 show characteristics derived from Ir(tBueczpm)$_3$ and can thus be regarded as important data in identification of Ir(tBueczpm)$_3$ contained in a mixture.

Example 6

Figure 24A:
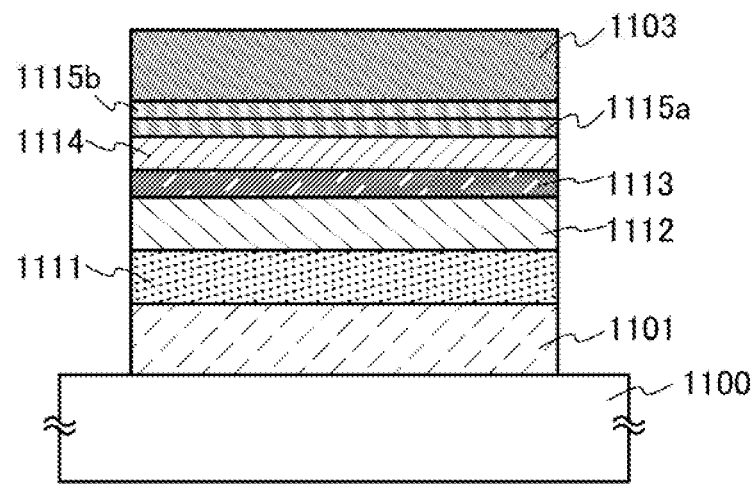
FIGS. 24A and 24B illustrate light-emitting elements in Example 6 and Example 7.

In this example, light-emitting elements (light-emitting elements 1 to 5) of one embodiment of the present invention are described with reference to FIG. 24A. Chemical formulae of materials used in this example are shown below.

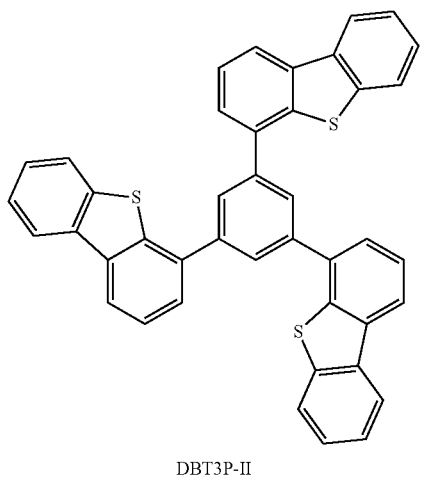

DBT3P-II

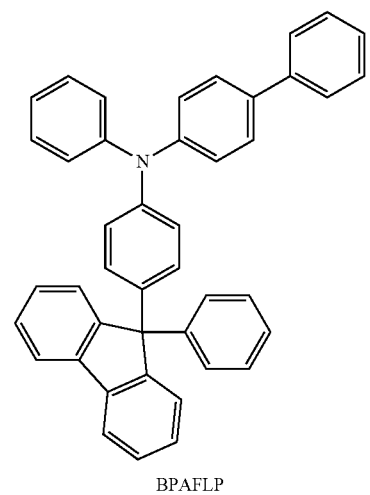

BPAFLP

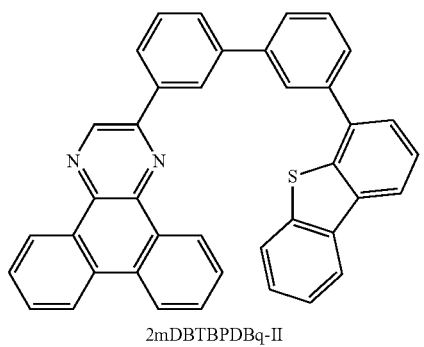

2mDBTBPDBq-II

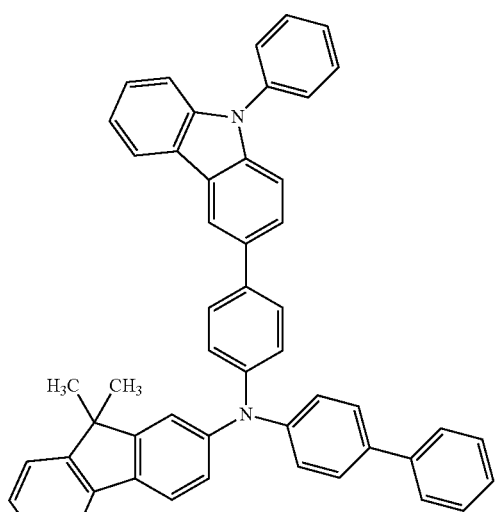
PCBBiF
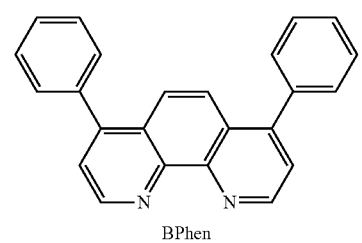
BPhen
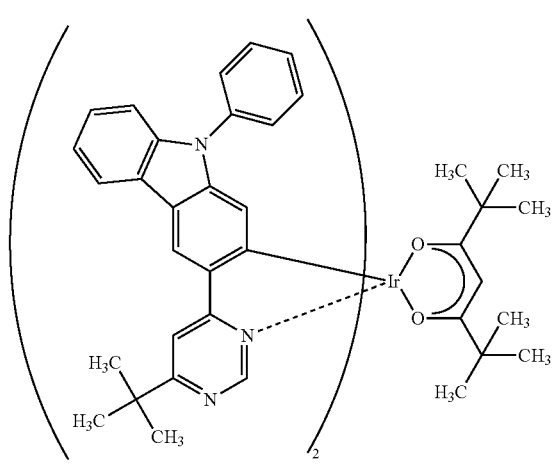
Ir(tBupczpm)₂(dpm)
(101)
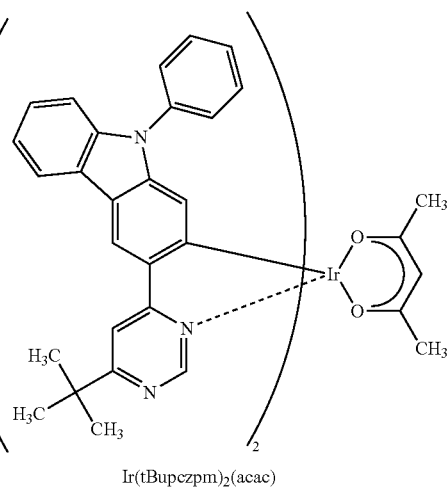
Ir(tBupczpm)₂(acac)
(113)
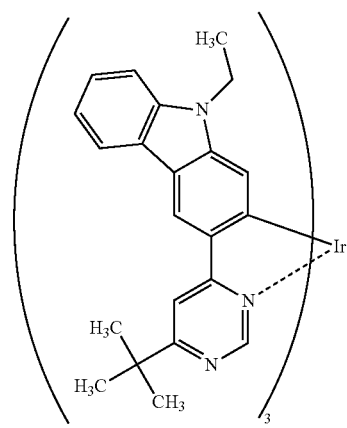
Ir(tBueczpm)₃
(112)
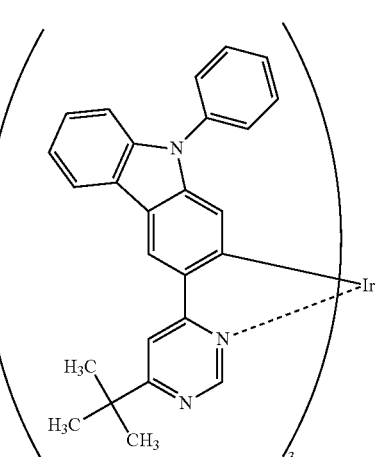
Ir(tBupczpm)₃

-continued

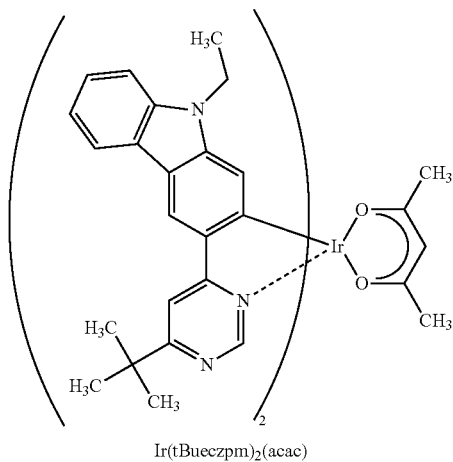

(110)

Ir(tBueczpm)₂(acac)

A method for manufacturing the light-emitting element 1 of this example is described below.
(Light-Emitting Element 1)

First, an indium oxide-tin oxide compound containing silicon or silicon oxide (ITO-SiO₂, hereinafter abbreviated to ITSO) was deposited by a sputtering method over a substrate 1100, so that a first electrode 1101 was formed. Note that the composition ratio of In₂O₃ to SnO₂ and SiO₂ in the target used was 85:10:5 [wt %]. The thickness of the first electrode 1101 was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed, baked at 200° C. for 1 hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface on which the first electrode 1101 was provided faced downward. The pressure in the vacuum evaporation apparatus was reduced to about $10^{-4}$ Pa. Then, 4,4',4''-(benzene-1,3,5-triyl)tri(dibenzothiophene) (abbreviation: DBT3P-II) and molybdenum oxide were deposited by co-evaporation, so that a hole-injection layer 1111 was formed on the first electrode 1101. The thickness of the hole-injection layer 1111 was 20 nm. The weight ratio of DBT3P-II to molybdenum oxide was adjusted to 4:2 (=DBT3P-II: molybdenum oxide).

Next, on the hole-injection layer 1111, 4-phenyl-4'-(9-phenylfluoren-9-yl)triphenylamine (abbreviation: BPAFLP) was deposited to a thickness of 20 nm, so that a hole-transport layer 1112 was formed.

In addition, on the hole-transport layer 1112, 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluor en-2-amine (abbreviation: PCBBiF), and Ir(tBupczpm)₂(dpm) synthesized in Example 1 were deposited by co-evaporation, so that a light-emitting layer 1113 was formed. Here, the weight ratio of 2mDBTBPDBq-II to PCBBiF and Ir(tBupczpm)₂(dpm) was adjusted to 0.8:0.2: 0.05 (=2mDBTBPDBq-II: PCBBiF: Ir(tBupczpm)₂(dpm)). The thickness of the light-emitting layer 1113 was 40 nm.

Note that in the light-emitting layer 1113 of the light-emitting element 1, 2mDBTBPDBq-II served as a host material, PCBBiF served as an assist material, and Ir(tBupczpm)₂(dpm) served as a guest material (dopant). Note that Ir(tBupczpm)₂(dpm) is the organometallic complex of one embodiment of the present invention.

Then, on the light-emitting layer 1113, 2mDBTBPDBq-II was deposited to a thickness of 10 nm, so that an electron-transport layer 1114 was formed.

Then, on the electron-transport layer 1114, bathophenanthroline (abbreviation: BPhen) was deposited to a thickness of 15 nm, so that a first electron-injection layer 1115a was formed.

Furthermore, on the first electron-injection layer 1115a, lithium fluoride (LiF) was deposited by evaporation to a thickness of 1 nm, so that a second electron-injection layer 1115b was formed.

Lastly, aluminum was deposited by evaporation to a thickness of 200 nm, so that a second electrode 1103 functioning as a cathode was formed. Thus, the light-emitting element 1 of this example was manufactured.
(Light-Emitting Element 2)

The light-emitting element 2 is different from the light-emitting element 1 in the light-emitting layer 1113, the electron-transport layer 1114, and the first electron-injection layer 1115a. The details are described below.

The light-emitting layer 1113 of the light-emitting element 2 was formed by depositing 2mDBTBPDBq-II, PCBBiF, and Ir(tBupczpm)₂(acac) synthesized in Example 2 by co-evaporation. Note that the weight ratio of 2mDBTBPDBq-II to PCBBiF and Ir(tBupczpm)₂(acac) was adjusted to 0.8:0.2:0.05 (=2mDBTBPDBq-II: PCBBiF: Ir(tBupczpm)₂(acac)). The thickness of the light-emitting layer 1113 was 40 nm.

Note that in the light-emitting layer 1113 of the light-emitting element 2, 2mDBTBPDBq-II served as a host material, PCBBiF served as an assist material, and Ir(tBupczpm)₂(acac) served as a guest material (dopant). Note that Ir(tBupczpm)₂(acac) is the organometallic complex of one embodiment of the present invention.

As the electron-transport layer 1114 of the light-emitting element 2, 2mDBTBPDBq-II deposited to a thickness of 15 nm was used.

As the first electron-injection layer 1115a of the light-emitting element 2, BPhen deposited to a thickness of 10 nm was used.
(Light-Emitting Element 3)

The light-emitting element 3 is different from the light-emitting element 1 in the light-emitting layer 1113, the electron-transport layer 1114, and the first electron-injection layer 1115a. The details are described below.

The light-emitting layer 1113 of the light-emitting element 3 was formed by depositing 2mDBTBPDBq-II, PCBBiF, and Ir(tBueczpm)₂(acac) synthesized in Example 4 by co-evaporation. Note that the weight ratio of 2mDBTBPDBq-II to PCBBiF and Ir(tBueczpm)₂(acac) was adjusted to 0.8:0.2:0.025 (=2mDBTBPDBq-II:PCBBiF:Ir(tBueczpm)₂(acac)). The thickness of the light-emitting layer 1113 was 40 nm.

Note that in the light-emitting layer 1113 of the light-emitting element 3, 2mDBTBPDBq-II served as a host material, PCBBiF served as an assist material, and Ir(tBueczpm)₂(acac) served as a guest material (dopant). Note that Ir(tBueczpm)$_2$(acac) is the organometallic complex of one embodiment of the present invention.

As the electron-transport layer 1114 of the light-emitting element 3, 2mDBTBPDBq-II deposited to a thickness of 15 nm was used.

As the first electron-injection layer 1115*a* of the light-emitting element 3, BPhen deposited to a thickness of 10 nm was used.

(Light-Emitting Element 4)

The light-emitting element 4 is different from the light-emitting element 1 in the light-emitting layer 1113, the electron-transport layer 1114, and the first electron-injection layer 1115*a*. The details are described below.

The light-emitting layer 1113 of the light-emitting element 4 was formed by depositing 2mDBTBPDBq-II, PCBBiF, and Ir(tBueczpm)$_3$ synthesized in Example 5 by co-evaporation. Note that the weight ratio of 2mDBTBPDBq-II to PCBBiF and Ir(tBueczpm)$_3$ was adjusted to 0.8:0.2:0.025 (=2mDBTBPDBq-II:PCBBiF:Ir(tBueczpm)$_3$). The thickness of the light-emitting layer 1113 was 40 nm.

Note that in the light-emitting layer 1113 of the light-emitting element 4, 2mDBTBPDBq-II served as a host material, PCBBiF served as an assist material, and Ir(tBueczpm)$_3$ served as a guest material (dopant). Note that Ir(tBueczpm)$_3$ is the organometallic complex of one embodiment of the present invention.

As the electron-transport layer 1114 of the light-emitting element 4, 2mDBTBPDBq-II deposited to a thickness of 15 nm was used.

As the first electron-injection layer 1115*a* of the light-emitting element 4, BPhen deposited to a thickness of 10 nm was used.

(Light-Emitting Element 5)

The light-emitting element 5 is different from the light-emitting element 1 in the light-emitting layer 1113, the electron-transport layer 1114, and the first electron-injection layer 1115*a*. The details are described below.

The light-emitting layer 1113 of the light-emitting element 5 was formed by depositing 2mDBTBPDBq-II and Ir(tBupczpm)$_3$ synthesized in Example 3 by co-evaporation. Note that the weight ratio of 2mDBTBPDBq-II to Ir(tBupczpm)$_3$ was adjusted to 1:0.05 (=2mDBTBPDBq-II:Ir(tBupczpm)$_3$). The thickness of the light-emitting layer 1113 was 40 nm.

Note that in the light-emitting layer 1113 of the light-emitting element 5, 2mDBTBPDBq-II served as a host material and Ir(tBupczpm)$_3$ served as a guest material (dopant). Note that Ir(tBupczpm)$_3$ is the organometallic complex of one embodiment of the present invention. As described above, PCBBiF that was the assist material was not used in the light-emitting layer 1113 of the light-emitting element 5, unlike in those of the light-emitting elements 1 to 4.

As the electron-transport layer 1114 of the light-emitting element 5, 2mDBTBPDBq-II deposited to a thickness of 15 nm was used.

As the first electron-injection layer 1115*a* of the light-emitting element 5, BPhen deposited to a thickness of 10 nm was used.

Note that structures of the other components (the first electrode 1101, the hole-injection layer 1111, the hole-transport layer 1112, the second electron-injection layer 1115*b*, and the second electrode 1103) of the light-emitting elements 2 to 5 are the same as those of the light-emitting element 1; therefore, the above description can be referred to.

Table 1 shows element structures of the light-emitting elements 1 to 5 obtained as described above.

TABLE 1

| | Anode | Hole-injection layer | Hole-transport layer | Light-emitting layer | Electron-transport layer | First electron-injection layer | Second electron-injection layer | Cathode |
|---|---|---|---|---|---|---|---|---|
| Light-emitting element 1 | ITSO 110 nm | DBT3P-II:MoOx (=4:2) 20 nm | BPAFLP 20 nm | See below | 2mDBTBPDBq-II 10 nm | BPhen 15 nm | LiF 1 nm | Al 200 nm |
| Light-emitting element 2 | ITSO 110 nm | DBT3P-II:MoOx (=4:2) 20 nm | BPAFLP 20 nm | See below | 2mDBTBPDBq-II 15 nm | BPhen 10 nm | LiF 1 nm | Al 200 nm |
| Light-emitting element 3 | ITSO 110 nm | DBT3P-II:MoOx (=4:2) 20 nm | BPAFLP 20 nm | See below | 2mDBTBPDBq-II 15 nm | BPhen 10 nm | LiF 1 nm | Al 200 nm |
| Light-emitting element 4 | ITSO 110 nm | DBT3P-II:MoOx (=4:2) 20 nm | BPAFLP 20 nm | See below | 2mDBTBPDBq-II 15 nm | BPhen 10 nm | LiF 1 nm | Al 200 nm |
| Light-emitting element 5 | ITSO 110 nm | DBT3P-II:MoOx (=4:2) 20 nm | BPAFLP 20 nm | See below | 2mDBTBPDBq-II 15 nm | BPhen 10 nm | LiF 1 nm | Al 200 nm |

| | |
|---|---|
| Light-emitting element 1 | 2mDBTBPDBq-II:PCBBiF:Ir(tBupc zpm)$_2$(dpm) (=0.8:0.2:0.05) 40 nm |
| Light-emitting element 2 | 2mDBTBPDBq-II:PCBBiF:Ir(tBupc zpm)$_2$(acac) (=0.8:0.2:0.05) 40 nm |
| Light-emitting element 3 | 2mDBTBPDBq-II:PCBBiF:Ir(tBuec zpm)$_2$(acac) (=0.8:0.2:0.025) 40 nm |
| Light-emitting element 4 | 2mDBTBPDBq-II:PCBBiF:Ir(tBuec zpm)$_3$ (=0.8:0.2:0.025) 40 nm |
| Light-emitting element 5 | 2mDBTBPDBq-II:Ir(tBupc zpm)$_3$ (=1:0.05) 40 nm |

Then, in a glove box containing a nitrogen atmosphere, the light-emitting elements 1 to 5 were sealed so as not to be exposed to the air (specifically, a sealant was applied onto an outer edge of the elements and heat treatment was performed at 80° C. for 1 hour at the time of sealing). After that, the operating characteristics of the light-emitting elements 1 to 5 were measured. Note that the measurement was carried out at room temperature (in an atmosphere kept at 25° C.).

Figure 25A:
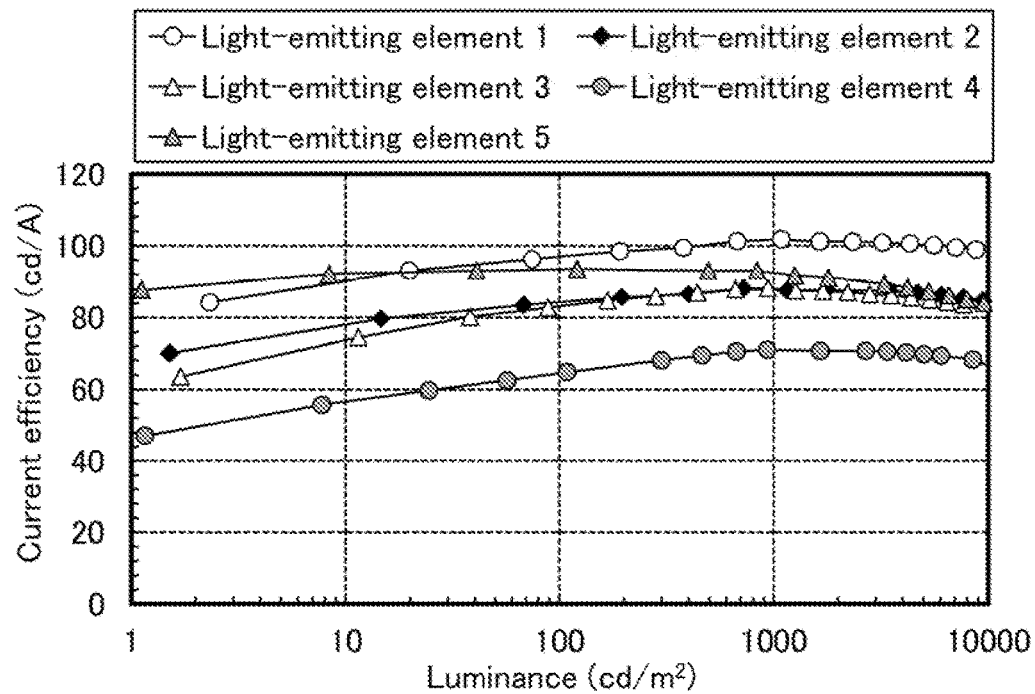
FIGS. 25A and 25B show luminance-current efficiency characteristics and voltage-current characteristics of light-emitting elements 1 to 5.
Figure 25B:
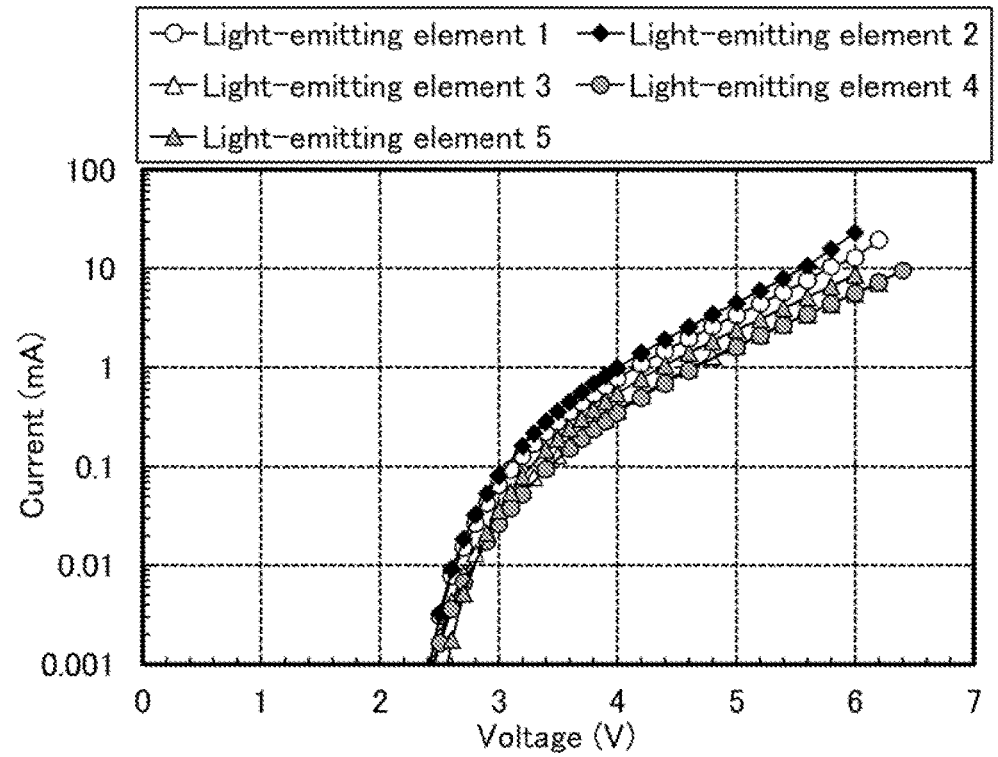
Figure 26A:
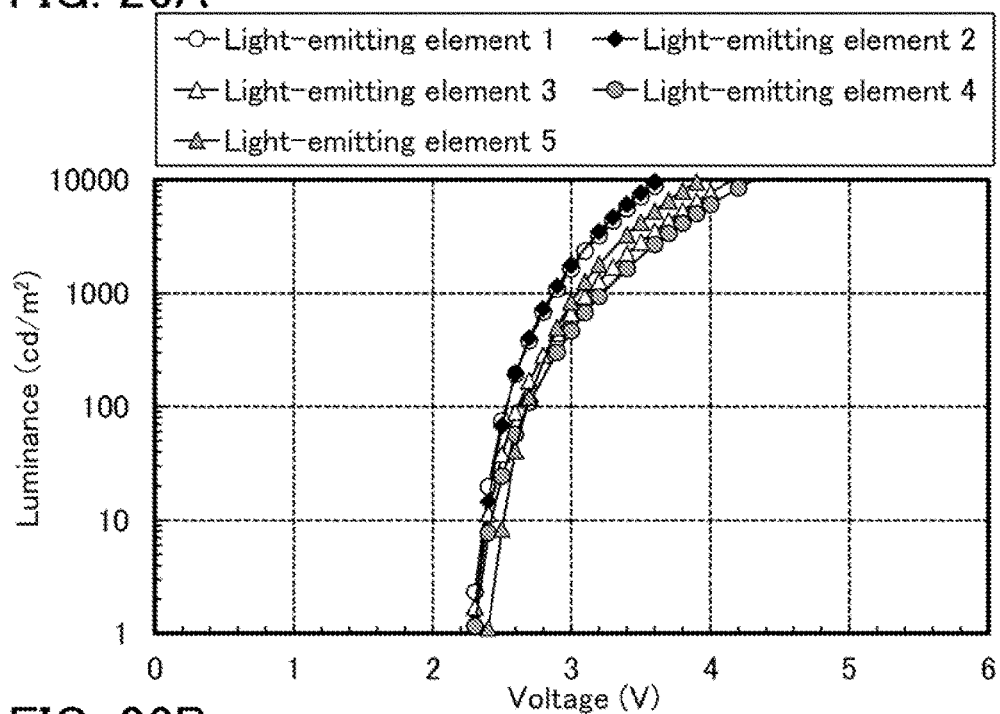
FIGS. 26A and 26B show voltage-luminance characteristics and luminance-external quantum efficiency characteristics of the light-emitting elements 1 to 5.
Figure 26B:
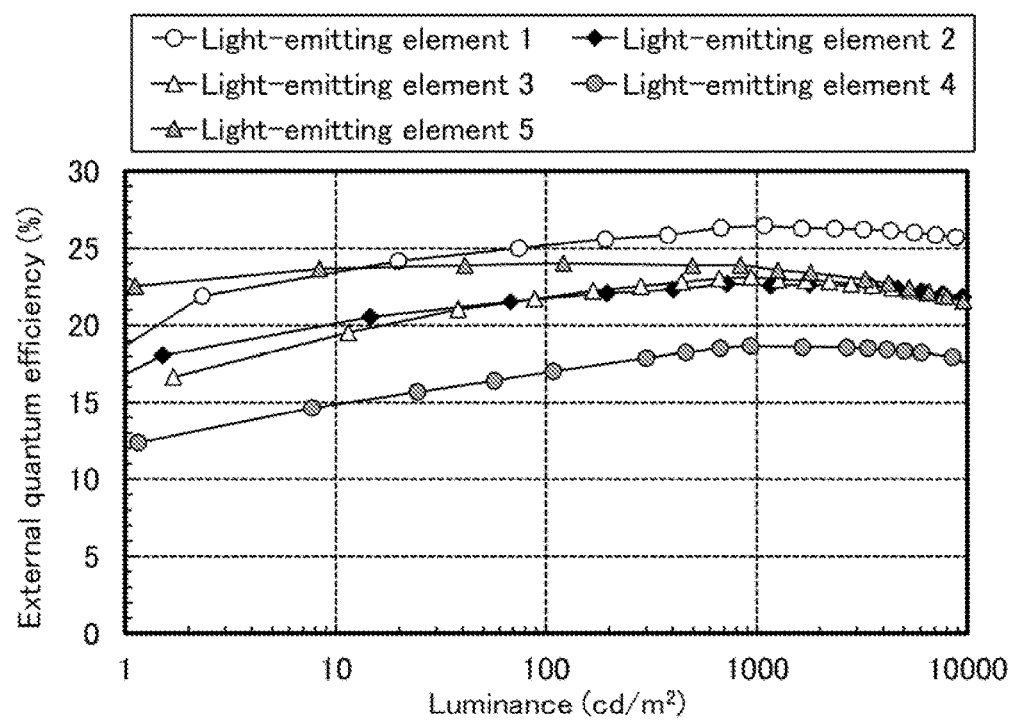

FIG. 25A shows luminance-current efficiency characteristics of the light-emitting elements 1 to 5. In FIG. 25A, the horizontal axis represents luminance ($cd/m^2$) and the vertical axis represents current efficiency (cd/A). FIG. 25B shows voltage-current characteristics of the light-emitting elements 1 to 5. In FIG. 25B, the horizontal axis represents voltage (V) and the vertical axis represents current (mA). FIG. 26A shows voltage-luminance characteristics of the light-emitting elements 1 to 5. In FIG. 26A, the horizontal axis represents voltage (V) and the vertical axis represents luminance ($cd/m^2$). FIG. 26B shows luminance-external quantum efficiency characteristics of the light-emitting elements 1 to 5. In FIG. 26B, the horizontal axis represents luminance ($cd/m^2$) and the vertical axis represents external quantum efficiency (%).

FIGS. 25A and 25B and FIGS. 26A and 26B show that the light-emitting elements 1 to 5 each have low driving voltage, low power consumption, and high efficiency.

Table 2 shows the voltage (V), current density ($mA/cm^2$), CIE chromaticity coordinates (x, y), luminance ($cd/m^2$), current efficiency (cd/A), and external quantum efficiency (%) of the light-emitting elements 1 to 5 at a luminance of 1000 $cd/m^2$.

TABLE 2

| | Voltage (V) | Current density ($mA/cm^2$) | Chromaticity x, y | | Luminance ($cd/m^2$) | Current efficiency (cd/A) | External quantum efficiency (%) |
|---|---|---|---|---|---|---|---|
| Light-emitting element 1 | 2.9 | 1.1 | 0.41 | 0.58 | 1087 | 102 | 26 |
| Light-emitting element 2 | 2.8 | 0.8 | 0.40 | 0.59 | 723 | 88 | 23 |
| Light-emitting element 3 | 3.1 | 1.1 | 0.41 | 0.58 | 939 | 88 | 23 |
| Light-emitting element 4 | 3.2 | 1.3 | 0.37 | 0.61 | 932 | 71 | 13 |
| Light-emitting element 5 | 3.0 | 0.9 | 0.36 | 0.62 | 836 | 93 | 18 |

Figure 27:
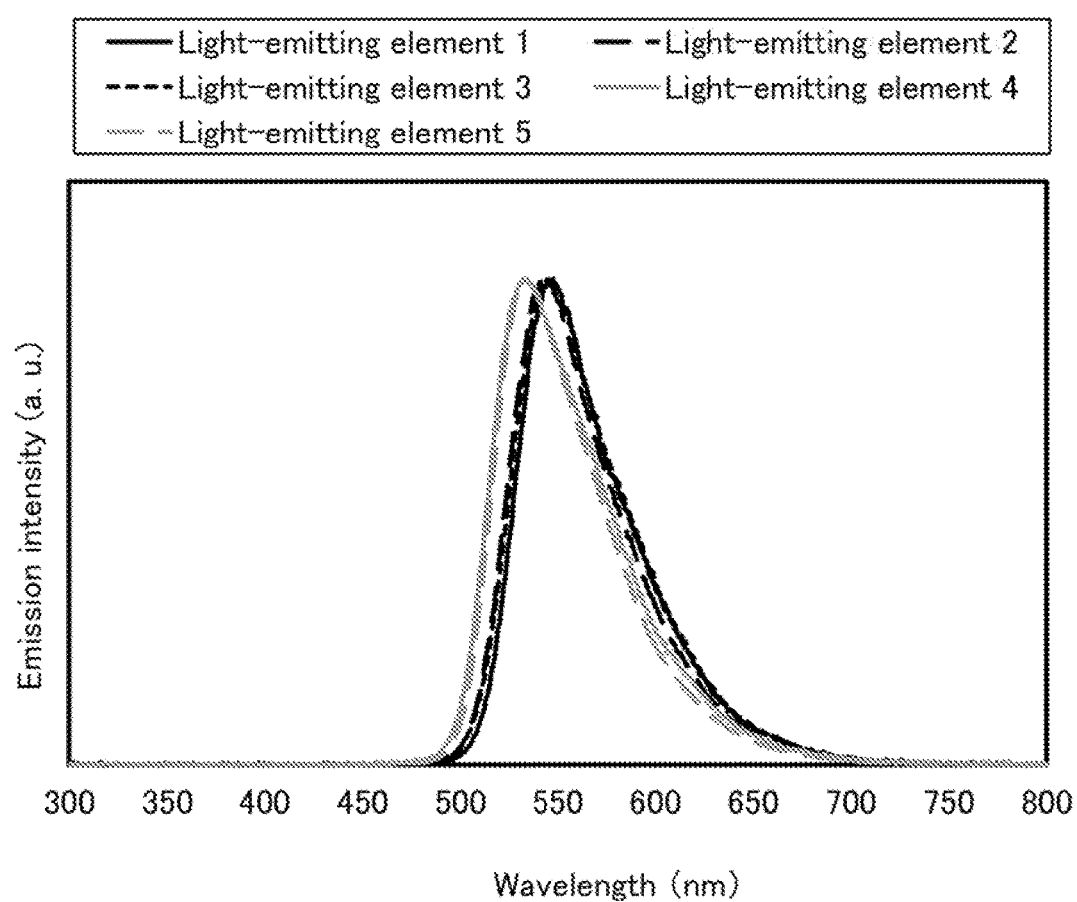
FIG. 27 shows emission spectra of the light-emitting elements 1 to 5.

FIG. 27 shows emission spectra of the light-emitting elements 1 to 5 when current was supplied thereto at a current density of 2.5 $mA/cm^2$. As shown in FIG. 27, the emission spectra of the light-emitting elements 1, 2, 3, 4, and 5 had peaks at 545 nm, 543 nm, 548 nm, 532 nm, and 534 nm, respectively. Note that in FIG. 27, the emission spectra of the light-emitting elements 1 to 5 substantially overlap one another.

As shown in Table 2, the light-emitting element 1 had a voltage of 2.9 V, a current density of 1.1 $mA/cm^2$, a current efficiency of 102 cd/A, and an external quantum efficiency of 26% at a luminance of 1087 $cd/m^2$; the light-emitting element 2 had a voltage of 2.8 V, a current density of 0.8 $mA/cm^2$, a current efficiency of 88 cd/A, and an external quantum efficiency of 23% at a luminance of 723 $cd/m^2$; the light-emitting element 3 had a voltage of 3.1 V, a current density of 1.1 $mA/cm^2$, a current efficiency of 88 cd/A, and an external quantum efficiency of 23% at a luminance of 939 $cd/m^2$; the light-emitting element 4 had a voltage of 3.2 V, a current density of 1.3 $mA/cm^2$, a current efficiency of 71 cd/A, and an external quantum efficiency of 13% at a luminance of 932 $cd/m^2$; the light-emitting element 5 had a voltage of 3.0 V, a current density of 0.9 $mA/cm^2$, a current efficiency of 93 cd/A, and an external quantum efficiency of 18% at a luminance of 836 $cd/m^2$.

In addition, as shown in Table 2, the CIE chromaticity coordinates (x, y) of the light-emitting element 1 were (0.41, 0.58) when the luminance was 1087 $cd/m^2$; the CIE chromaticity coordinates (x, y) of the light-emitting element 2 were (0.40, 0.59) when the luminance was 723 $cd/m^2$; the CIE chromaticity coordinates (x, y) of the light-emitting element 3 were (0.41, 0.58) when the luminance was 939 $cd/m^2$; the CIE chromaticity coordinates (x, y) of the light-emitting element 4 were (0.37, 0.61) when the luminance was 932 $cd/m^2$; the CIE chromaticity coordinates (x, y) of the light-emitting element 5 were (0.36, 0.62) when the luminance was 836 $cd/m^2$. These results demonstrate that light emission originating from the dopant was obtained from each of the light-emitting elements 1 to 5.

The above-described characteristics demonstrate that the light-emitting elements 1 to 5, in each of which the organometallic complex of one embodiment of the present invention was used for the light-emitting layer, were able to efficiently emit light in the green wavelength range. It was thus found that the organometallic complex of one embodiment of the present invention is suitable as a guest material emitting light in the green wavelength range.

Next, reliability tests were performed on the light-emitting elements 1 to 5. Results of the reliability tests are shown in FIG. 28.

In the reliability tests, the light-emitting elements 1 to 5 were driven under the conditions where the initial luminance was 5000 $cd/m^2$ and the current density was constant. The horizontal axis represents driving time (h) of the elements and the vertical axis represents normalized luminance (%) on the assumption that the initial luminance is 100%. FIG. 28 shows that the normalized luminance of the light-emitting element 1 after 187 hours was 88%. The normalized luminance of the light-emitting element 2 after 317 hours was 77%. The normalized luminance of the light-emitting element 3 after 137 hours was 83%. The normalized luminance of the light-emitting element 4 after 137 hours was 77%. The normalized luminance of the light-emitting element 5 after 237 hours was 82%.

Figure 28:
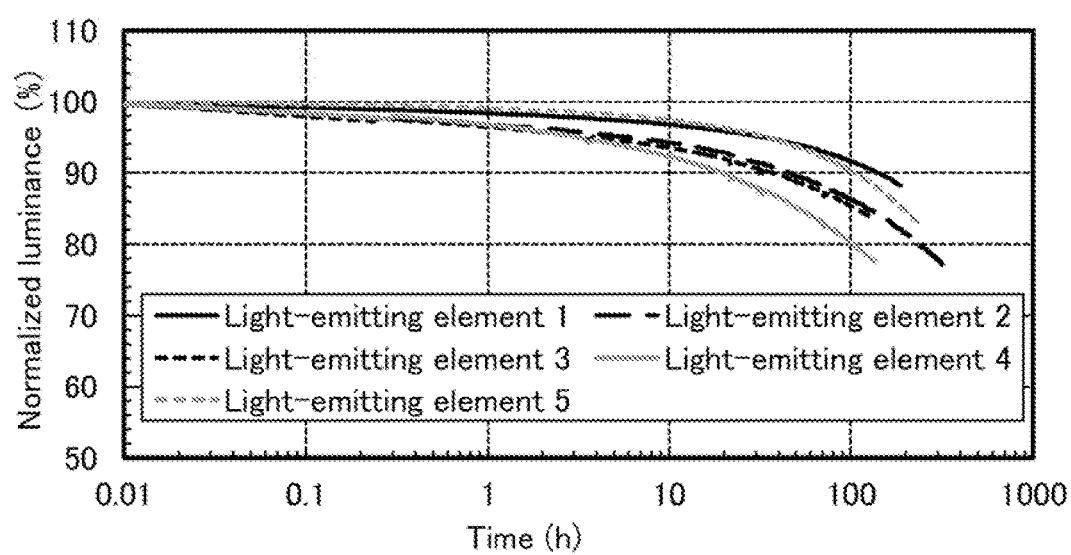
FIG. 28 shows time-normalized luminance characteristics of the light-emitting elements 1 to 5.

The results shown in FIG. 28 demonstrate that the light-emitting elements 1 to 5, each of which is one embodiment of the present invention, each have a long lifetime.

Example 7

Figure 24B:
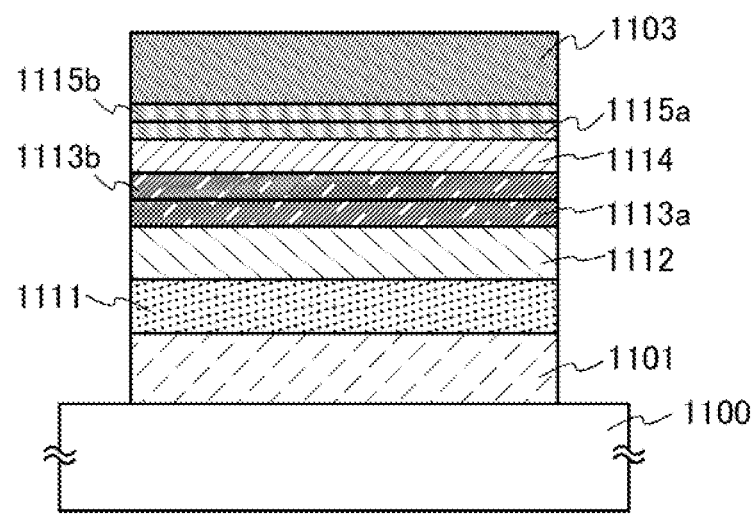

In this example, a light-emitting element (light-emitting element 6) of one embodiment of the present invention is described with reference to FIG. 24B. Note that materials used in this example are the same as those in Example 6; therefore, the chemical formulae shown in Example 6 can be referred to for the materials used in this example.

A method for manufacturing the light-emitting element 6 of this example is described below.

(Light-Emitting Element 6)

First, an indium oxide-tin oxide compound containing silicon or silicon oxide (ITSO) was deposited by a sputtering method over a substrate 1100, so that a first electrode 1101 was formed. Note that the composition ratio of target materials used was the same as that in Example 3. The thickness of the first electrode 1101 was 110 nm and the electrode area was 2 mm×2 mm. Here, the first electrode 1101 functions as an anode of the light-emitting element.

Next, as pretreatment for forming the light-emitting element over the substrate 1100, the surface of the substrate was washed, baked at 200° C. for 1 hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that the surface on which the first electrode 1101 was provided faced downward. The pressure in the vacuum evaporation apparatus was reduced to about $10^{-4}$ Pa. Then, DBT3P-II and molybdenum oxide were deposited by co-evaporation, so that a hole-injection layer 1111 was formed on the first electrode 1101. The thickness of the hole-injection layer 1111 was 20 nm. The weight ratio of DBT3P-II to molybdenum oxide was adjusted to 4:2 (=DBT3P-II:molybdenum oxide).

Next, on the hole-injection layer 1111, BPAFLP was deposited to a thickness of 20 nm, so that a hole-transport layer 1112 was formed.

In addition, on the hole-transport layer 1112, 2mDBTBPDBq-II, PCBBiF, and Ir(tBupczpm)$_3$ synthesized in Example 3 were deposited by co-evaporation, so that a first light-emitting layer 1113a was formed. Here, the weight ratio of 2mDBTBPDBq-II to PCBBiF and Ir(tBupczpm)$_3$ was adjusted to 0.7:0.3:0.05 (=2mDBTBPDBq-II:PCBBiF:Ir(tBupczpm)$_3$). The thickness of the first light-emitting layer 1113a was 20 nm.

In the first light-emitting layer 1113a of the light-emitting element 6, 2mDBTBPDBq-II served as a host material, PCBBiF served as an assist material, and Ir(tBupczpm)$_3$ served as a guest material (dopant). Note that Ir(tBupczpm)$_3$ is an organometallic complex of one embodiment of the present invention.

Then, on the first light-emitting layer 1113a, 2mDBTBPDBq-II, PCBBiF, and Ir(tBupczpm)$_3$ synthesized in Example 5 were deposited by co-evaporation, so that a second light-emitting layer 1113b was formed. Here, the weight ratio of 2mDBTBPDBq-II to PCBBiF and Ir(tBupczpm)$_3$ was adjusted to 0.8:0.2:0.05 (=2mDBTBPDBq-II:PCBBiF:Ir(tBupczpm)$_3$). The thickness of the second light-emitting layer 1113b was 20 nm.

In the second light-emitting layer 1113b of the light-emitting element 6, 2mDBTBPDBq-II served as a host material, PCBBiF served as an assist material, and Ir(tBueczpm)$_3$ served as a guest material (dopant). Note that Ir(tBueczpm)$_3$ is the organometallic complex of one embodiment of the present invention.

Then, on the second light-emitting layer 1113b, 2mDBTBPDBq-II was deposited to a thickness of 25 nm, so that an electron-transport layer 1114 was formed.

Then, on the electron-transport layer 1114, BPhen was deposited to a thickness of 10 nm, so that a first electron-injection layer 1115a was formed.

Furthermore, on the first electron-injection layer 1115a, lithium fluoride (LiF) was deposited by evaporation to a thickness of 1 nm, so that a second electron-injection layer 1115b was formed.

Lastly, aluminum was deposited by evaporation to a thickness of 200 nm, so that a second electrode 1103 functioning as a cathode was formed. Thus, the light-emitting element 6 of this example was manufactured.

Table 3 shows an element structure of the light-emitting element 6 obtained as described above.

TABLE 3

| | Anode | Hole-injection layer | Hole-transport layer | First light-emitting layer | Second light-emitting layer | Electron-transport layer | First electron-injection layer | Second electron-injection layer | Cathode |
|---|---|---|---|---|---|---|---|---|---|
| Light-emitting element 6 | ITSO 110 nm | DBT3P-II:MoOx (=4:2) 20 nm | BPAFLP 20 nm | See below | See below | 2mDBTBPDBq-II 25 nm | BPhen 10 nm | LiF 1 nm | Al 200 nm |

| Light-emitting element 6 | 2mDBTBPDBq-II:PCBBiF:Ir(tBupc zpm)$_3$ (=0.7:0.3:0.05) 20 nm | 2mDBTBPDBq-II:PCBBiF:Ir(tBupc zpm)$_3$ (=0.8:0.2:0.05) 20 nm |
|---|---|---|

Then, in a glove box containing a nitrogen atmosphere, the light-emitting element 6 was sealed so as not to be exposed to the air (specifically, a sealant was applied onto an outer edge of the elements and heat treatment was performed at 80° C. for 1 hour at the time of sealing). After that, the operating characteristics of the light-emitting element 6 was measured. Note that the measurement was carried out at room temperature (in an atmosphere kept at 25° C.).

Figure 29A:
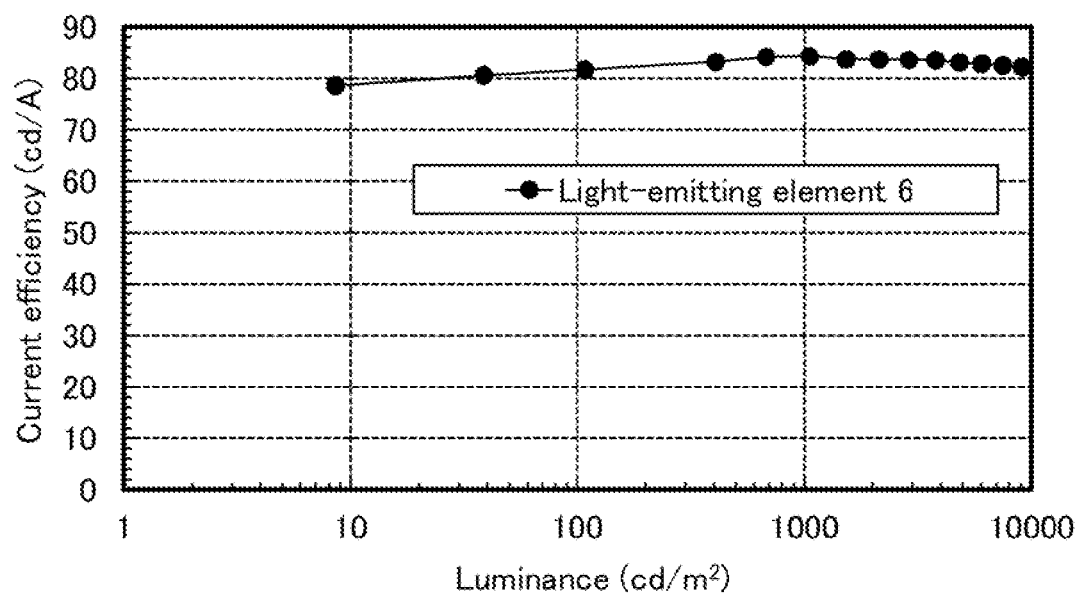
FIGS. 29A and 29B show luminance-current efficiency characteristics and voltage-current characteristics of a light-emitting element 6.
Figure 29B:
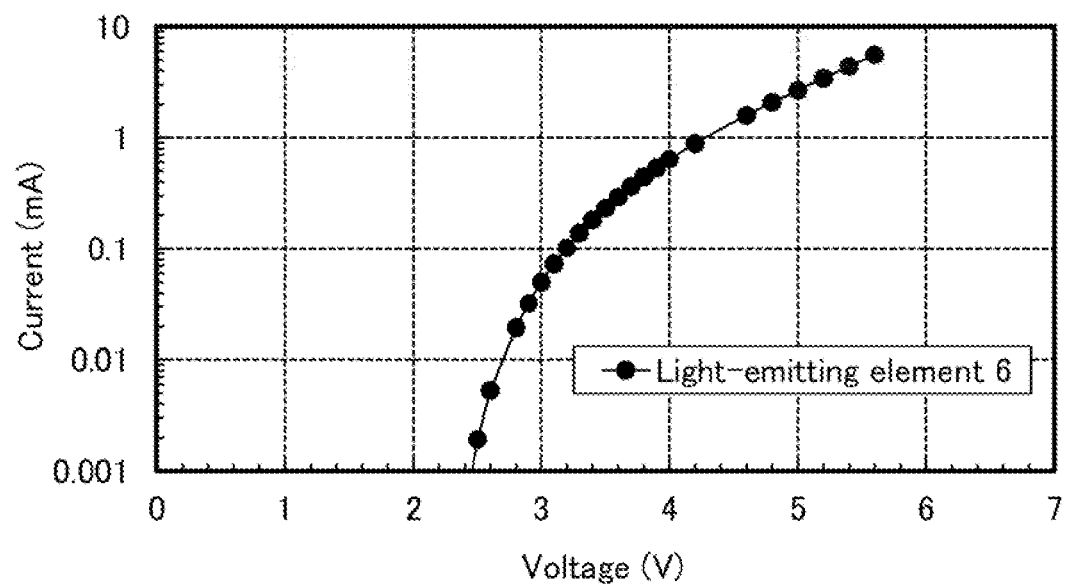
Figure 30A:
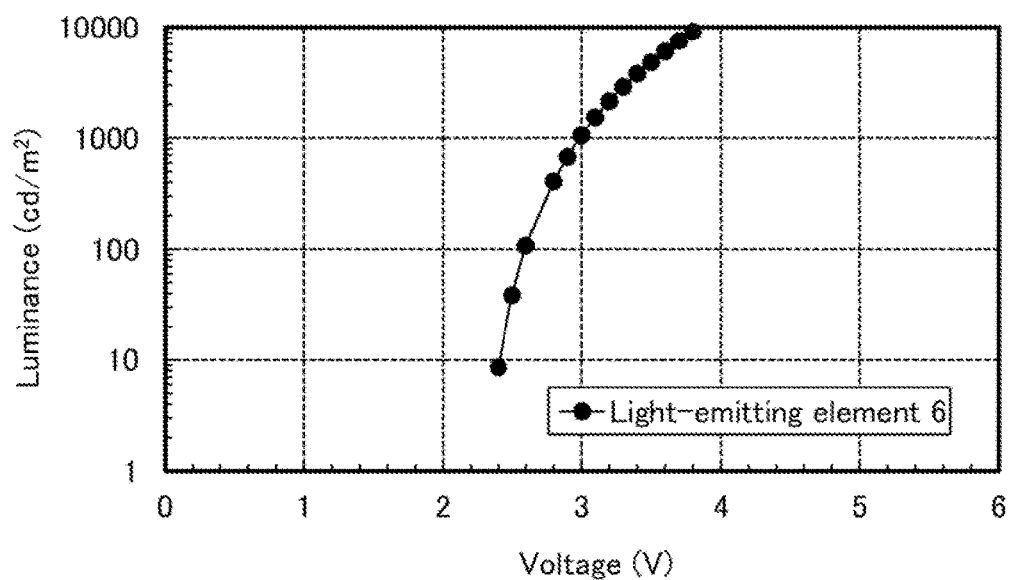
FIGS. 30A and 30B show voltage-luminance characteristics and luminance-external quantum efficiency characteristics of the light-emitting element 6.
Figure 30B:
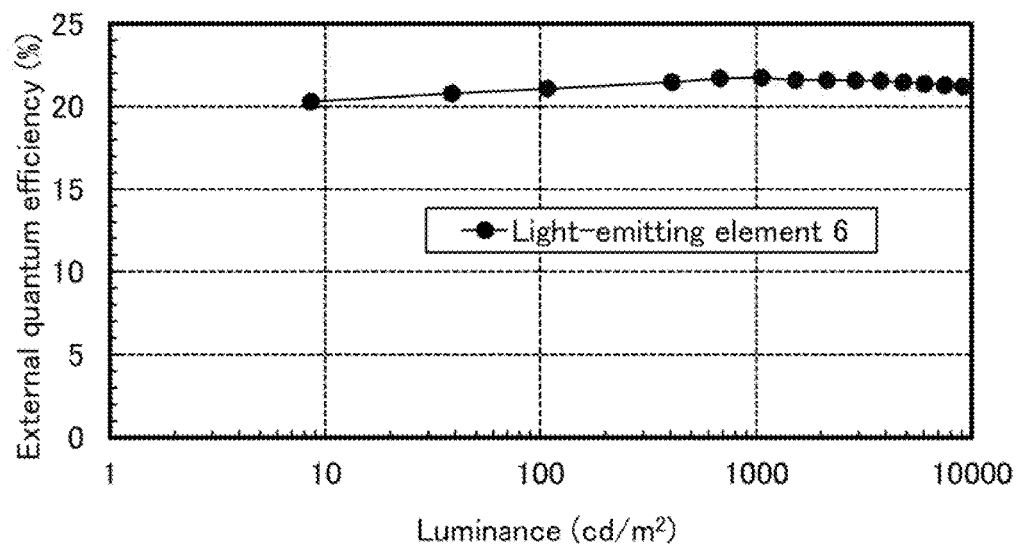

FIG. 29A shows luminance-current efficiency characteristics of the light-emitting element 6. In FIG. 29A, the horizontal axis represents luminance (cd/m$^2$) and the vertical axis represents current efficiency (cd/A). FIG. 29B shows voltage-current characteristics of the light-emitting element 6. In FIG. 29B, the horizontal axis represents voltage (V) and the vertical axis represents current (mA). FIG. 30A shows voltage-luminance characteristics of the light-emitting element 6. In FIG. 30A, the horizontal axis represents voltage (V) and the vertical axis represents luminance (cd/m$^2$). FIG. 30B shows luminance-external quantum efficiency characteristics of the light-emitting element 6. In FIG. 30B, the horizontal axis represents luminance (cd/m$^2$) and the vertical axis represents external quantum efficiency (%).

FIGS. 29A and 29B and FIGS. 30A and 30B show that the light-emitting element 6 has low driving voltage, low power consumption, and high efficiency.

Table 4 shows the voltage (V), current density (mA/cm$^2$), CIE chromaticity coordinates (x, y), luminance (cd/m$^2$), current efficiency (cd/A), and external quantum efficiency (%) of the light-emitting element 6 at a luminance of 1000 cd/m$^2$.

|  | Voltage (V) | Current density (mA/cm$^2$) | Chromaticity x, y | | Luminance (cd/m$^2$) | Current efficiency (cd/A) | External quantum efficiency (%) |
|---|---|---|---|---|---|---|---|
| Light-emitting element 6 | 3.0 | 1.3 | 0.37 | 0.62 | 1058 | 84 | 22 |

Figure 31:
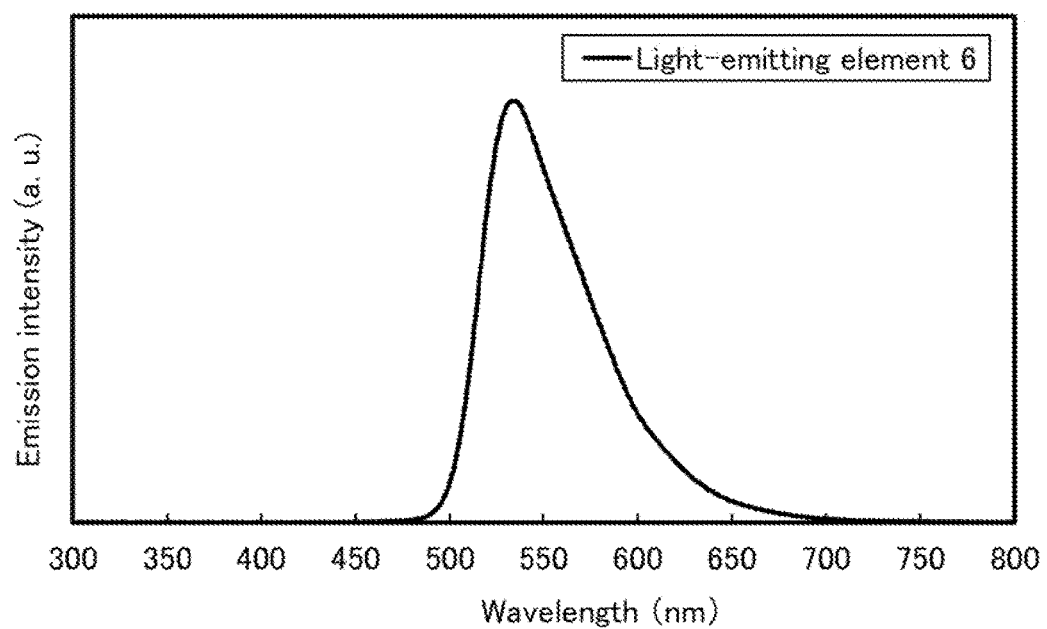
FIG. 31 shows an emission spectrum of the light-emitting element 6.

FIG. 31 shows emission spectra of the light-emitting element 6 when current was supplied thereto at a current density of 2.5 mA/cm. As shown in FIG. 31, the emission spectrum of the light-emitting element 6 had a peak at 534 nm.

As shown in Table 4, the light-emitting element 6 had a voltage of 3.0 V, a current density of 1.3 mA/cm$^2$, a current efficiency 84 cd/A, and an external quantum efficiency of 22% when the luminance was 1058 cd/m$^2$.

As shown in Table 4, the CIE chromaticity coordinates (x, y) of the light-emitting element 1 were (0.37, 0.62) when the luminance was 1058 cd/m$^2$. These results demonstrate that light emission originating from the dopant was obtained from the light-emitting element 6.

The above-described characteristics demonstrate that the light-emitting element 6, in which the organometallic complex of one embodiment of the present invention was used for the light-emitting layer, was able to efficiently emit light in the green wavelength range. It was thus found that the organometallic complex of one embodiment of the present invention is suitable as a guest material emitting light in the green wavelength range.

Next, a reliability test were performed on the light-emitting element 6. Results of the reliability test are shown in FIG. 32.

In the reliability tests, the light-emitting element 6 was driven under the conditions where the initial luminance was 5000 cd/m$^2$ and the current density was constant. The horizontal axis represents driving time (h) of the element and the vertical axis represents normalized luminance (%) on the assumption that the initial luminance is 100%. FIG. 32 shows that the normalized luminance of the light-emitting element 6 after 473 hours was 90%.

Figure 32:
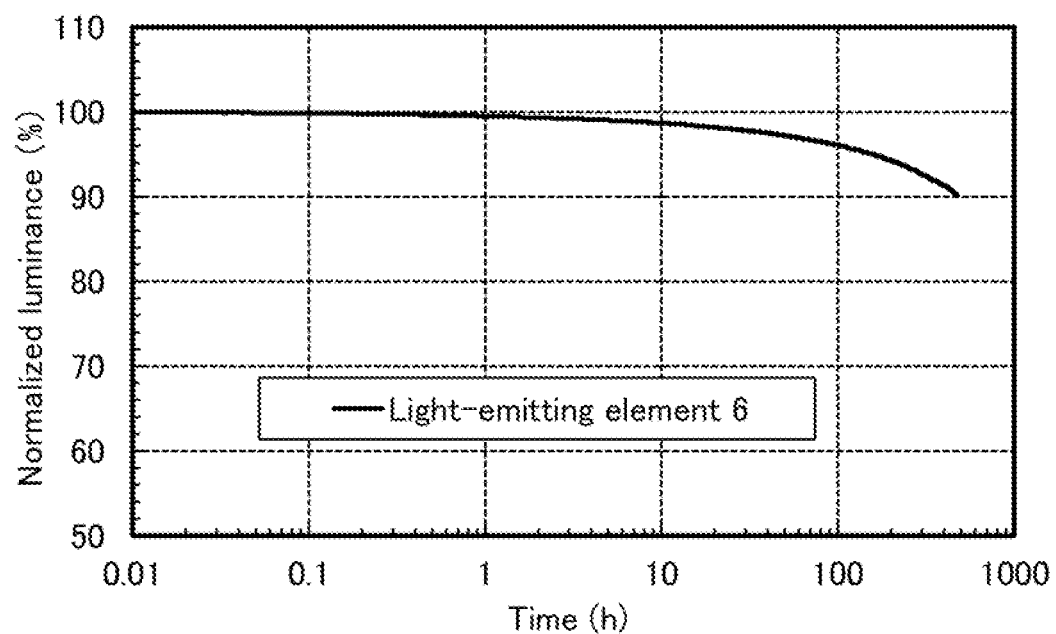
FIG. 32 shows time-normalized luminance characteristics of the light-emitting element 6.

The results shown in FIG. 32 demonstrate that the light-emitting element 6 of one embodiment of the present invention, have a long lifetime.

Reference Example

A method of synthesizing PCBBiF used in Example 6 and Example 7 is described below.

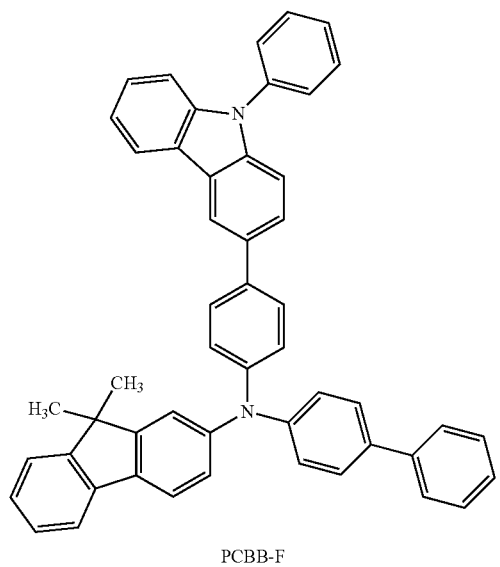

PCBB-F

Step 1: Synthesis of N-(1,1'-biphenyl-4-yl)-9,9-dimethyl-N-phenyl-9H-fluoren-2-amine A synthesis scheme of Step 1 is shown in (x-1).

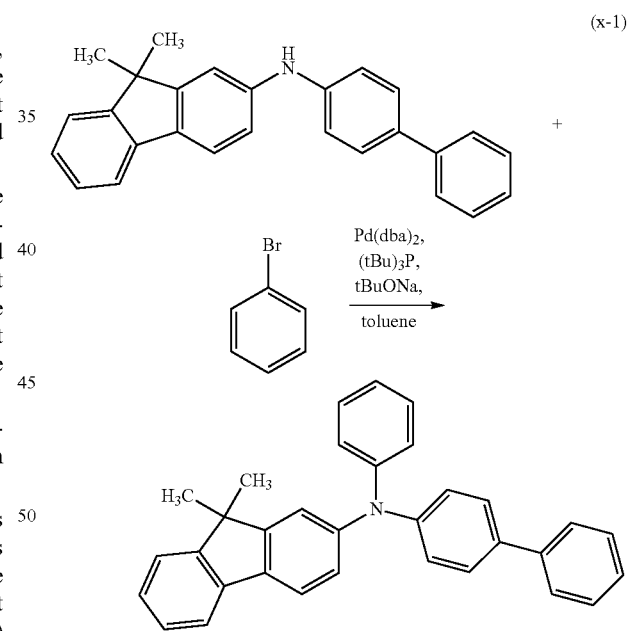

(x-1)

In a 1-L three-neck flask were put 45 g (0.13 mol) of N-(1,1'-biphenyl-4-yl)-9,9-dimethyl-9H-fluoren-2-amine, 36 g (0.38 mol) of sodium tert-butoxide, 21 g (0.13 mol) of bromobenzene, and 500 mL of toluene. This mixture was degassed by being stirred under reduced pressure. After that, 0.8 g (1.4 mmol) of bis(dibenzylideneacetone)palladium(0) and 12 mL (5.9 mmol) of tri(tert-butyl)phosphine (a 10 wt % hexane solution) were added thereto.

This mixture was stirred under a nitrogen stream at 90° C. for 2 hours. Then, the mixture was cooled down to room temperature, and a solid was separated by suction filtration.

The obtained filtrate was concentrated to give about 200 mL of a brown solution. The brown solution was mixed with toluene, and the resulting solution was purified using Celite (manufactured by Wako Pure Chemical Industries, Ltd., Catalog No. 531-16855 (the same applies to Celite in the following description and the description is repeated)), alumina, Florisil (manufactured by Wako Pure Chemical Industries, Ltd., Catalog No. 540-00135 (the same applies to Florisil in the following description and the description is repeated)). The obtained filtrate was concentrated to give a light yellow solution. The light yellow solution was recrystallized from hexane to give 52 g of target light yellow powder in a yield of 95%.

Step 2: Synthesis of N-(1,1'-biphenyl-4-yl)-N-(4-bromophenyl)-9,9-dimethyl-9H-fluoren-2-amine A synthesis scheme of Step 2 is shown in (x-2).

(x-2)

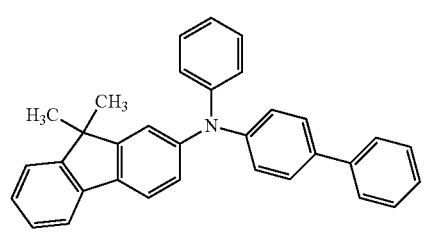

NBS,
toluene,
ethyl acetate

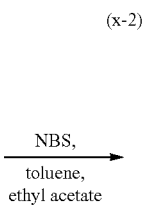

In a 1-L Mayer flask was put 45 g (0.10 mol) of N-(1,1'-biphenyl-4-yl)-9,9-dimethyl-N-phenyl-9H-fluoren-2-amine, which was then dissolved in 225 mL of toluene by stirring while being heated. This solution was cooled down to room temperature, 225 mL of ethyl acetate was added thereto, and 18 g (0.10 mol) of N-bromosuccinimide (abbreviation: NBS) was added thereto. The mixture was stirred at room temperature for 2.5 hours. After the stirring, the mixture was washed three times with a saturated aqueous solution of sodium hydrogen carbonate, and washed once with saturated saline. Then, magnesium sulfate was added to the obtained organic layer, and the obtained mixture was dried for 2 hours. The obtained mixture was subjected to natural filtration to remove magnesium sulfate, and the filtrate was concentrated to give a yellow solution. This yellow solution and toluene were mixed, and the obtained solution was filtered through Celite, alumina, and Florisil. The resulting filtrate was concentrated to give a light yellow solid. This light yellow solid was recrystallized from toluene/ethanol to give 47 g of an objective white powder in a yield of 89%.

Step 3: Synthesis of PCBBiF

A synthesis scheme of Step 3 is shown in (x-3).

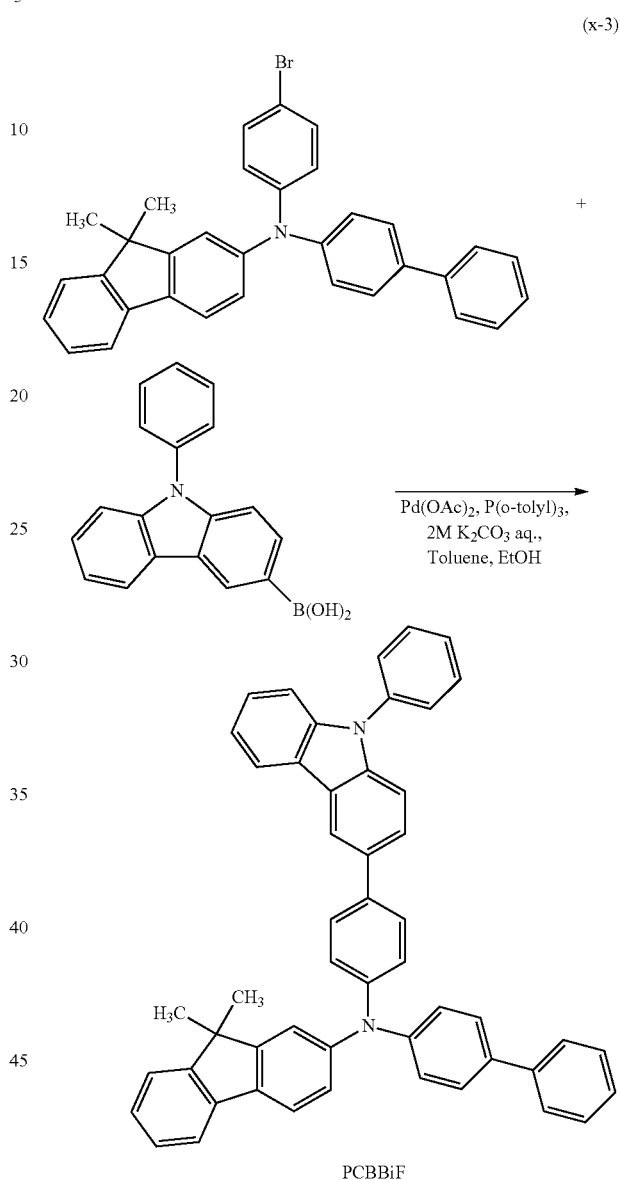

PCBBiF

In a 1-L three-neck flask were put 41 g (80 mmol) of N-(1,1'-biphenyl-4-yl)-N-(4-bromophenyl)-9,9-dimethyl-9H-fluoren-2-amine and 25 g (88 mmol) of 9-phenyl-9H-carbazole-3-boronic acid, and 240 mL of toluene, 80 mL of ethanol, and 120 mL (2.0 mol/L) of a potassium carbonate solution were added thereto. This mixture was degassed by being stirred under reduced pressure, and then the atmosphere in the flask was replaced with nitrogen. To the mixture were added 27 mg (0.12 mmol) of palladium(II) acetate and 154 mg (0.5 mmol) of tri(ortho-tolyl)phosphine, and this mixture was degassed by being stirred under reduced pressure, and then the atmosphere in the flask was replaced with nitrogen. This mixture was stirred under a nitrogen stream at 110° C. for 1.5 hours.

After that, the mixture was cooled down to room temperature while being stirred, and an aqueous layer of the mixture was extracted twice with toluene. The extracted solution and the organic layer were combined and washed twice with water and twice with saturated saline. To this solution was added magnesium sulfate, and the mixture was dried. The obtained mixture was subjected to natural filtration to remove magnesium sulfate, and the filtrate was concentrated to give a brown solution. This brown solution and toluene were mixed, and the obtained solution was filtered through Celite, alumina, and Florisil. The resulting filtrate was concentrated to give a light yellow solid. This light yellow solid was recrystallized from ethyl acetate/ethanol to give 46 g of an objective light yellow powder in a yield of 88%.

Then, 38 g of the obtained light yellow powder was purified by a train sublimation method. In the purification by sublimation, the light yellow powder was heated at 345° C. under a pressure of 3.7 Pa with a flow rate of argon gas of 15 mL/min. After the purification by sublimation, 31 g of a light yellow powder was obtained at a collection rate of 83%.

This compound was identified as PCBBiF that was the target substance by nuclear magnetic resonance ($^1$H-NMR) spectroscopy.

$^1$H-NMR data of the obtained light yellow solid are as follows: $^1$H-NMR (CDCl$_3$, 500 MHz): δ=1.45 (s, 6H), 7.18 (d, J=8.0 Hz, 1H), 7.27-7.32 (m, 8H), 7.40-7.50 (m, 7H), 7.52-7.53 (m, 2H), 7.59-7.68 (m, 12H), 8.19 (d, J=8.0 Hz, 1H), 8.36 (d, J=1.1 Hz, 1H).

This application is based on Japanese Patent Application serial no. 2013-106142 filed with the Japan Patent Office on May 20, 2013, the entire contents of which are hereby incorporated by reference.

What is claimed is:

1. A compound represented by any one of Formulae (100), (101), (110), (112), and (113):

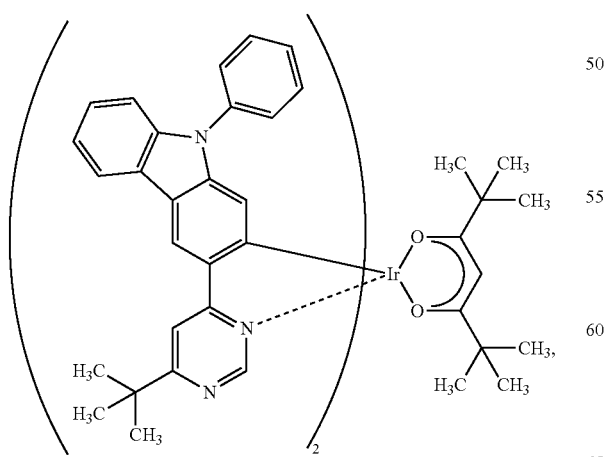

(100)

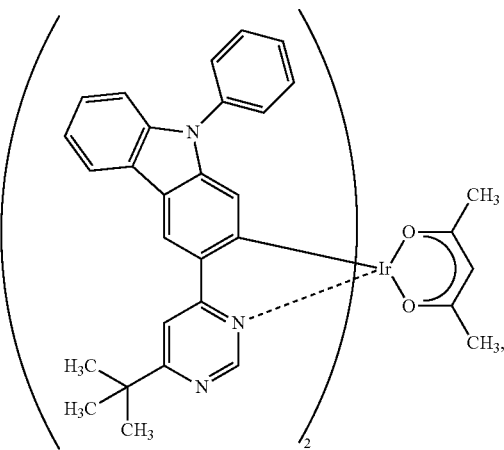

(101)

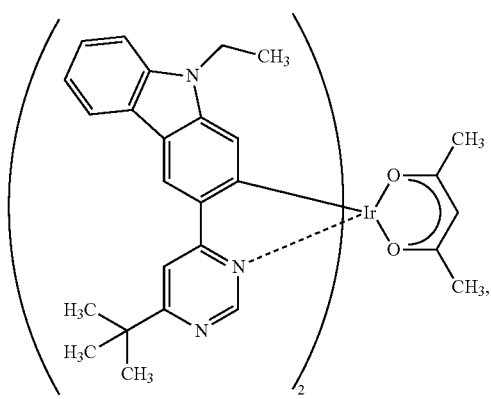

(110)

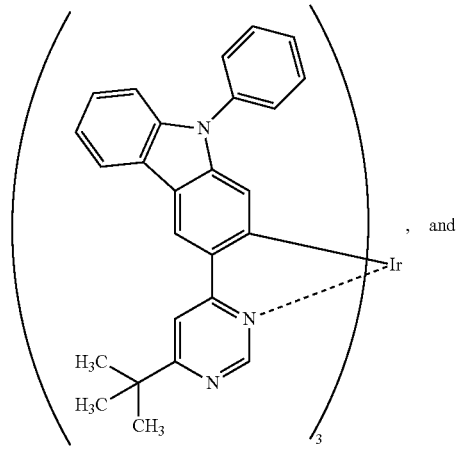

(112)

, and

-continued
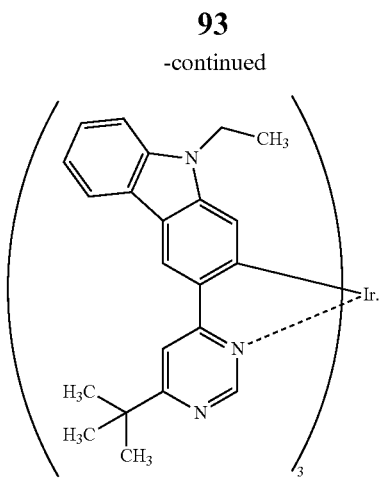
(113)
2. A light-emitting device comprising:
a light-emitting layer between a pair of electrodes, the light-emitting layer comprising a compound,
wherein the compound is represented by any one of Formulae (100), (101), (110), (112), and (113):
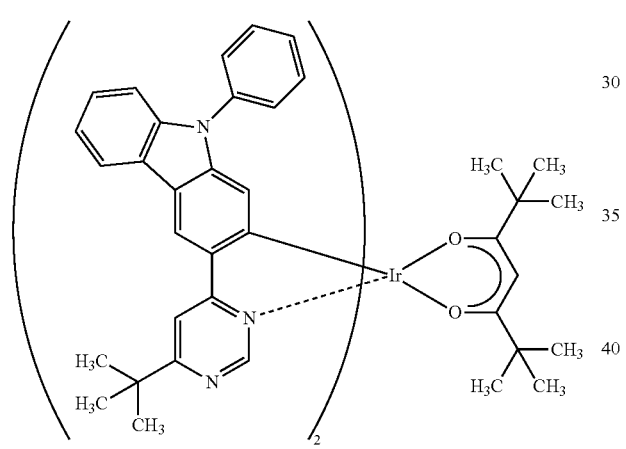
(100)
(101)
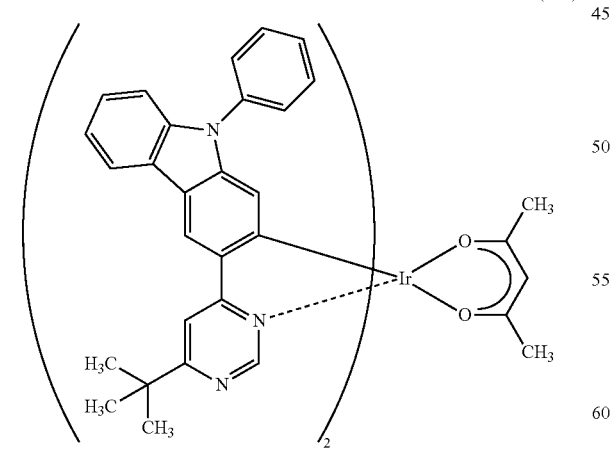
-continued
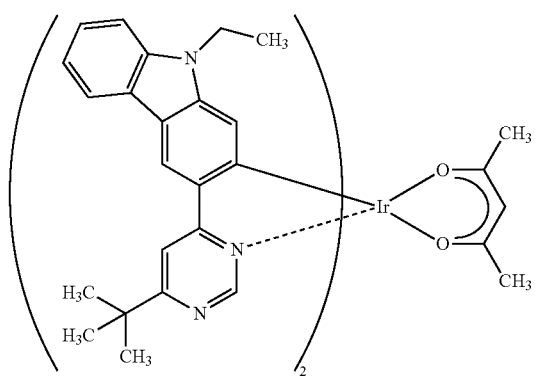
(110)
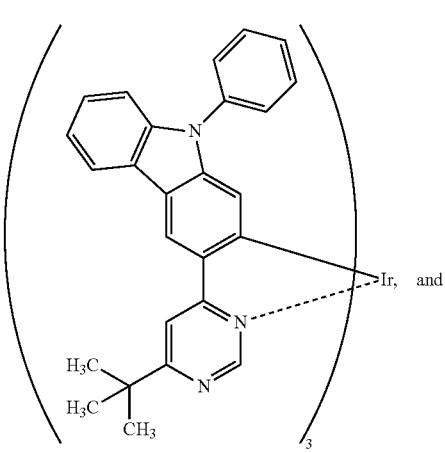
(112)
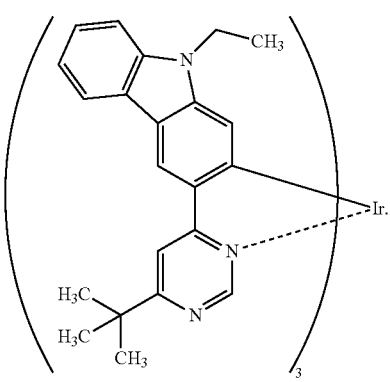
(113)
* * * * *